United States Patent
Takahashi et al.

(10) Patent No.: US 10,424,794 B2
(45) Date of Patent: Sep. 24, 2019

(54) IONIC COMPLEX, ELECTROLYTE FOR NONAQUEOUS ELECTROLYTE BATTERY, NONAQUEOUS ELECTROLYTE BATTERY AND IONIC COMPLEX SYNTHESIS METHOD

(71) Applicant: Central Glass Company, Limited, Ube, Yamaguchi (JP)

(72) Inventors: Mikihiro Takahashi, Ube (JP); Takayoshi Morinaka, Ube (JP); Masutaka Shinmen, Ube (JP); Kenta Yamamoto, Ube (JP); Wataru Kawabata, Ube (JP); Makoto Kubo, Ube (JP); Masataka Fujimoto, Ube (JP); Hiroki Matsuzaki, Ube (JP); Shoichi Tsujioka, Tokyo (JP)

(73) Assignee: Central Glass Co., Ltd., Ube (JP)

( * ) Notice: Subject to any disclaimer, the term of this patent is extended or adjusted under 35 U.S.C. 154(b) by 252 days.

(21) Appl. No.: 15/323,135

(22) PCT Filed: Jun. 30, 2015

(86) PCT No.: PCT/JP2015/068813
§ 371 (c)(1),
(2) Date: Mar. 10, 2017

(87) PCT Pub. No.: WO2016/002774
PCT Pub. Date: Jan. 7, 2016

(65) Prior Publication Data
US 2017/0204124 A1    Jul. 20, 2017

(30) Foreign Application Priority Data

Jul. 2, 2014 (JP) .................................. 2014-136867
Jun. 30, 2015 (JP) .................................. 2015-130613

(51) Int. Cl.
*H01M 6/16* (2006.01)
*H01M 10/052* (2010.01)
(Continued)

(52) U.S. Cl.
CPC ............ *H01M 6/168* (2013.01); *C07F 5/022* (2013.01); *C07F 5/069* (2013.01); *C07F 7/025* (2013.01);
(Continued)

(58) Field of Classification Search
None
See application file for complete search history.

(56) References Cited

U.S. PATENT DOCUMENTS 5,626,981 A    5/1997 Simon et al.
6,783,896 B2   8/2004 Tsujioka et al.
(Continued)

FOREIGN PATENT DOCUMENTS

JP    7-176323 A    7/1995
JP    2002-329528 A    11/2002
(Continued)

OTHER PUBLICATIONS

Machine-assisted English translation for JP 2014-194870 (provided by JPO). (Year: 2014).*
(Continued)

*Primary Examiner* — Sin J Lee
(74) *Attorney, Agent, or Firm* — Crowell & Moring LLP

(57) ABSTRACT

To provide a material suitable for a nonaqueous electrolyte battery having high-temperature durability. An ionic complex of the present invention is represented by any of the following formulae (1) to (3). For example, in the formula (1), A is a metal ion, a proton, or an onium ion; M is any of groups 13 to 15 elements. $R^1$ represents a $C_1$ to $C_{10}$ hydrocarbon group which may have a ring, a heteroatom, or a halogen atom, or $—N(R^2)—$. $R^2$ at this time represents hydrogen atom, alkali metal atom, a $C_1$ to $C_{10}$ hydrocarbon group which may have a ring, a heteroatom, or a halogen atom. $R^2$ can also have a branched chain or a ring structure when the number of carbon atoms is 3 or more. Y is carbon atom or sulfur atom. a, o, n, p, q, and r are each predetermined integers.

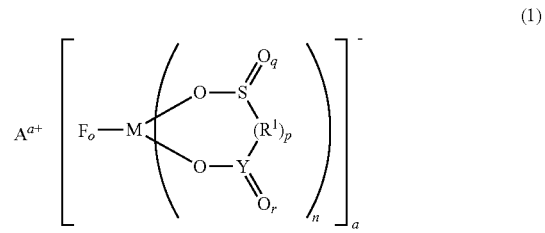

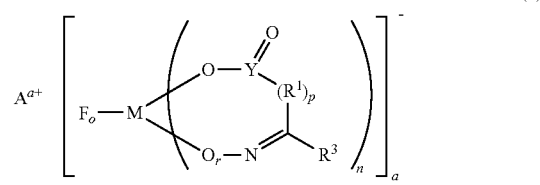

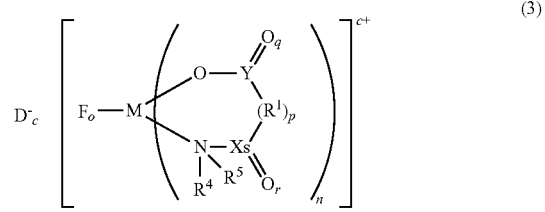

29 Claims, No Drawings

(51) Int. Cl.

| | |
|---|---|
| *H01M 10/0567* | (2010.01) |
| *H01M 10/0568* | (2010.01) |
| *H01M 10/0569* | (2010.01) |
| *H01M 4/38* | (2006.01) |
| *H01M 4/505* | (2010.01) |
| *H01M 4/525* | (2010.01) |
| *H01M 4/58* | (2010.01) |
| *H01M 4/587* | (2010.01) |
| *C07F 9/6584* | (2006.01) |
| *C07F 9/6574* | (2006.01) |
| *C07F 9/80* | (2006.01) |
| *C07F 9/26* | (2006.01) |
| *C07F 5/02* | (2006.01) |
| *C07F 5/06* | (2006.01) |
| *C07F 7/02* | (2006.01) |

(52) U.S. Cl.
CPC ............. *C07F 9/26* (2013.01); *C07F 9/6584* (2013.01); *C07F 9/65742* (2013.01); *C07F 9/65844* (2013.01); *C07F 9/80* (2013.01); *H01M 4/386* (2013.01); *H01M 4/505* (2013.01); *H01M 4/525* (2013.01); *H01M 4/587* (2013.01); *H01M 4/5825* (2013.01); *H01M 6/164* (2013.01); *H01M 6/166* (2013.01); *H01M 10/052* (2013.01); *H01M 10/0567* (2013.01); *H01M 10/0568* (2013.01); *H01M 10/0569* (2013.01); *H01M 2220/20* (2013.01); *H01M 2300/0037* (2013.01); *Y02T 10/7011* (2013.01)

(56) References Cited

U.S. PATENT DOCUMENTS

| | | | |
|---|---|---|---|
| 8,563,761 B2 | 10/2013 | Armand et al. | |
| 2011/0136019 A1* | 6/2011 | Amiruddin | H01M 10/0567 429/332 |
| 2011/0171112 A1 | 7/2011 | Armand et al. | |
| 2013/0183580 A1* | 7/2013 | Kako | H01M 4/1391 429/206 |

FOREIGN PATENT DOCUMENTS

| | | | |
|---|---|---|---|
| JP | 3573521 B2 | 10/2004 | |
| JP | 3722685 B2 | 11/2005 | |
| JP | 2010-123265 A | 6/2010 | |
| JP | 2014-194870 A | 10/2014 | |
| WO | WO 2009/122044 A2 | 10/2009 | |
| WO | WO-2016002771 A1 * | 1/2016 | ............ C01B 25/10 |
| WO | WO 2017/057968 A1 | 4/2017 | |

OTHER PUBLICATIONS

Machine-assisted English translation for WO 2016/002771 A1. (Year: 2016).*
Partial Supplementary European Search Report issued in counterpart European Patent Application No. 15814907.0 dated Jan. 3, 2018 (Eleven (11) pages).
International Search Report (PCT/ISA/210) issued in PCT Application No. PCT/JP2015/068813 dated Sep. 15, 2015 with English translation (6 pages).
Japanese-language Written Opinion (PCT/ISA/237) issued in PCT Application No. PCT/JP2015/068813 dated Sep. 15, 2015 with partial English translation (8 pages).
Il'in, E.G. et al., "Reactions of Phosphorus and Tantalum Pentafluorides with Picolinic Acid", Doklady Akademii Nauk SSSR, 1985, vol. 283, No. 4, pp. 904-907.
Kaukorat et al., "Unusual Formation of a $\lambda^6$P-Tetrafluorophosphate Involving Intramolecular Donor-Acceptor Interation; X-ray Crystal Structure Analysis and Temperature-Dependent NMR-Spectra", Heteroatom Chemistry, 1991, vol. 2, No. 1, pp. 81-86.
Krebs et al., "Reactions of Florophosphoranes with 8-Trimethylsiloxyquinoline and with 2-(n,N-Dimethylamino) Acetoxytrimethylsilane; X-Ray Crystal Structure of 2-(N, N-Dimethylamino) Acetoxyphenyltrifluorophosphate, $Me_2NCH_2C(:O)OP(Ph)F_3$*", Pioyhedron, 1989, vol. 8, No. 6, pp. 731-738.
Barluenga et al., "Cyclic $BF_2$ Adducts of Functionalized Fischer Vinylcarbene Complexes: Preparation and Stereoselective Diels-Alder Reactions with 2-Amino 1,3- Dienes", J. Am. Chem. Soc., 1998, vol. 120, pp. 2514-2522.
Vorkonkov et al., "The Synthesis and Structure of Bis(Pyridine-2-Carboxy) Difluoro ($\lambda^6$)- and Bis(Pyridine-2-Carboxy) fluorophenyl ($\lambda^5$) Siliconium", Arkivoc, 2011, pp. 163-172.

* cited by examiner

IONIC COMPLEX, ELECTROLYTE FOR NONAQUEOUS ELECTROLYTE BATTERY, NONAQUEOUS ELECTROLYTE BATTERY AND IONIC COMPLEX SYNTHESIS METHOD

TECHNICAL FIELD

The present invention relates to an ionic complex, an electrolyte for a nonaqueous electrolyte battery, a nonaqueous electrolyte battery, and an ionic complex synthesis method.

BACKGROUND ART

In batteries as electrochemical devices, in recent years, much attention has been paid to storage systems to be used for small-size and high energy density applications, for example, information-related apparatus, communication apparatus, that is, personal computer, video cameras, digital cameras, portable telephones, and smartphones, and storage systems for large-size power, for example, for electric vehicles, hybrid vehicles, fuel cell vehicle auxiliary power, and electric power storages. One example of candidate of the battery includes a nonaqueous electrolyte battery such as a lithium ion battery, a lithium battery, a lithium ion capacitor, and the like.

When a battery is a lithium ion battery, when a lithium cation is introduced into a negative electrode at the time of initial charging, the negative electrode and the lithium cation, or the negative electrode and an electrolyte solvent are reacted with each other to form a coating including lithium carbonate and lithium oxide as a main component on the surface of the negative electrode. The coating on the electrode surface is called Solid Electrolyte Interface (SEI), and the property thereof give a large influence on the battery characteristics.

In order to improve battery characteristics including durability, it is important to form a stable SEI having high lithium ion conductivity and low electronic conductivity. An attempt to form excellent SEI is actively carried out by adding a small amount (usually 0.01 mass % or more and 10 mass % or less) of a compound called an additive agent into an electrolyte.

For example, Patent Document 1 uses vinylene carbonate, Patent Document 2 uses unsaturated cyclic sulfonic acid, Patent Document 3 uses carbon dioxide, and Patent Document 4 uses lithium tetrafluorooxalatophosphate, respectively, as an additive agent for forming effective SEI.

Patent Document 1: Japanese Patent No. 3573521
Patent Document 2: Japanese Unexamined Patent Application, Publication No. 2002-329528
Patent Document 3: Japanese Unexamined Patent Application, Publication No. H7-176323
Patent Document 4: Japanese Patent No. 3722685

DISCLOSURE OF THE INVENTION

Problems to be Solved by the Invention

However, even in the aspect described in Patent Documents 1 to 4, deterioration may occur at 45° C. or more, there is still room for improvement in the case of use in places at high temperature for a long period, for example, use in vehicles.

The present invention has an object to provide a material suitable for use in a nonaqueous electrolyte battery having more excellent high-temperature durability.

Means for Solving the Problems

The present inventors thoroughly studied in order to achieve the above-mentioned object. As a result, they found that ionic complexes having predetermined chemical structures contribute to high-temperature durability of a nonaqueous electrolyte battery, thereby arriving at completion of the present invention. Specifically, the present invention provides the following.

[1] An ionic complex having a chemical structure represented by the following general formula (1).

[Chem. 1]

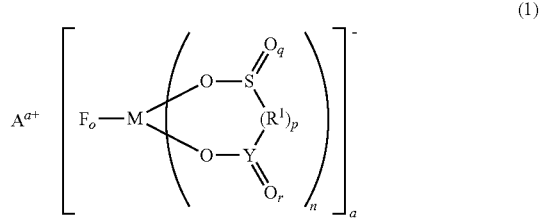

(1)

(In the general formula (1),

A is at least one selected from the group consisting of a metal ion, a proton, and an onium ion;

F is fluorine atom;

M is at least one selected from the group consisting of a Group 13 element (Al, and B), a group 14 element (Si) and a group 15 element (P, As, and Sb);

O is oxygen atom;

S is sulfur atom.

$R^1$ represents a hydrocarbon group which may have a ring, a heteroatom, or a halogen atom, the hydrocarbon group having 1 to 10 carbon atoms ($R^1$ can also have a branched chain or a ring structure when a number of carbon atoms is 3 or more), or —N($R^2$)—. $R^2$ at this time represents hydrogen atom, alkali metal atom, a hydrocarbon group which may have a ring, a heteroatom, or a halogen atom, the hydrocarbon group having 1 to 10 carbon atoms. $R^2$ can also have a branched chain or a ring structure when the number of carbon atoms is 3 or more.

Y is carbon atom or sulfur atom. When Y is carbon atom, r is 1. When Y is sulfur atom, r is 1 or 2.

a is 1 or 2, o is 2 or 4, n is 1 or 2, p is 0 or 1, q is 1 or 2, and r is 0, 1 or 2. When p is 0, a direct bond is formed between S and Y.)

[2] Furthermore, the present invention is the ionic complex described in [1], wherein an anion part of the formula (1) is at least one selected from the group consisting of the following 1Bb and 1Bd.

[Chem. 2]

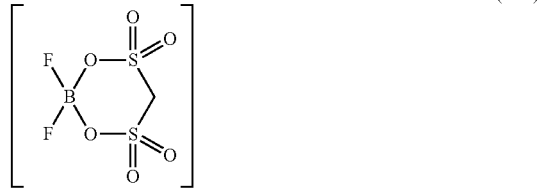

(1Bb)

-continued

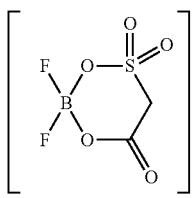
(1Bd)

[3] Furthermore, the present invention is the ionic complex described in [1] or [2], wherein the $A^{a+}$ is any one cation selected from the group consisting of a Li ion, a Na ion, a K ion, or a quaternary alkyl ammonium ion.

[4] Furthermore, the present invention is an ionic complex having a chemical structure represented by the following general formula (2).

[Chem. 3]

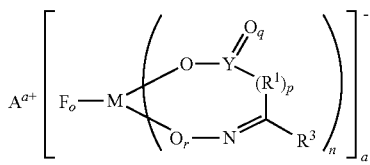
(2)

(In the general formula (2),

A is at least one selected from the group consisting of a metal ion, a proton, and an onium ion;

F is fluorine atom;

M is at least one selected from the group consisting of a group 13 element (Al, and B), a group 14 element (Si) and a group 15 element (P, As, and Sb);

O is oxygen atom;

N is nitrogen atom.

Y is carbon atom or sulfur atom, wherein when Y is carbon atom, q is 1, and when Y is sulfur atom, q is 1 or 2.

$R^1$ represents a hydrocarbon group which may have a ring, a heteroatom, or a halogen atom, the hydrocarbon group having 1 to 10 carbon atoms ($R^2$ may have a branched chain or a ring structure when a number of carbon atoms is 3 or more), or —N($R^2$)—. $R^2$ at this time represents hydrogen atom, alkali metal atom, a hydrocarbon group which may have a ring, a heteroatom, or a halogen atom, the hydrocarbon group having 1 to 10 carbon atoms. $R^2$ can also have a branched chain or a ring structure when the number of carbon atoms is 3 or more.

$R^3$ represents hydrogen atom, a hydrocarbon group which may have a ring, a heteroatom, or a halogen atom, the hydrocarbon group having 1 to 10 carbon atoms ($R^3$ can also have a branched chain or a ring structure when the number of carbon atoms is 3 or more), or —N($R^2$)—. $R^2$ at this time represents hydrogen atom, alkali metal atom, a hydrocarbon group which may have a ring, a heteroatom, or a halogen atom, the hydrocarbon group having 1 to 10 carbon atoms. $R^2$ can also have a branched chain or a ring structure when the number of carbon atoms is 3 or more.

a is 1 or 2, o is 2 or 4, n is 1 or 2, p is 0 or 1, q is 1 or 2, and r is 0 or 1. When p is 0, atoms positioned at both adjacent sides to $R^1$ (i.e., Y and a carbon atom) form a direct bond. When r is 0, a direct bond is formed between M and N.

[5] Furthermore, the present invention is the ionic complex described in [4], wherein an anion part of the general formula (2) is at least one selected from the group consisting of the following 2Pa, 2Pc, 2Ba, and 2Bc.

[Chem. 4]

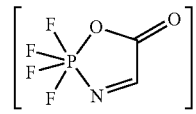
(2Pa)

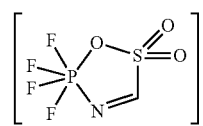
(2Pc)

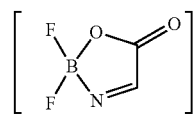
(2Ba)

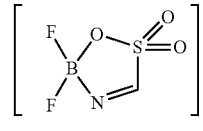
(2Bc)

[6] Furthermore, the present invention is the ionic complex described in [4] or [5], wherein the $A^{a+}$ is any one cation selected from the group consisting of a Li ion, a Na ion, a K ion, or a quaternary alkyl ammonium ion.

[7] Furthermore, the present invention is an ionic complex having a chemical structure represented by the following general formula (3).

[Chem. 5]

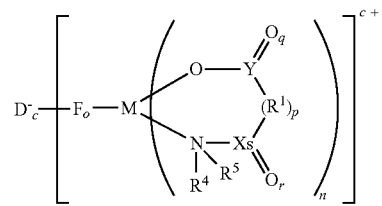
(3)

(In the general formula (3),

D is at least one selected from a halogen ion, a hexafluorophosphate anion, a tetrafluoroborate anion, a bis(trifluoromethane sulfonyl)imide anion, a bis(fluorosulfonyl)imide anion, a (fluorosulfonyl) (trifluoromethane sulfonyl)imide anion, and a bis(difluorophosphonyl)imide anion;

F is fluorine atom;

M is any one selected from the group consisting of a group 13 element (Al, and B), a group 14 element (Si) and a group 15 element (P, As, and Sb);

O is oxygen atom; and

N is nitrogen atom. Y is carbon atom or sulfur atom, wherein when Y is carbon atom, q is 1, and when Y is sulfur atom, q is 1 or 2.

X is carbon atom or sulfur atom, wherein when X is carbon atom, r is 1, and when X is sulfur atom, r is 1 or 2.

$R^1$ represents a hydrocarbon group which may have a ring, a heteroatom, or a halogen atom, the hydrocarbon group having 1 to 10 carbon atoms ($R^1$ may have a branched chain or a ring structure when the number of carbon atoms is 3 or more), or —N($R^2$)—. $R^2$ at this time represents hydrogen atom, alkali metal atom, a hydrocarbon group which may have a ring, a heteroatom, or a halogen atom, the hydrocarbon group having 1 to 10 carbon atoms. $R^2$ can also have a branched chain or a ring structure when the number of carbon atoms is 3 or more.

$R^4$ and $R^5$ each independently represents a hydrocarbon group which may have a ring, a heteroatom, or a halogen atom, the hydrocarbon group having 1 to 10 carbon atoms. $R^4$ and $R^5$ can also have a branched chain or a ring structure when a number of carbon atoms is 3 or more. Furthermore, as in the following general formula (4), $R^4$ and $R^5$ may also have a ring structures including each other.

[Chem. 6]

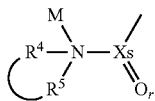

(4)

c is 0 or 1. When n is 1, c is 0 (when c is 0, D is absent). When n is 2, c is 1.

o is 2 or 4, n is 1 or 2, p is 0 or 1, q is 1 or 2, r is 1 or 2, and s is 0 or 1. When p is 0, a direct bond is formed between Y and X.

When s is 0, N($R^4$)($R^5$) and $R^1$ are directly bonded to each other, and, at that time, can also have structures of the following (5) to (8). In (6) and (8), wherein the direct bond is a double bond, $R^5$ is absent. As shown in (7), a structure in which the double bond is out of the ring may also be taken. $R^6$ and $R^7$ in this case each independently represents hydrogen atom, a hydrocarbon group which may have a ring, a heteroatom, or a halogen atom, the hydrocarbon group having 1 to 10 carbon atoms. When the number of carbon atoms is 3 or more, $R^6$ and $R^7$ can also have a branched chain or a ring structure.)

[Chem. 7]

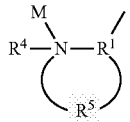

(5)

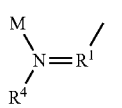

(6)

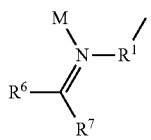

(7)

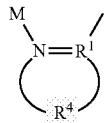

(8)

[8] Furthermore, the present invention is the ionic complex described in [7], wherein the ionic complex represented by the general formula (3) is any one selected from the group consisting of the following 3Pa, 3Pb, 3Pd, 3Pg, 3Ba, 3Bb, 3Bf, 3Bg, and 3Bi.

[Chem. 8]

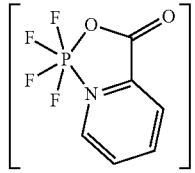

(3Pa)

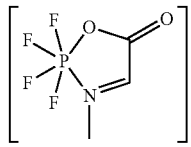

(3Pb)

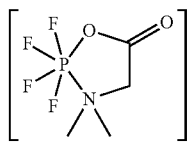

(3Pd)

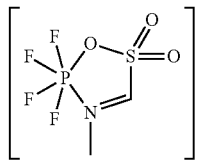

(3Pg)

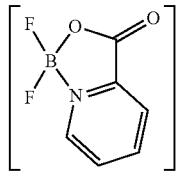

(3Ba)

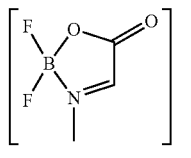

(3Bb)

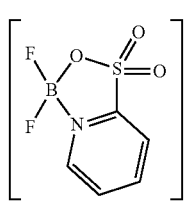

(3Bf)

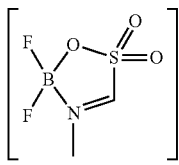

(3Bg)

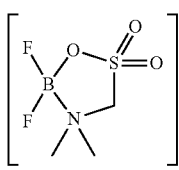

(3Bi)

[9] Furthermore, the present invention is the ionic complex described in [7] or [8], wherein the $D^-$ is at least one anion selected from the group consisting of a hexafluorophosphate anion, a tetrafluoroborate anion, a bis(trifluoromethane sulfonyl)imide anion, a bis(fluorosulfonyl)imide anion, a (fluorosulfonyl) (trifluoromethane sulfonyl)imide anion, and a bis(difluorophosphonyl)imide anion.

[10] Furthermore, the present invention is the ionic complex described in any one of [1] to [9], wherein the M is B or P.

[11] Furthermore, the present invention is an electrolyte for a nonaqueous electrolyte battery, containing an ionic complex according to any one of [1] to [10].

[12] Furthermore, the present invention is an electrolyte for a nonaqueous electrolyte battery containing a solute, an ionic complex according to any one of [1] to [10], and nonaqueous organic solvent.

[13] Furthermore, the present invention is an electrolyte for a nonaqueous electrolyte battery described in [12], wherein the solute is a salt comprising a pair of at least one cation selected from the group consisting of an alkali metal ion, an alkaline earth metal ion, and quaternary ammonium, and at least one anion selected from the group consisting of anions of hexafluorophosphate, tetrafluoroborate, perchlorate, hexafluoroarsenate, hexafluoroantimonate, trifluoromethanesulfonate, bis(trifluoromethane sulfonyl)imide, bis(pentafluoroethane sulfonyl)imide, (trifluoromethane sulfonyl) (pentafluoroethane sulfonyl)imide, bis(fluorosulfonyl)imide, (trifluoromethane sulfonyl) (fluorosulfonyl)imide, (pentafluoroethane sulfonyl) (fluorosulfonyl)imide, tris (trifluoromethane sulfonyl)methide, and bis (difluorophosphonyl)imide.

[14] Furthermore, the present invention is the electrolyte for a nonaqueous electrolyte battery described in [12] or [13], wherein the nonaqueous organic solvent is at least one selected from the group consisting of carbonates, esters, ethers, lactones, nitriles, imides, and sulfones.

[15] Furthermore, the present invention is the electrolyte for a nonaqueous electrolyte battery described in any one of [12] to [14], wherein the nonaqueous organic solvent is at least one selected from the group consisting of ethyl methyl carbonate, dimethyl carbonate, diethyl carbonate, methyl propyl carbonate, ethyl propyl carbonate, methyl butyl carbonate, ethylene carbonate, propylene carbonate, butylene carbonate, methyl acetate, methyl propionate, ethyl propionate, diethyl ether, acetonitrile, propionitrile, tetrahydrofuran, 2-methyltetrahydrofuran, furan, tetrahydropyran, 1,3-dioxane, 1,4-dioxane, dibutyl ether, diisopropyl ether, 1,2-dimethoxyethane, N,N-dimethylformamide, dimethylsulfoxide, sulfolane, γ-butyrolactone, and γ-valerolactone.

[16] Furthermore, the present invention is the electrolyte for a nonaqueous electrolyte battery described in [12] or [13], wherein the nonaqueous organic solvent contains at least one selected from the group consisting of cyclic carbonate and chain carbonate.

[17] Furthermore, the present invention is the electrolyte for a nonaqueous electrolyte battery described in [16], wherein the cyclic carbonate is at least one selected from the group consisting of ethylene carbonate, propylene carbonate, and butylene carbonate; and the chain carbonate is at least one selected from the group consisting of ethyl methyl carbonate, dimethyl carbonate, diethyl carbonate, methyl propyl carbonate, ethyl propyl carbonate, and methyl butyl carbonate.

[18] Furthermore, the present invention is the electrolyte for a nonaqueous electrolyte battery described in any one of [11] to [17], wherein an addition concentration of the ionic complex is in a range from 0.001 to 20 mass % with respect to a total amount of the solute, the nonaqueous organic solvent, and the ionic complex.

[19] Furthermore, the present invention is the electrolyte for a nonaqueous electrolyte battery described in any one of [11] to [18], further containing at least one second compound selected from the group consisting of fluorine-containing compounds represented by the following general formulae (9) to (16).

[Chem. 9]

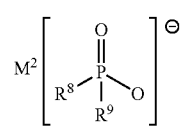

(9)

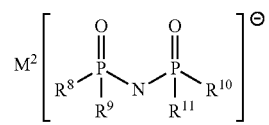

(10)

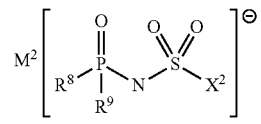

(11)

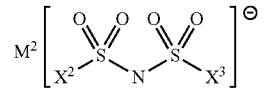

(12)

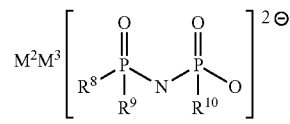

(13)

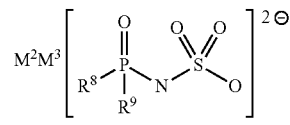

(14)

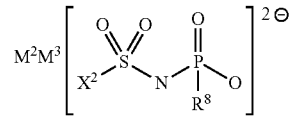

(15)

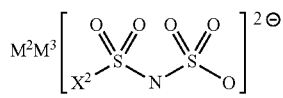
(16)

[In the general formulae (9) to (11) and (13) to (15), $R^8$ to $R^{11}$ each independently represents a fluorine atom and an organic group selected from a straight chain or branched alkoxy group having 1 to 10 carbon atoms, an alkenyloxy group having 2 to 10 carbon atoms, an alkynyloxy group having 2 to 10 carbon atoms, a cycloalkoxy group and a cycloalkenyloxy group having 3 to 10 carbon atoms, and an aryloxy group having 6 to 10 carbon atoms, and the organic group can include a fluorine atom, an oxygen atom, and an unsaturated bond. In the general formulae (11), (12), (15), and (16), $X^2$ and $X^3$ each independently represents a fluorine atom and an organic group selected from a straight chain or branched alkyl group having 1 to 10 carbon atoms, an alkenyl group having 2 to 10 carbon atoms, an alkynyl group having 2 to 10 carbon atoms, a cycloalkyl group and a cycloalkenyl group having 3 to 10 carbon atoms, an aryl group having 6 to 10 carbon atoms, a straight chain or branched alkoxy group having 1 to 10 carbon atoms, an alkenyloxy group having 2 to 10 carbon atoms, an alkynyloxy group having 2 to 10 carbon atoms, a cycloalkoxy group and a cycloalkenyloxy group having 3 to 10 carbon atoms, and an aryloxy group having 6 to 10 carbon atoms, and the organic group also can include a fluorine atom, an oxygen atom, and an unsaturated bond. Furthermore, the general formulae (9) to (16) include at least one bond selected from a P—F bond and an S—F bond. $M^2$ and $M^3$ each independently represents a proton, a metal cation, or an onium cation.

[20] Furthermore, the present invention is the electrolyte for a nonaqueous electrolyte battery described in [19], wherein $R^8$ to $R^{11}$ of the general formulae (9) to (11) and (13) to (15) are a fluorine atom and an organic group selected from the group consisting of a straight chain or branched alkoxy group including a fluorine atom having 1 to 10 carbon atoms, an alkenyloxy group having 2 to 10 carbon atoms, and an alkynyloxy group having 2 to 10 carbon atoms.

[21] Furthermore, the present invention is the electrolyte for a nonaqueous electrolyte battery described in [20], wherein the alkoxy group is selected from the group consisting of a 2,2,2-trifluoroethoxy group, a 2,2,3,3-tetrafluoropropoxy group, a 1,1,1-trifluoroisopropoxy group, and a 1,1,1,3,3,3-hexafluoroisopropoxy group; the alkenyloxy group is selected from the group consisting of 1-propenyloxy group, 2-propenyloxy group, and 3-butenyloxy group; and the alkynyloxy group is selected from the group consisting of 2-propynyloxy group, and 1,1-dimethyl-2-propynyloxy group.

[22] Furthermore, the present invention is the electrolyte for a nonaqueous electrolyte battery described in any one of [19] to [21], wherein $X^2$ and $X^3$ of the general formulae (11), (12), (15), and (16) are a fluorine atom and an organic group selected from the group consisting of a straight chain or branched alkoxy group having 1 to 10 carbon atoms, an alkenyloxy group having 2 to 10 carbon atoms, and an alkynyloxy group having 2 to 10 carbon atoms.

[23] Furthermore, the present invention is the electrolyte for a nonaqueous electrolyte battery described in [22], wherein the alkoxy group is selected from the group consisting of a methoxy group, an ethoxy group, and a propoxy group; the alkenyloxy group is selected from the group consisting of a 1-propenyloxy group, a 2-propenyloxy group, and a 3-butenyloxy group; and the alkynyloxy group is selected from the group consisting of a 2-propynyloxy group, and a 1,1-dimethyl-2-propynyloxy group.

[24] Furthermore, the present invention is an electrolyte for a nonaqueous electrolyte battery described in any one of [19] to [23], wherein $M^2$ and $M^3$ of the general formulae (9) to (16) are at least one cation selected from the group consisting of a lithium ion, a sodium ion, a potassium ion, a tetraalkyl ammonium ion, and tetraalkyl phosphonium ion.

[25] Furthermore, the present invention is the electrolyte for a nonaqueous electrolyte battery described in any one of [19] to [24], wherein an addition concentration of the second compound is in a range from 0.001 to 10.0 mass % with respect to a total amount of the solute, the nonaqueous organic solvent, the ionic complex, and the second compound.

[26] Furthermore, the present invention is the electrolyte for a nonaqueous electrolyte battery described in any one of [11] to [25], further containing at least one third compound represented by the following general formula (17).

[In the general formula (17), $R^{12}$ each independently represents a group having an unsaturated carbon-carbon bond. $R^{13}$ each independently represents a fluorine atom and a group selected from the group consisting of an alkyl group, an alkoxy group, an alkenyl group, an alkenyloxy group, an alkynyl group, an alkynyloxy group, an aryl group, and an aryloxy group, and these groups may include a fluorine atom and/or an oxygen atom. x is 2 to 4.]

[27] Furthermore, the present invention is an electrolyte for a nonaqueous electrolyte battery described in [26], wherein a group represented by $R^{12}$ of the general formula (17) each independently represents a group selected from the group consisting of a vinyl group, an allyl group, a 1-propenyl group, an ethynyl group, and a 2-propynyl group.

[28] Furthermore, the present invention is an electrolyte for a nonaqueous electrolyte battery described in [26] or [27], wherein a group represented by $R^{13}$ of the general formula (17) each independently represents a fluorine atom and a group selected from the group consisting of a methyl group, an ethyl group, a propyl group, a 2,2,2-trifluoroethyl group, a 2,2,3,3-tetrafluoropropyl group, a 1,1,1-trifluoroisopropyl group, a 1,1,1,3,3,3-hexafluoroisopropyl group, a 2,2,2-trifluoroethoxy group, a 2,2,3,3-tetrafluoropropoxy group, a 2,2,3,3,3-pentafluoropropoxy group, a 1,1,1-trifluoroisopropoxy group, and a 1,1,1,3,3,3-hexafluoroisopropoxy group.

[29] Furthermore, the present invention is an electrolyte for a nonaqueous electrolyte battery described in any one of [26] to [28], wherein x in the general formula (17) is 2 to 3.

[30] Furthermore, the present invention is an electrolyte for a nonaqueous electrolyte battery described in any one of [26] to [29], wherein an addition concentration of the third compound with respect to a total amount of the solute, the nonaqueous organic solvent, the ionic complex, and the third compound is in a range from 0.005 to 7.0 mass %.

[31] Furthermore, the present invention is an electrolyte for a nonaqueous electrolyte battery described in any one of [11] to [30], further containing a fourth compound that is at least one selected from the group consisting of a cyclic sulfonic acid compound represented by the following general formulae (18), (19), and (20), 1,3-propane sultone (hereinafter, referred to as "PS"), and 1,2-pentanediol sulfate ester (hereinafter, referred to as "PEGLST").

[Chem. 10]

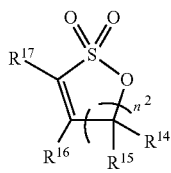

(18)

(In the formula (18), O is an oxygen atom; S is a sulfur atom; $n^2$ is an integer of 1 or more and 3 or less. $R^{14}$, $R^{15}$, $R^{16}$, and $R^{17}$ each independently represents a hydrogen atom, a substituted or non-substituted alkyl group having 1 or more and 5 or less carbon atoms, or a substituted or non-substituted fluoroalkyl group having 1 or more and 4 or less carbon atoms.)

[Chem. 11]

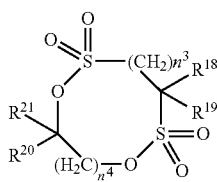

(19)

(In the formula (19), O is an oxygen atom; S is a sulfur atom; $n^3$ is an integer of 0 or more and 4 or less; $R^{18}$ and $R^{19}$ each independently represents a hydrogen atom, a halogen atom, or a substituted or non-substituted alkyl group having 1 or more and 5 or less carbon atoms; and $R^{20}$ and $R^{21}$ each independently represents a hydrogen atom, a halogen atom, a substituted or non-substituted alkyl group having 1 to 5 carbon atoms, or substituted or non-substituted fluoroalkyl group having 1 or more and 4 or less carbon atoms, and $n^4$ is an integer of 0 or more and 4 or less.)

[Chem. 12]

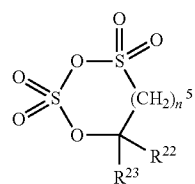

(20)

(In the formula (20), O is an oxygen atom; S is a sulfur atom; $n^5$ is an integer of 0 to 3; and $R^{22}$ and $R^{23}$ each independently represents a hydrogen atom, a halogen atom, a substituted or non-substituted alkyl group having 1 or more and 5 or less carbon atoms, or a substituted or non-substituted fluoroalkyl group having 1 or more and 4 or less carbon atoms.

[32] Furthermore, the present invention is the electrolyte for a nonaqueous electrolyte battery described in [31], wherein an addition concentration of the fourth compound is in a range from 0.001 to 10 mass % with respect to a total amount of a solute, a nonaqueous organic solvent, an ionic complex, and the fourth compound.

[33] Furthermore, the present invention is the electrolyte for a nonaqueous electrolyte battery described in any one of [11] to [32], further containing a fifth compound that is at least one selected from the group consisting of a cyclic carbonate compound represented by the following general formula (21).

[Chem. 13]

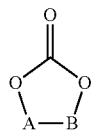

(21)

(In the formula (21), O is an oxygen atom, A is hydrocarbon having 10 or less carbon atoms and optionally including an unsaturated bond or a ring structure or a halogen atom, and B is hydrocarbon having 10 or less carbon atoms and optionally including an unsaturated bond or a ring structure or a halogen atom. Note here that a double bond may be formed between A and B.

[34] Furthermore, the present invention is an electrolyte for a nonaqueous electrolyte battery described in [33], wherein the addition concentration of the fifth compound is in a range from 0.001 to 10 mass % with respect to the total amount of the solute, the nonaqueous organic solvent, the ionic complex, and the fifth compound.

[35] Furthermore, the present invention is a nonaqueous electrolyte battery including a positive electrode; a negative electrode including lithium or a negative electrode material capable of absorbing/releasing lithium; and an electrolyte for a nonaqueous electrolyte battery described in any one of [11] to [34].

[36] Furthermore, the present invention is a nonaqueous electrolyte battery including a positive electrode; a negative electrode including sodium or a negative electrode material capable of absorbing/releasing sodium; and an electrolyte for a nonaqueous electrolyte battery described in any one of [11] to [34].

[37] Furthermore, the present invention is a method for synthesizing an ionic complex represented by the following general formula (1), (2) or (3), the method including a reaction step of reacting, in a solvent, any one of phosphorus pentafluoride and boron trifluoride with at least one selected from the group consisting of carbosulfonic acid or salt thereof, disulfonic acid or salt thereof, amino acid or salt thereof, amide carboxylic acid or salt thereof, diamide or salt thereof, aminosulfonic acid or salt thereof, imine acid or salt thereof, and imine sulfonic acid or salt thereof, in which a counter cation of an acid anion is at least one cation selected from the group consisting of a proton ion, an alkali metal ion, an alkaline earth metal ion, and quaternary ammonium. Note here that after the above-mentioned synthesis method, an operation for exchanging cations may be carried out.

[Chem. 14]

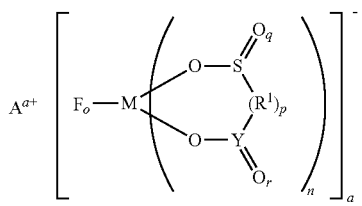

(1)

(In the general formula (1),

A is at least one selected from the group consisting of a metal ion, a proton, and an onium ion;

F is fluorine atom;

M is at least one selected from the group consisting of a group 13 element (Al, and B), a group 14 element (Si) and a group 15 element (P, As, and Sb), O is oxygen atom; and S is sulfur atom.

$R^1$ represents a hydrocarbon group which may have a ring, a heteroatom, or a halogen atom, the hydrocarbon group having 1 to 10 carbon atoms ($R^2$ can also have a branched chain or a ring structure when a number of carbon atoms is 3 or more), or —N($R^2$)—. $R^2$ at this time represents hydrogen atom, alkali metal atom, a hydrocarbon group which may have a ring, a heteroatom, or a halogen atom, the hydrocarbon group having 1 to 10 carbon atoms. $R^2$ can also have a branched chain or a ring structure when the number of carbon atoms is 3 or more.

Y is carbon atom or sulfur atom. When Y is carbon atom, r is 1. When Y is sulfur atom, r is 1 or 2.

a is 1 or 2, o is 2 or 4, n is 1 or 2, p is 0 or 1, q is 1 or 2, and r is 0, 1 or 2. When p is 0, a direct bond is formed between S and Y.)

[Chem. 15]

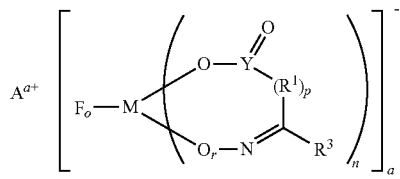

(2)

(In the general formula (2),

A is at least one selected from the group consisting of a metal ion, a proton, and an onium ion;

F is fluorine atom;

M is at least one selected from the group consisting of a group 13 element (Al, and B), a group 14 element (Si) and a group 15 element (P, As, and Sb);

O is oxygen atom;

N is nitrogen atom.

Y is carbon atom or sulfur atom, wherein when Y is carbon atom, q is 1, and when Y is sulfur atom, q is 1 or 2.

$R^1$ represents a hydrocarbon group which may have a ring, a heteroatom, or a halogen atom, the hydrocarbon group having 1 to 10 carbon atoms ($R^1$ may have a branched chain or a ring structure when a number of carbon atoms is 3 or more), or —N($R^2$)—. $R^2$ at this time represents hydrogen atom, alkali metal atom, a hydrocarbon group which may have a ring, a heteroatom, or a halogen atom, the hydrocarbon group having 1 to 10 carbon atoms. $R^2$ can also have a branched chain or a ring structure when the number of carbon atoms is 3 or more.

$R^3$ represents hydrogen atom, a hydrocarbon group which may have a ring, a heteroatom, or a halogen atom, the hydrocarbon group having 1 to 10 carbon atoms ($R^3$ can also have a branched chain or a ring structure when the number of carbon atoms is 3 or more), or —N($R^2$)—. $R^2$ at this time represents hydrogen atom, alkali metal atom, a hydrocarbon group which may have a ring, a heteroatom, or a halogen atom, the hydrocarbon group having 1 to 10 carbon atoms. $R^2$ can also have a branched chain or a ring structure when the number of carbon atoms is 3 or more.

a is 1 or 2, o is 2 or 4, n is 1 or 2, p is 0 or 1, q is 1 or 2, and r is 0 or 1. When p is 0, atoms positioned at both adjacent sides to $R^1$ (i.e., Y and a carbon atom) form a direct bond. When r is 0, a direct bond is formed between M and N.)

[Chem. 16]

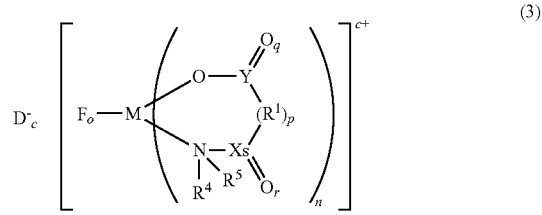

(3)

(In the general formula (3),

D is at least one selected from a halogen ion, a hexafluorophosphate anion, a tetrafluoroborate anion, a bis(trifluoromethane sulfonyl)imide anion, a bis(fluorosulfonyl)imide anion, a (fluorosulfonyl) (trifluoromethane sulfonyl)imide anion, and a bis(difluorophosphonyl)imide anion;

F is fluorine atom;

M is any one selected from the group consisting of a group 13 element (Al, and B), a group 14 element (Si) and a group 15 element (P, As, and Sb);

O is oxygen atom; and

N is nitrogen atom.

Y is carbon atom or sulfur atom, wherein when Y is carbon atom, q is 1, and when Y is sulfur atom, q is 1 or 2.

X is carbon atom or sulfur atom, wherein when X is carbon atom, r is 1, and when X is sulfur atom, r is 1 or 2.

$R^1$ represents a hydrocarbon group which may have a ring, a heteroatom, or a halogen atom, the hydrocarbon group having 1 to 10 carbon atoms ($R^2$ may have a branched chain or a ring structure when the number of carbon atoms is 3 or more), or —N($R^2$)—. $R^2$ at this time represents hydrogen atom, alkali metal atom, a hydrocarbon group which may have a ring, a heteroatom, or a halogen atom, the hydrocarbon group having 1 to 10 carbon atoms. $R^2$ can also have a branched chain or a ring structure when the number of carbon atoms is 3 or more.

$R^4$ and $R^5$ each independently represents a hydrocarbon group which may have a ring, a heteroatom, or a halogen atom, the hydrocarbon group having 1 to 10 carbon atoms, wherein $R^4$ and $R^5$ can also have a branched chain or a ring structure when a number of carbon atoms is 3 or more. Furthermore, as in the following general formula (4), $R^4$ and $R^5$ may also have a ring structures including each other.

[Chem. 17]

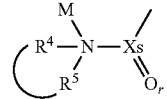

(4)

c is 0 or 1, wherein when n is 1, c is 0, in which when c is 0, D is absent, and when n is 2, c is 1.

o is 2 or 4, n is 1 or 2, p is 0 or 1, q is 1 or 2, r is 1 or 2, and s is 0 or 1. When p is 0, a direct bond is formed between Y and X.

When s is 0, N(R⁴)(R⁵) and R¹ are directly bonded to each other, and, at that time, can also have structures of the following (5) to (8). In (6) and (8), wherein the direct bond is a double bond, R⁵ is absent.

As shown in (7), a structure in which the double bond is out of the ring may also be taken. R⁶ and R⁷ in this case each independently represents hydrogen atom, a hydrocarbon group which may have a ring, a heteroatom, or a halogen atom, the hydrocarbon group having 1 to 10 carbon atoms, wherein when the number of carbon atoms is 3 or more, R⁶ and R⁷ can also have a branched chain or a ring structure.)

[Chem. 18]

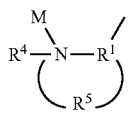

(5)

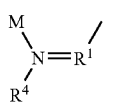

(6)

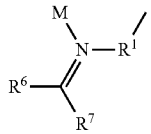

(7)

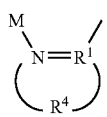

(8)

[38] Furthermore, the present invention is the method for synthesizing an ionic complex described in [37], wherein the solvent is at least one selected from the group consisting of ethyl methyl carbonate, dimethyl carbonate, diethyl carbonate, methyl propyl carbonate, ethyl propyl carbonate, methyl acetate, methyl propionate, diethyl ether, acetonitrile, tetrahydrofuran, 2-methyltetrahydrofuran, furan, tetrahydropyran, 1,3-dioxane, 1,4-dioxane, diisopropyl ether, and 1,2-dimethoxyethane.

[39] Furthermore, the present invention is the method for synthesizing an ionic complex described in [37] or [38], wherein an internal temperature during the reaction step is −40° C. or more and 120° C. or less, or −40° C. or more and not more than a boiling point of the solvent.

[40] Furthermore, the present invention is the method for synthesizing an ionic complex described in any one of [37] to [39], further including a purification step including adding sodium hexafluorophosphate to a solution including the ionic complex and 1 mass % or more lithium tetrafluoroborate, obtained after the reaction step, followed by precipitation and then filtration of a tetrafluoroborate anion as sodium tetrafluoroborate.

[41] Furthermore, the present invention is the method for synthesizing an ionic complex described in [40], wherein an addition amount of the sodium hexafluorophosphate is 0.8 molar equivalent or more and 1.2 molar equivalent or less with respect to the lithium tetrafluoroborate.

Effects of the Invention

The present invention can provide a material suitable to be used for a nonaqueous electrolyte battery having more excellent high-temperature durability.

PREFERRED MODE FOR CARRYING OUT THE INVENTION

Hereinafter, specific embodiments of the present invention are described in detail, but the present invention is not necessarily limited to the below-mentioned embodiments, and a embodiments can be appropriately modified within the scope of the object of the present invention.

Ionic Complex

An ionic complex of the present invention includes a compound represented by any one of the following general formulae (1) to (3).

[Chem. 19]

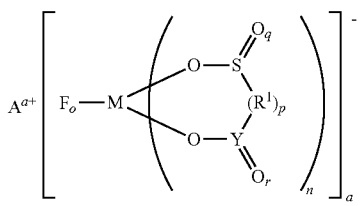

(1)

[Chem. 20]

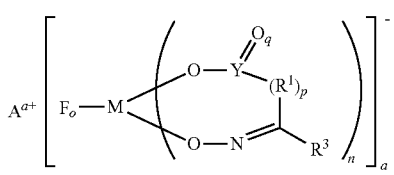

(2)

[Chem. 21]

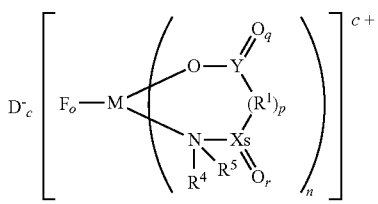

(3)

[General Formula (1)]

In the above-mentioned general formula (1), A is at least one selected from the group consisting of a metal ion, a proton, and an onium ion. Among them, from the viewpoint that the degree of ion dissociation is high, it is preferable that A is any one cation selected from the group consisting of a Li ion, a Na ion, a K ion, and a quaternary alkyl ammonium ion.

F is fluorine atom. M is at least one selected from the group consisting of a group 13 element (Al, and B), a group 14 element (Si) and a group 15 element (P, As, and Sb). Among them, in view of toxicity or easiness in synthesis, it is preferable that M is B or P.

O is oxygen atom, and S is sulfur atom.

R¹ represents a hydrocarbon group which may have a ring, a heteroatom, or a halogen atom, the hydrocarbon group having 1 to 10 carbon atoms (R¹ may have a branched chain or a ring structure when the number of carbon atoms is 3 or more), or —N(R²)—. R² at this time represents hydrogen atom, alkali metal atom, a hydrocarbon group which may have a ring, a heteroatom, or a halogen atom, the hydrocarbon group having 1 to 10 carbon atoms. R² can also have a branched chain or a ring structure when the number of carbon atoms is 3 or more.

Y is carbon atom or sulfur atom. When Y is carbon atom, r is 1. When Y is sulfur atom, r is 1 or 2.

a is 1 or 2, o is 2 or 4, n is 1 or 2, p is 0 or 1, q is 1 or 2, and r is 0, 1 or 2. When p is 0, a direct bond is formed between S and Y.

Specific examples of the ionic complex represented by the general formula (1) includes the following compounds.

[Chem. 22]

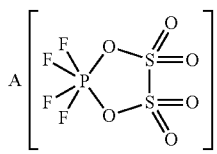

Among them, it is preferable that the ionic complex is at least one selected from the group consisting of the above-mentioned 1Bb and 1Bd from the viewpoint that use of it as a component of an electrolyte for a nonaqueous electrolyte battery enhances the cycle characteristics of the nonaqueous electrolyte battery.

[General Formula (2)]

In the above-mentioned general formula (2), A is at least one selected from the group consisting of a metal ion, a proton, and an onium ion. Among them, from the viewpoint that the degree of ion dissociation is high, it is preferable that A is any one cation selected from the group consisting of a Li ion, a Na ion, a K ion, and a quaternary alkyl ammonium ion.

F is fluorine atom. M is at least one selected from the group consisting of a group 13 element (Al, and B), a group 14 element (Si) and a group 15 element (P, As, and Sb). Among them, in view of toxicity or easiness in synthesis, it is preferable that M is B or P.

O is oxygen atom, and N is nitrogen atom.

Y is carbon atom or sulfur atom. When Y is carbon atom, q is 1. When Y is sulfur atom, q is 1 or 2.

R¹ represents a hydrocarbon group which may have a ring, a heteroatom, or a halogen atom, the hydrocarbon group having 1 to 10 carbon atoms (R¹ may have a branched chain or a ring structure when the number of carbon atoms is 3 or more), or —N(R²)—. R² at this time represents hydrogen atom, alkali metal atom, a hydrocarbon group which may have a ring, a heteroatom, or a halogen atom, the hydrocarbon group having 1 to 10 carbon atoms. R² can also have a branched chain or a ring structure when the number of carbon atoms is 3 or more.

$R^3$ represents hydrogen atom, a hydrocarbon group which may have a ring, a heteroatom, or a halogen atom, the hydrocarbon group having 1 to 10 carbon atoms ($R^3$ can also have a branched chain or a ring structure when the number of carbon atoms is 3 or more), or —N($R^2$)—. $R^2$ at this time represents hydrogen atom, alkali metal atom, a hydrocarbon group which may have a ring, a heteroatom, or a halogen atom, the hydrocarbon group having 1 to 10 carbon atoms. $R^2$ can also have a branched chain or a ring structure when the number of carbon atoms is 3 or more.

a is 1 or 2, o is 2 or 4, n is 1 or 2, p is 0 or 1, q is 1 or 2, and r is 0 or 1. When p is 0, atoms positioned at both adjacent sides to $R^1$ (i.e., Y and a carbon atom) form a direct bond. When r is 0, a direct bond is formed between M and N.

Specific examples of the ionic complex represented by the general formula (2) include the following compounds.

[Chem. 23]

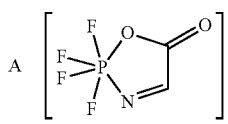
(2Pa)

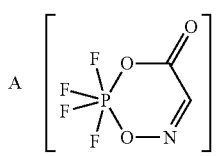
(2Pb)

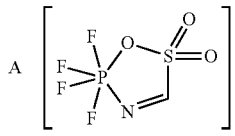
(2Pc)

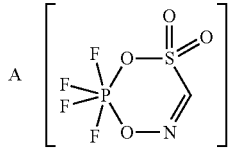
(2Pd)

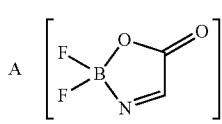
(2Ba)

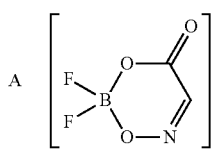
(2Bb)

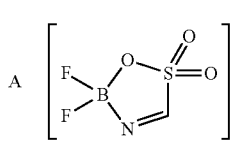
(2Bc)

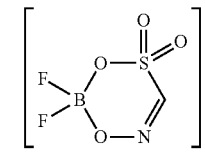
(2Bd)

Among them, it is preferable that the ionic complex is at least one selected from the group consisting of the above-mentioned 2Pa, 2Pc, 2Ba, and 2Bc from the viewpoint that use of it as a component of an electrolyte for a nonaqueous electrolyte battery enhances the cycle characteristics of the nonaqueous electrolyte battery.

[General Formula (3)]

In the above-mentioned general formula (3), D is at least one selected from a halogen ion, a hexafluorophosphate anion, a tetrafluoroborate anion, a bis(trifluoromethane sulfonyl)imide anion, a bis(fluorosulfonyl)imide anion, (trifluoromethane sulfonyl) (fluorosulfonyl)imide anion, and bis(difluorophosphonyl)imide anion. Among them, from the viewpoint that it does not give an adverse effect on the battery characteristics and it is available relatively easily, it is preferable that D is at least one selected from the group consisting of a hexafluorophosphate anion, a tetrafluoroborate anion, a bis(trifluoromethane sulfonyl)imide anion, a bis(fluorosulfonyl)imide anion, and a bis(difluorophosphonyl)imide anion.

F is fluorine atom. M is any one selected from the group consisting of a group 13 element (Al, and B), a group 14 element (Si) and a group 15 element (P, As, and Sb). Among them, in view of toxicity or easiness in synthesis, it is preferable that M is B or P.

O is oxygen atom, and N is nitrogen atom.

Y is carbon atom or sulfur atom. When Y is carbon atom, q is 1. When Y is sulfur atom, q is 1 or 2.

X is carbon atom or sulfur atom. When X is carbon atom, r is 1. When X is sulfur atom, r is 1 or 2.

$R^1$ represents a hydrocarbon group which may have a ring, a heteroatom, or a halogen atom, the hydrocarbon group having 1 to 10 carbon atoms ($R^1$ may have a branched chain or a ring structure when the number of carbon atoms is 3 or more), or —N($R^2$)—. $R^2$ at this time represents hydrogen atom, alkali metal atom, a hydrocarbon group which may have a ring, a heteroatom, or a halogen atom, the hydrocarbon group having 1 to 10 carbon atoms. $R^2$ may also have a branched chain or a ring structure when the number of carbon atoms is 3 or more.

$R^4$ and $R^5$ each independently represents a hydrocarbon group which may have a ring, a heteroatom, or a halogen atom, the hydrocarbon group having 1 to 10 carbon atoms. $R^4$ and $R^5$ can also have a branched chain or a ring structure when a number of carbon atoms is 3 or more. Furthermore, as in the following general formula (4), $R^4$ and $R^5$ may also have a ring structures including each other.

[Chem. 24]

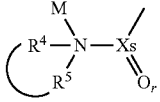
(4)

c is 0 or 1. When n is 1, c is 0 (when c is 0, D is absent). When n is 2, c is 1.

o is 2 or 4, n is 1 or 2, p is 0 or 1, q is 1 or 2, r is 1 or 2, and s is 0 or 1. When p is 0, a direct bond is formed between Y and X.

When s is 0, $N(R^4)(R^5)$ and $R^1$ are directly bonded to each other, and, at that time, can also have structures of the following (5) to (8). In (6) and (8), wherein the direct bond is a double bond, $R^5$ is absent. As shown in (7), a structure in which the double bond is out of the ring may also be taken. $R^6$ and $R^7$ in this case each independently represents hydrogen atom, a hydrocarbon group which may have a ring, a heteroatom, or a halogen atom, the hydrocarbon group having 1 to 10 carbon atoms. $R^6$ and $R^7$ can also have a branched chain or ring structure when the number of carbon atoms is 3 or more.)

[Chem. 25]

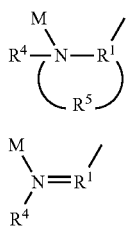

(5)

(6)

(7)

(8)

Specific examples of the ionic complex represented by the general formula (3) include the following compounds.

[Chem. 26]

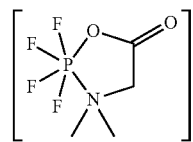
(3Pa)

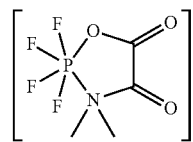
(3Pb)

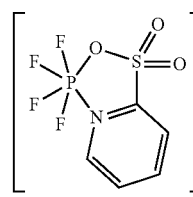
(3Pc)

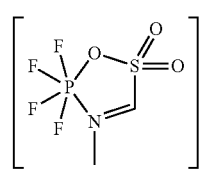
(3Pd)

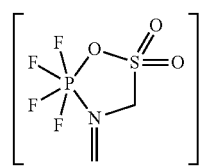
(3Pe)

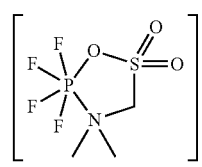
(3Pf)

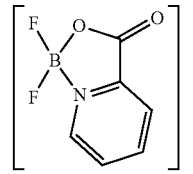
(3Pg)

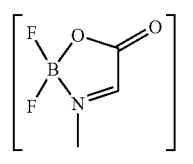
(3Ph)

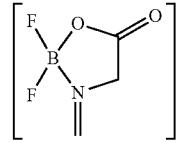
(3Pi)

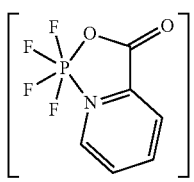
(3Ba)

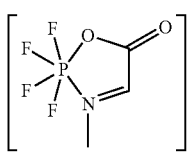
(3Bb)

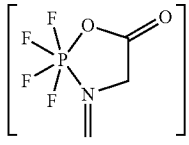
(3Bc)

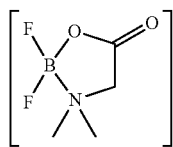

(3Bd)

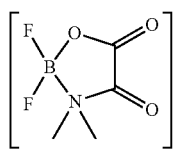

(3Be)

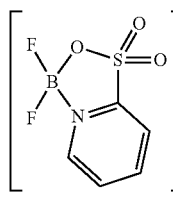

(3Bf)

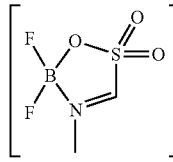

(3Bg)

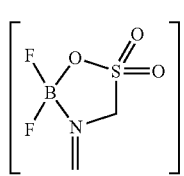

(3Bh)

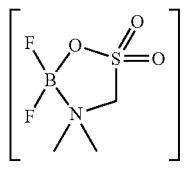

(3Bi)

Among them, it is preferable that the ionic complex is any one selected from the group consisting of the above-mentioned 3Pa, 3Pb, 3Pd, 3Pg, 3Ba, 3Bb, 3Bf, 3Bg, and 3Bi from the viewpoint that use of it as a component of an electrolyte for a nonaqueous electrolyte battery enhances the cycle characteristics of the nonaqueous electrolyte battery.

Incidentally, the relationship between the types of ionic complex and the strength of the effect of improving the cycle characteristics when the ionic complex is used as a component of the electrolyte for a nonaqueous electrolyte battery satisfies: 3Pa>1Bd-Li>>3Ba>3Bi, 3Bf>>3Pd. Therefore, it is preferable that the ionic complex is 3Pa or 1Bd-Li. Note here that the above-mentioned "1Bd-Li" means an ionic complex in which A of 1Bd is Li.

Electrolyte for Nonaqueous Electrolyte Battery

An electrolyte for a nonaqueous electrolyte battery of the present invention contains a solute, the above-mentioned ionic complex, a nonaqueous organic solvent and/or a polymer.

[Solute]

A solute is not particularly limited, and salts including a pair of any cation and anion can be used. Specific examples of the cation includes a lithium ion and a sodium ion, and other alkali metal ions, alkaline earth metal ions, quaternary ammonium, and the like, and specific examples of the anion include hexafluorophosphate, tetrafluoroborate, perchlorate, hexafluoroarsenate, hexafluoroantimonate, trifluoromethanesulfonate, bis(trifluoromethane sulfonyl)imide, bis(pentafluoroethane sulfonyl)imide, (trifluoromethane sulfonyl)(pentafluoroethane sulfonyl)imide, bis(fluorosulfonyl)imide (hereinafter, also referred to as "FSI"), (trifluoromethane sulfonyl) (fluorosulfonyl)imide, (pentafluoroethane sulfonyl) (fluorosulfonyl)imide, tris(trifluoromethane sulfonyl) methide, and bis(difluorophosphonyl)imide, and the like.

These solutes may be used singly, or two or more types of these solutes may be used in any combination or ratio depending on applications of use. Among them, in view of energy density, output characteristics, lifetime, and the like, as a battery, the cation is preferably lithium, sodium, magnesium, and quaternary ammonium, and the anion is preferably hexafluorophosphate, tetrafluoroborate, bis(trifluoromethane sulfonyl)imide, bis(fluorosulfonyl)imide, and bis (difluorophosphonyl)imide.

When the ionic complex is a compound represented by the above-mentioned 3Pa, in a nonaqueous electrolyte battery, the increase range of the cycle characteristics improvement effect (in comparison with the case without addition of 3Pa) is larger in the case where the solute is $LiBF_4$ or LiFSI than in the case where the solute is $LiPF_6$.

The concentration of the solute is not particularly limited, but the lower limit is in a range of 0.5 mol/L or more, preferably 0.7 mol/L or more, and further preferably 0.9 mol/L or more, and the upper limit is in a range of 5.0 mol/L or less, preferably 4.0 mol/L or less, and further preferably 2.0 mol/L or less, with respect to the electrolyte for a nonaqueous electrolyte battery. When the concentration is less than 0.5 mol/L, the ionic conductivity is reduced, so that the cycle characteristics and the output characteristics of the nonaqueous electrolyte battery are deteriorated. On the other hand, when the concentration is more than 5.0 mol/L, the viscosity of the electrolyte for a nonaqueous electrolyte battery is increased. Also in this case, the ionic conductivity is reduced, which may deteriorate the cycle characteristics and the output characteristics of the nonaqueous electrolyte battery.

When the solute is dissolved in a nonaqueous solvent in a large amount at one time, a temperature of the nonaqueous electrolyte may be increased due to heat of dissolution of the solute. When the liquid temperature is remarkably increased, decomposition of fluorine atom-containing lithium salt is promoted, and hydrogen fluoride may be generated. The hydrogen fluoride is not preferable because it is a cause of deterioration of the battery performance. Therefore, the liquid temperature when the solute is dissolved in the nonaqueous solvent is not particularly limited, but it is preferably −20° C. to 50° C., and more preferably 0° C. to 40° C.

[Ionic Complex]

The concentration of the ionic complex is not particularly limited, but the concentration is preferably in a range from 0.001 to 20 mass %, preferably in a range from 0.01 to 10 mass %, further preferably in a range from 0.1 to 5 mass %, and particularly preferably in a range from 0.5 to 2 mass % with respect to the total amount of the solute, the nonaqueous organic solvent, and the ionic complex. When the concentration of the ionic complex is too low, the effect of improving the durability at high temperature, for example, the cycle characteristics of nonaqueous electrolyte battery may not sufficiently be achieved. When the concentration is too high, the viscosity of the electrolyte is increased too much, movement of cations in the nonaqueous electrolyte battery is prevented, and thus the deterioration of the battery performance may be caused.

[Nonaqueous Organic Solvent]

An electrolyte for a nonaqueous electrolyte battery is generally called a nonaqueous electrolyte when a nonaqueous organic solvent is included. The nonaqueous organic solvent is not particularly limited as long as it is an aprotonic solvent capable of dissolving the ionic complex of the present invention. Examples thereof include carbonates, esters, ethers, lactones, nitriles, amides, and sulfones. Specific examples include at least one selected from the group consisting of ethyl methyl carbonate (EMC), dimethyl carbonate, diethyl carbonate (DEC), methyl propyl carbonate, ethyl propyl carbonate (EP), methyl butyl carbonate, ethylene carbonate (EC), fluoroethylene carbonate (FEC), propylene carbonate (PC), butylene carbonate, methyl acetate, methyl propionate, ethyl propionate, diethyl ether, acetonitrile, propionitrile, tetrahydrofuran, 2-methyltetrahydrofuran, furan, tetrahydropyran, 1,3-dioxane, 1,4-dioxane, dibutyl ether, diisopropyl ether, 1,2-dimethoxyethane, N,N-dimethylformamide, dimethylsulfoxide, sulfolane, γ-butyrolactone, and γ-valerolactone.

When the ionic complex is a compound represented by the above-mentioned 3Pa, in an nonaqueous electrolyte battery, the increase range of the effect of improving the cycle characteristics (in comparison with the case without addition of 3Pa) is slightly larger in the case where the nonaqueous organic solvent is a mixed solvent of PC/DEC than a mixed solvent of EC/EMC.

The nonaqueous organic solvent may be not only a single solvent but also a mixed solvent of two or more of solvents.

Note here that it is preferable that the above-mentioned nonaqueous organic solvent contains at least one selected from the group consisting of cyclic carbonate and chain carbonate because it has oxidation resistance and high ionic conductivity. It is preferable that the above-mentioned cyclic carbonate is at least one selected from the group consisting of ethylene carbonate, propylene carbonate, and butylene carbonate. It is preferable that the above-mentioned chain carbonate is at least one selected from the group consisting of ethyl methyl carbonate, dimethyl carbonate, diethyl carbonate, methyl propyl carbonate, ethyl propyl carbonate, and methyl butyl carbonate.

[Polymer]

An electrolyte for a nonaqueous electrolyte battery including a polymer is generally called a polymer solid electrolyte. The polymer solid electrolyte also includes an electrolyte containing a nonaqueous solvent as a plasticizer.

The polymer is not particularly limited as long as it is an aprotonic polymer capable of dissolving the solute and ionic complex mentioned above. Examples thereof include a polymer having polyethylene oxide in a main chain or a side chain, a homopolymer or a copolymer of polyvinylidene fluoride, a methacrylic acid ester polymer, polyacrylonitrile, and the like. Examples of the polymers to which a plasticizer is added include the aprotonic nonaqueous organic solvent mentioned above.

[Second Compound]

Although not an essential aspect, it is preferable that the electrolyte for a nonaqueous electrolyte battery of the present invention further contains at least one second compound selected from the group consisting of fluorine-containing compounds represented by the following general formulae (9) to (16). Containing of the second compound can further improve the output characteristics at low temperature.

[Chem. 27]

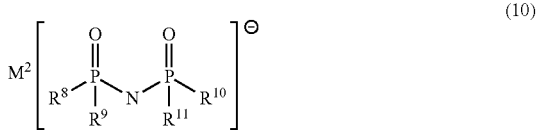

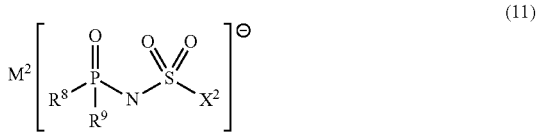

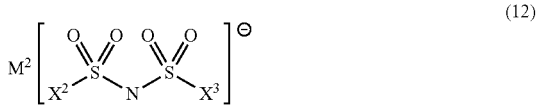

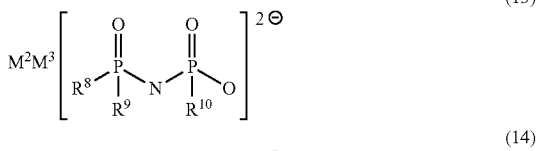

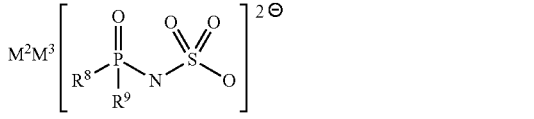

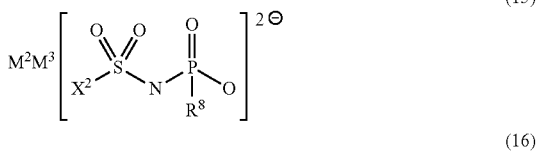

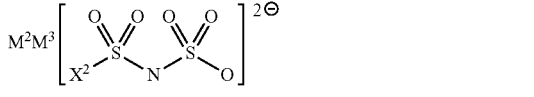

A part of the second compound is decomposed on the positive electrode and the negative electrode to form a coating having high ion-conductivity on the surfaces of the positive electrode and the negative electrode. This coating suppresses direct contact of the nonaqueous solvent and the solute with the electrode active material, to prevent the nonaqueous solvent or the solute from being decomposed and to suppress deterioration of battery performance.

In the electrolyte for a nonaqueous electrolyte battery of the present invention, by using the ionic complex and the second compound together, it is possible to improve high-temperature cycle characteristics and high-temperature storage characteristics at temperatures higher by not less than 50° C. as compared with the case where the ionic complex is added singly, and low-temperature characteristics. Although the detail of the mechanism is not clear, it is considered that when the ionic complex and the second compound are present together, the second compound along with the ionic complex is actively decomposed on the positive electrode and the negative electrode, and a coating having higher ion-conductivity and more excellent durability is formed. Thus, it is considered that decomposition of solvent or solute at high temperature is suppressed and the increase in resistance at low temperature is suppressed. In particular, it is considered that when a large number of fluorophosphoryl structures and/or fluorosulfonyl structures are incorporated into the coating, the electric charge of the formed coating is biased, and a coating with high lithium conductivity, that is, low resistance (a coating with excellent output characteristics) is formed. Furthermore, it is considered that the more the site including unsaturated bonds is included in the ionic complex and the second compound, the more easily the decomposition on the positive electrode and the negative electrode tends to occur, so that a coating with excellent durability can be easily formed. Therefore, it is considered that the above-mentioned effect becomes more excellent. Furthermore, it is considered that when a site having high electron-withdrawing properties (for example, a fluorine atom or fluorine-containing alkoxy group) is included in the second compound, the bias of the electric charge becomes larger, and thus a coating with less resistance (a coating with more excellent output characteristics) is formed.

For the reasons mentioned above, it is supposed that use of the ionic complex and the second compound together improves the average discharge voltage (output characteristics) at −30° C. or less, and the cycle characteristics and the storage characteristics at high temperature of 50° C. or more as compared with the case where each of the ionic complex and the second compound is used singly.

In the above-mentioned general formulae (9) to (16), it is important to include at least one of a P—F bond and/or an S—F bond in achieving the improvement effect mentioned above. When the P—F bond or the S—F bond is not included, the low-temperature characteristics cannot be improved. It is preferable that a larger number of the P—F bonds and the S—F bonds are included because the more excellent low-temperature characteristics can be obtained.

In the above-mentioned general formulae (9) to (16), examples of cation represented by $M^2$ and $M^3$ include a proton, a metal cation and an onium cation. The types of cation are not particularly limited and they can be selected from the above-mentioned various cations as long as they do not hinder the performance of the electrolyte for a nonaqueous electrolyte battery and the nonaqueous electrolyte battery of the present invention. Specific examples include cations of metal such as lithium, sodium, potassium, rubidium, cesium, magnesium, calcium, barium, silver, copper, and iron, and cations of onium such as tetraalkyl ammonium, tetraalkyl phosphonium, and imidazolium derivatives. In particular, from the viewpoint that they play a role of aiding the ionic conductivity in the nonaqueous electrolyte battery, a lithium ion, a sodium ion, a potassium ion, tetramethyl ammonium ion, tetraethyl ammonium ion, tetrabutyl phosphonium ion, and the like, are preferable.

In the above-mentioned general formulae (9) to (11) and (13) to (15), $R^8$ and $R^{11}$ represents: an alkoxy group, for example, an alkoxy group and a fluorine-containing alkoxy group having 1 to 10 carbon atoms, such as a methoxy group, an ethoxy group, a propoxy group, an isopropoxy group, a butoxy group, a secondary butoxy group, a tertiary butoxy group, a pentyloxy group, a trifluoromethoxy group, a 2,2-difluoroethoxy group, a 2,2,2-trifluoroethoxy group, a 2,2,3,3-tetrafluoropropoxy group, and a 1,1,1,3,3,3-hexafluoroisopropoxy group; an alkenyloxy group, for example, an alkenyloxy group and a fluorine-containing alkenyloxy group having 2 to 10 carbon atoms, such as a vinyloxy group, a 1-propenyloxy group, a 2-propenyloxy group, an isopropenyloxy group, a 2-butenyloxy group, a 3-butenyloxy group, and a 1,3-butadienyloxy group; an alkynyloxy group, for example, an alkynyloxy group and a fluorine-containing alkynyloxy group having 2 to 10 carbon atoms, such as an ethynyloxy group, a 2-propynyloxy group, and a 1,1-dimethyl-2-propynyloxy group; a cycloalkoxy group, for example, a cycloalkoxy group and a fluorine-containing cycloalkoxy group having 3 to 10 carbon atoms, such as a cyclopentyloxy group and a cyclohexyloxy group; a cycloalkenyloxy group, for example, a cycloalkenyloxy group and a fluorine-containing cycloalkenyloxy group having 3 to 10 carbon atoms, such as a cyclopentenyloxy group, and a cyclohexenyloxy group; and an aryloxy group, for example, an aryloxy group and a fluorine-containing aryloxy group having 6 to 10 carbon atoms, such as a phenyloxy group, a tolyloxy group, and a xylyloxy group.

In the above-mentioned general formulae (9) to (11) and (13) to (15), it is preferable that $R^8$ to $R^{11}$ are a fluorine atom or an alkoxy group having a fluorine atom, because its strong electron-withdrawing property improves ion dissociation, resulting in enhancing the ionic conductivity in a solution or in a composition. Furthermore, in the above-mentioned general formulae (9) to (11) and (13) to (15), it is preferable that $R^8$ to $R^{11}$ are a fluorine atom, because an improvement effect of mobility by the reduction in anion size extremely increases the ionic conductivity in the solution or the composition. Thus, it is considered that as the larger the number of P—F bonds in the above-mentioned general formulae (9) to (16) becomes, the more the low-temperature characteristics are improved. Furthermore, the above-mentioned $R^8$ to $R^{11}$ are preferably an organic group selected from the group consisting of an alkenyloxy group and an alkynyloxy group. Unlike the above-mentioned alkenyloxy group and alkynyloxy group, a hydrocarbon group which does not include an oxygen atom is not preferable because the electron-withdrawing property is small and an ion dissociation is deteriorated, and the ionic conductivity is reduced in the solution or the composition. Furthermore, groups having an unsaturated bond, such as the above-mentioned alkenyloxy group and alkynyloxy group are preferable because they are actively decomposed on the positive electrode and the negative electrode, and a coating having more excellent durability can be formed. Furthermore, when the number of carbon atoms is large, the anion size becomes large, and the ionic conductivity in the solution or the composition tends to be reduced. Therefore, the numbers of carbon atoms of $R^8$ to $R^{11}$ are preferably 6 or less. The numbers of carbon atoms is preferably 6 or less because the above-mentioned ionic conductivity tends to be relatively high. In particular, a group selected from the group consisting of a 1-propenyloxy group, a 2-propenyloxy group, a 3-butenyloxy group, a 2-propynyloxy group, and a 1,1-dimethyl-2-propynyloxy group are preferable because the anion size is relatively small.

In the above-mentioned general formulae (11), (12), (15), and (16), $X^2$ and $X^3$ represent: an alkyl group, for example, an alkyl group and a fluorine-containing alkyl group having 1 to 10 carbon atoms, such as a methyl group, an ethyl group, a propyl group, an isopropyl group, a butyl group, a secondary butyl group, a tertiary butyl group, a pentyl group, a trifluoromethyl group, a 2,2-difluoroethyl group, a 2,2,2-trifluoroethyl group, a 2,2,3,3-tetrafluoropropyl group, and a 1,1,1,3,3,3-hexafluoroisopropyl group; an alkenyl group, for example, an alkenyl group and a fluorine-containing alkenyl group having 2 to 10 carbon atoms, such as a vinyl group, a 1-propenyl group, a 2-propenyl group, an isopropenyl group, a 2-butenyl group, a 3-butenyl group, and a 1,3-butadienyl group; an alkynyl group, for example, an alkynyl group and a fluorine-containing alkynyl group having 2 to 10 carbon atoms, such as an ethynyl group, a 2-propynyl group, and a 1,1-dimethyl-2-propynyl group; a cycloalkyl group, for example, a cycloalkyl group and a fluorine-containing cycloalkyl group having 3 to 10 carbon atoms, such as a cyclopentyl group, and a cyclohexyl group; a cycloalkenyl group, for example, a cycloalkenyl group and a fluorine-containing cycloalkenyl group having 3 to 10 carbon atoms, such as a cyclopentenyl group and a cyclohexenyl group; as well as an aryl group, for example, an aryl group and a fluorine-containing aryl group having 6 to 10 carbon atoms, such as a phenyl group, a tolyl group, and a xylyl group.

Furthermore, examples of the alkoxy group include an alkoxy group and a fluorine-containing alkoxy group having 1 to 10 carbon atoms, such as a methoxy group, an ethoxy group, a propoxy group, an isopropoxy group, a butoxy group, a secondary butoxy group, a tertiary butoxy group, a pentyloxy group, a trifluoromethoxy group, a 2,2-difluoroethoxy group, a 2,2,2-trifluoroethoxy group, a 2,2,3,3-tetrafluoropropoxy group, and a 1,1,1,3,3,3-hexafluoroisopropoxy group; examples of the alkenyloxy group include an alkenyloxy group and a fluorine-containing alkenyloxy group having 2 to 10 carbon atoms, such as a vinyloxy group, a 1-propenyloxy group, a 2-propenyloxy group, an isopropenyloxy group, a 2-butenyloxy group, a 3-butenyloxy group, and a 1,3-butadienyloxy group; examples of the alkynyloxy group include an alkynyloxy group and a fluorine-containing alkynyloxy group having 2 to 10 carbon atoms, such as an ethynyloxy group, a 2-propynyloxy group, and a 1,1-dimethyl-2-propynyloxy group; examples of the cycloalkoxy group include a cycloalkoxy group and a fluorine-containing cycloalkoxy group having 3 to 10 carbon atoms, such as a cyclopentyloxy group and a cyclohexyloxy group; examples of the cycloalkenyloxy group include a cycloalkenyloxy group and a fluorine-containing cycloalkenyloxy group having 3 to 10 carbon atoms such as a cyclopentenyloxy group and a cyclohexenyloxy group; and examples of the aryloxy group include an aryloxy group and a fluorine-containing aryloxy group having 6 to 10 carbon atoms, such as a phenyloxy group, a tolyloxy group, and a xylyloxy group.

It is preferable that $X^2$ and $X^3$ in the above-mentioned general formulae (11), (12), (15) and (16) are a fluorine atom because effects of improving ion dissociation by the strong electron-withdrawing property and improving the mobility by reduction of an anion size extremely increase the ionic conductivity in a solution or a composition. Furthermore, it is preferable that the $X^2$ and $X^3$ are an organic group selected from the group consisting of an alkoxy group, an alkenyloxy group, and an alkynyloxy group. Unlike the above-mentioned alkoxy group, alkenyloxy group, and alkynyloxy group, a hydrocarbon group which does not include an oxygen atom is not preferable because the electron-withdrawing property is small and the ion dissociation in a solution or a composition is deteriorated, and the ionic conductivity is deteriorated in a solution or a composition. Furthermore, when the number of carbon atoms is large, the anion size becomes larger, so that the ionic conductivity in a solution or a composition tends to be deteriorated. Accordingly, the number of carbon atoms of the above-mentioned $X^2$ and $X^3$ is preferably 6 or less. It is preferable that the number of carbon atoms is 6 or less because the above-mentioned ionic conductivity tends to be relatively high. In particular, a group selected from the group consisting of a methoxy group, an ethoxy group, a propoxy group, a 1-propenyloxy group, a 2-propenyloxy group, a 3-butenyloxy group, a 2-propynyloxy group, and a 1,1-dimethyl-2-propynyloxy group is preferable because the anion size is relatively small.

Note here that compounds having a structure in which all of $R^8$ to $R^{10}$ and $X^2$ of the above-mentioned general formulae (9), (13), (14), and (15) has a hydrocarbon group including an oxygen atom (an alkoxy group, an alkenyloxy group, an alkynyloxy group, a cycloalkoxy group, a cycloalkenyloxy group, an aryloxy group), that is, compounds which do not include a P—F bond or a S—F bond at all, have extremely low solubility in a nonaqueous electrolyte (for example, less than 0.001 mass %). Therefore, it is difficult to add such compounds into the nonaqueous electrolyte to achieve the improvement effects mentioned above.

A suitable addition concentration of the second compound with respect to the total amount of the solute, the nonaqueous organic solvent, the ionic complex, and the second compound has a lower limit of 0.001 mass % or more, more preferably 0.01 mass % or more, and further preferably 0.1 mass % or more, and an upper limit of 10.0 mass % or less, more preferably 5.0 mass % or less, and further preferably 2.0 mass % or less. When the concentration is less than 0.001 mass %, the effect of improving the output characteristics of the nonaqueous electrolyte battery at low temperature may not sufficiently be obtained. On the other hand, it is not preferable that the concentration is more than 10.0 mass %, because further effects cannot be obtained and such concentration is useless, and further because the viscosity of the electrolyte is increased, and the ionic conductivity tends to be deteriorated. Thus, resistance is increased to cause the battery performance to be deteriorated easily. Note here that one type of the second compound may be added, or a plurality of types may be added.

More specifically, examples of a negative ion of phosphate represented by the above-mentioned general formula (9) include the following compound No. 9-1, and the like. However, phosphate to be used in the present invention is not necessarily limited by the following examples.

[Chem. 28]

Compound No. 9-1

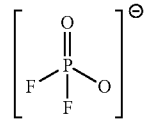

More specifically, examples of a negative ion of imide salt represented by the above-mentioned general formulae (10) to (16) include the following compound. However, the imide salt to be used in the present invention is not necessarily limited by the following examples.

[Chem. 29]

Compound No 10-1

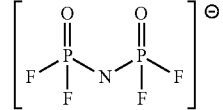

Compound No. 10-2

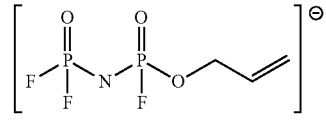

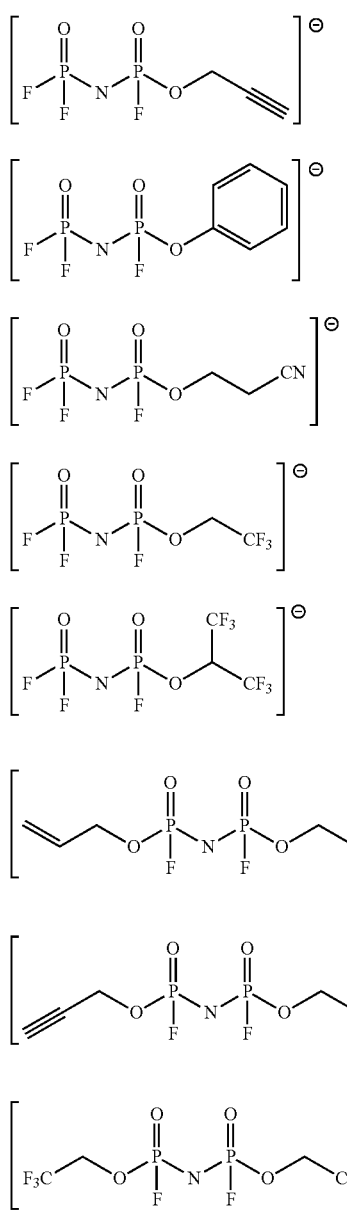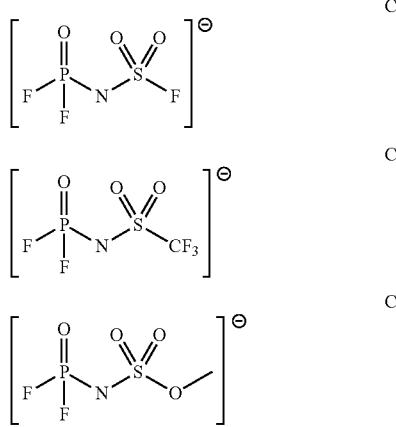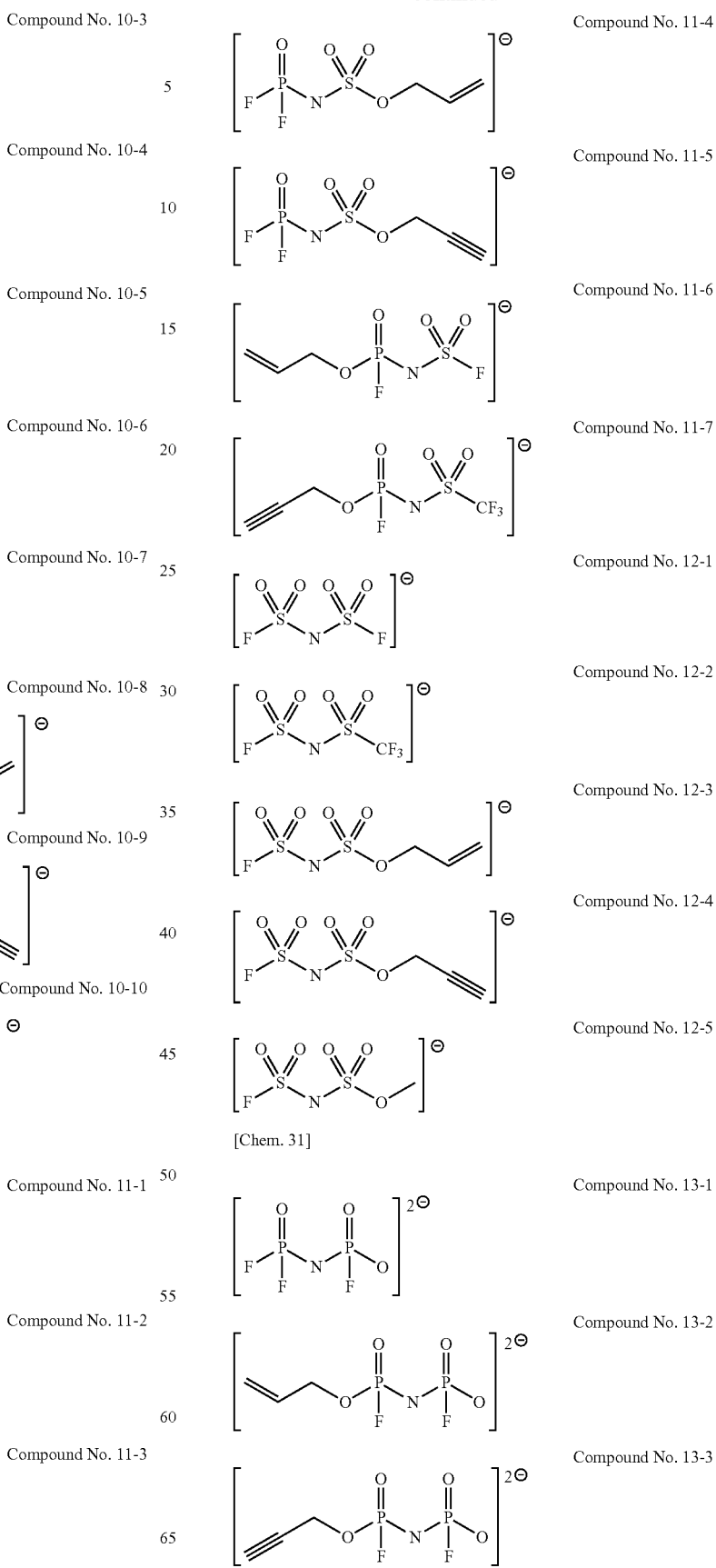

-continued

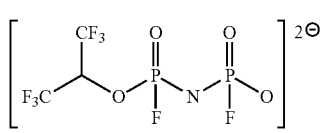
Compound No. 13-4

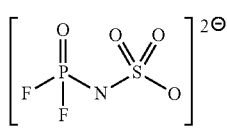
Compound No. 14-1

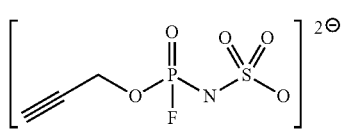
Compound No. 14-2

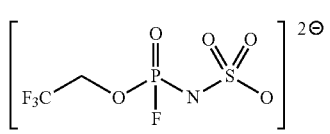
Compound No. 14-3

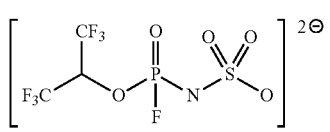
Compound No. 14-4

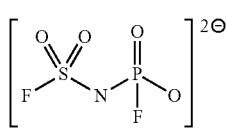
Compound No. 15-1

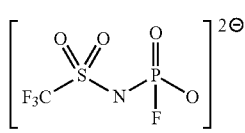
Compound No. 15-2

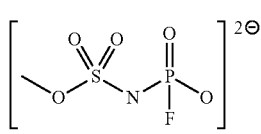
Compound No. 15-3

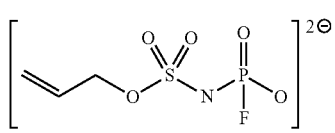
Compound No. 15-4

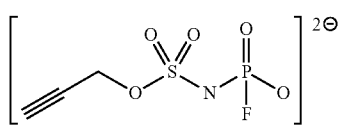
Compound No. 15-5

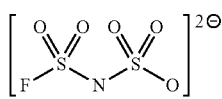
Compound No. 16-1

Salts including a negative ion of phosphate represented by the above-mentioned general formula (9) can be produced by, for example, as descried in the following documents, a method of reacting halide other than fluoride, $LiPF_6$, and water in a nonaqueous solvent, a method of reacting pyrophosphate ester having corresponding alkoxy groups and hydrogen fluoride with each other.

Patent Document 5: Japanese Unexamined Patent Application, Publication No. 2008-222484

Non-Patent Document 1: Journal of the American Chemical Society, 72, 4956-4958, (1950)

Non-Patent Document 2: Faraday Discussion, 145, 281-299, (2010)

Salts including the imide anion represented by the above-mentioned general formula (10) can be produced by various methods. Examples of the production method include, a method of reacting the corresponding phosphoryl chloride ($P(=O)R^8R^9Cl$) and the corresponding amide phosphate ($H_2NP(=O)R^{10}R^{11}$) with each other in the presence of an organic base or an inorganic base, although not necessarily limited thereto.

Salts including the imide anion represented by the above-mentioned general formula (11) can be produced by various methods. Examples of the production method include a method of reacting the corresponding phosphoryl chloride ($P(=O)R^8R^9Cl$) and the corresponding sulfonamide ($H_2NSO_2X^2$) with each other in the presence of an organic base or an inorganic base, although not necessarily limited thereto.

Salts including the imide anion represented by the above-mentioned general formula (12) can be produced by various methods. Examples of the production method include a method of reacting the corresponding sulfonyl chloride ($X^2SO_2Cl$) and the corresponding sulfonamide ($H_2NSO_2X^3$) with each other in the presence of an organic base or an inorganic base, although not necessarily limited thereto.

Salts including the imide anion represented by the above-mentioned general formula (13) can be produced by various methods. Examples of the production method include a method of reacting the corresponding phosphoryl chloride ($P(=O)R^8R^9Cl$) and the corresponding amide phosphate ($H_2NP(=O)R^{10}O^-$) with each other in the presence of an organic base or an inorganic base, although not necessarily limited thereto.

Salts including the imide anion represented by the above-mentioned general formula (14) can be produced by various methods. Examples of the production method include a method of reacting the corresponding phosphoryl chloride ($P(=O)R^8R^9Cl$) and the corresponding sulfamic acid ($H_2NSO_3^-$) with each other in the presence of an organic base or an inorganic base, although not necessarily limited thereto.

Salts including the imide anion represented by the above-mentioned general formula (15) can be produced by various methods. Examples of the production method include a method of reacting the corresponding sulfonyl chloride ($X^2SO_2Cl$) and the corresponding amide phosphate ($H_2NP(=O)R^8O^-$) with each other in the presence of an organic base or an inorganic base, although not necessarily limited thereto.

Salts including the imide anion represented by the above-mentioned general formula (16) can be produced by various methods. Examples of the production method include a method of reacting the corresponding sulfonyl chloride ($X^2SO_2Cl$) and the corresponding sulfamic acid ($H_2NSO_3^-$) with each other in the presence of an organic base or an inorganic base, although not necessarily limited thereto.

Furthermore, in the above-mentioned production methods of salts of the general formulae (9) to (16), cation exchange can be appropriately carried out.

[Third Compound]

Although not an essential aspect, it is preferable that an electrolyte for a nonaqueous electrolyte battery of the present invention further contains at least one third compound represented by the following general formula (17). Containing of the third compound can achieve at least one of reduction in the amount of gas generated and improvement of the cycle characteristics.

$$Si(R^{12})_x(R^{13})_{4-x} \quad (17)$$

A suitable addition concentration of the third compound with respect to the total amount of the solute, the nonaqueous organic solvent, the ionic complex, and the third compound is 0.005 mass % or more, preferably 0.03 mass % or more, and further preferably 0.7 mass % or more. While the upper limit is 7.0 mass % or less, preferably 5.5 mass % or less, and further preferably 2.5 mass % or less. The concentration of less than 0.005 mass % is not preferable because it is difficult to sufficiently obtain the effect of improving the high-temperature cycle characteristics or high-temperature storage characteristics of the nonaqueous electrolyte battery using the nonaqueous electrolyte. On the other hand, the concentration of more than 7.0 mass % is not preferable because it is difficult to sufficiently obtain the effect of improving the high-temperature cycle characteristics and the high-temperature storage characteristics of a nonaqueous electrolyte battery using the nonaqueous electrolyte. These third compounds may be used singly or two or more types of compounds may be used in any combination and ratio depending on the application as long as the concentration is in a range of not exceeding 7.0 mass %.

Examples of a group including an unsaturated carbon-carbon bond represented by $R^{12}$ in the general formula (17) include an alkenyl group having 2 to 8 carbon atoms, such as a vinyl group, an allyl group, a 1-propenyl group, an isopropenyl group, a 2-butenyl group, and a 1,3-butadienyl group, or alkenyloxy groups derived from these groups; an alkynyl group having 2 to 8 carbon atoms, such as, an ethynyl group, a 2-propynyl group, a 1,1dimethyl-2-propynyl group, or an alkynyloxy group derived from these groups; and an aryl group having 6 to 12 carbon atoms, such as a phenyl group, a tolyl group, and a xylyl group, or aryloxy group derived from these groups. Furthermore, the above-mentioned groups may include a fluorine atom and an oxygen atom. Among them, a group having 6 or less carbon atoms and containing an unsaturated carbon-carbon bond is preferable. When the number of carbon atoms is more than 6, resistance when a coating is formed on the electrode tends to be large. Specifically, a group selected from the group consisting of a vinyl group, an allyl group, a 1-propenyl group, an ethynyl group, and a 2-propynyl group is preferable.

Furthermore, in the above-mentioned general formula (17), examples of the alkyl group and the alkoxy group represented by $R^{13}$ include an alkyl group having 1 to 12 carbon atoms, such as a methyl group, an ethyl group, a propyl group, an isopropyl group, a n-butyl group, a sec-butyl group, an isobutyl group, a tert-butyl group, and a pentyl group, or alkoxy groups derived from these groups. Examples of the alkenyl group and the alkenyloxy group include an alkenyl group having 2 to 8 carbon atoms, such as a vinyl group, an allyl group, a 1-propenyl group, an isopropenyl group, a 2-butenyl group, and a 1,3-butadienyl group, or alkenyloxy groups derived from these groups. Examples of an alkynyl group and an alkynyloxy group include an alkynyl group having 2 to 8 carbon atoms, such as an ethynyl group, a 2-propynyl group, and a 1,1-dimethyl-2-propynyl group, or alkynyloxy groups derived from these groups. Examples of an aryl group and an aryloxy group include aryl groups having 6 to 12 carbon atoms, such as a phenyl group, a tolyl group, and a xylyl group, or aryloxy groups derived from these groups. Furthermore, the above-mentioned groups may include a fluorine atom and an oxygen atom. Furthermore, examples of groups other than the group represented by $R^{13}$ include a fluorine atom. Among them, groups selected from a fluorine atom, an alkyl group and an alkoxy group are preferable because the resistance when a coating is formed on the electrode tends to be small, and, as a result, preferable from the viewpoint of the output characteristics. In particular, a group selected from the group consisting of a fluorine atom, a methyl group, an ethyl group, a propyl group, a 2,2,2-trifluoroethyl group, a 2,2,3,3-tetrafluoropropyl group, a 1,1,1-trifluoroisopropyl group, a 1,1,1,3,3,3-hexafluoroisopropyl group, a 2,2,2-trifluoroethoxy group, a 2,2,3,3-tetrafluoropropoxy group, a 2,2,3,3,3-pentafluoropropoxy group, a 1,1,1-trifluoroisopropoxy group, and a 1,1,1,3,3,3-hexafluoroisopropoxy group is preferable because nonaqueous electrolyte batteries in which resistance is not increased and which is more excellent in high-temperature cycle characteristics and high-temperature storage characteristics are obtained.

More specifically, examples of the third compound represented by the above-mentioned general formula (17) include the following compounds No. 17-1 to No. 17-25, and the like. However, the third compound to be used in the present invention is not limited by the following examples.

[Chem. 32]

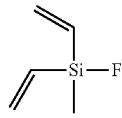

Compound No. 17-1

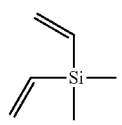

Compound No. 17-2

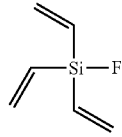

Compound No. 17-3

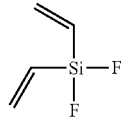

Compound No. 17-4

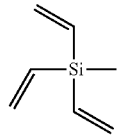

Compound no. 17-5

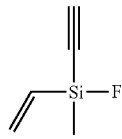

Compound No. 17-6

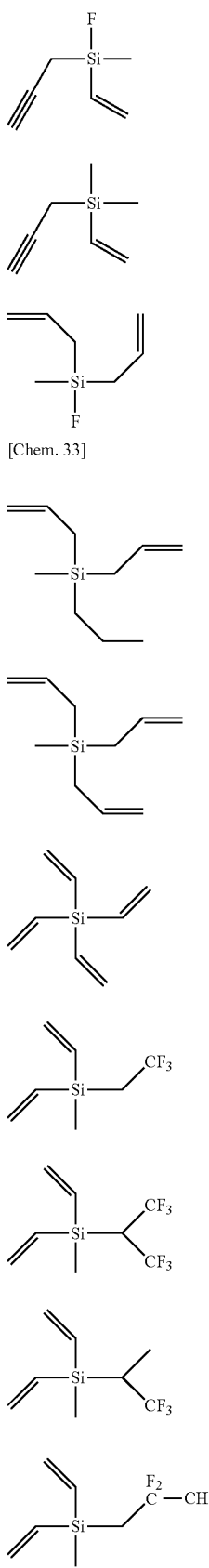
[Fourth Compound]
Although not an essential aspect, it is preferable that the electrolyte for a nonaqueous electrolyte battery of the present invention further contains at least one fourth compound selected from the group consisting of a cyclic sulfonic acid compound represented by the following general formulae (18), (19), and (20), 1,3-propane sultone (PS), and 1,2-pentanediol sulfate ester (PEGLST). Containing of the fourth compound can achieve at least one of reduction in the amount of gas generated, improvement of the cycle characteristics and improvement of the output characteristics at low temperature.

[Chem. 36]

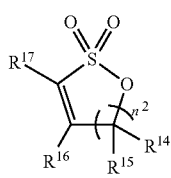

(18)

[Chem. 37]

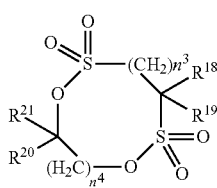

(19)

[Chem. 38]

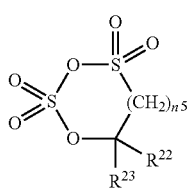

(20)

A suitable addition concentration of the fourth compound with respect to the total amount of the solute, the nonaqueous organic solvent, the ionic complex, and the fourth compound has a lower limit of 0.001 mass % or more, more preferably 0.01 mass % or more, and further preferably 0.1 mass % or more, and an upper limit of 10.0 mass % or less, more preferably 5.0 mass % or less, and further preferably 2.0 mass % or less. The concentration of less than 0.001 mass % is not preferable because it is difficult to sufficiently obtain the effect of improving the high-temperature cycle characteristics or high-temperature storage characteristics of the nonaqueous electrolyte battery using the nonaqueous electrolyte. On the other hand, the concentration of more than 10.0 mass % is not preferable because it is difficult to sufficiently obtain the effect of improving the high-temperature cycle characteristics or the high-temperature storage characteristics of the nonaqueous electrolyte battery using the nonaqueous electrolyte. One type of these fourth compounds may be used singly or two or more types of thereof may be used in any combination or ratio depending on the application as long as the above-mentioned concentration is in a range of not exceeding 10.0 mass %.

Examples of the cyclic sulfonic acid ester having an unsaturated bond represented by general formula (18) include 1,3-propene sultone, 1,4-butene sultone, 2,4-pentene sultone, 3,5-pentene sultone, 1-fluoro-1,3-propene sultone, 1-trifluoromethyl-1,3-propene sultone, 1,1,1-trifluoro-2,4-butene sultone, 1,4-butene sultone, 1,5-pentene sultone, and the like. Among them, in view of the reactivity in the battery system, it is preferable that 1,3-propene sultone (1,3-PRS) and 1,4-butene sultone are used.

Only one type of cyclic sulfonic acid ester having an unsaturated bond may be used or two or more types thereof may be used in combination. When a nonaqueous electrolyte containing the above-mentioned cyclic sulfonic acid ester having an unsaturated bond is used for a battery, a coating is formed on the positive electrode and the negative electrode.

Examples of the cyclic disulfonate ester represented by the general formula (19) include compounds represented by the formulae (19-1) to (19-29) and the like. Among them, the compound represented by the formula (19-1), (19-2), (19-10), (19-15), or (19-16) is preferable. Note here that the cyclic disulfonate ester represented by the general formula (19) is not limited to the compounds represented by the formulae (19-1) to (19-29) and may be the other compounds.

[Chem. 39]

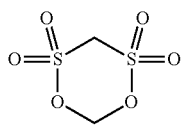

Compound No. 19-1

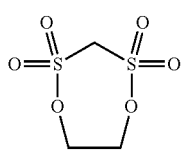

Compound No. 19-2

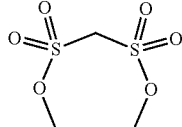

Compound No. 19-3

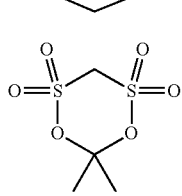

Compound No. 19-4

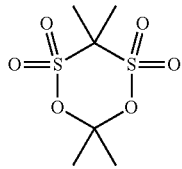

Compound No. 19-5

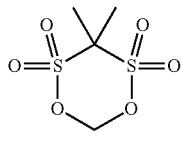

Compound No. 19-6

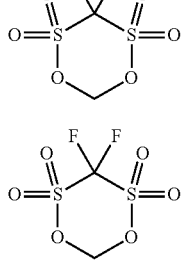

Compound No. 19-7

Compound No. 19-8
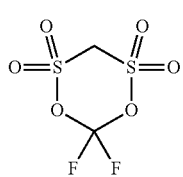
Compound No. 19-9
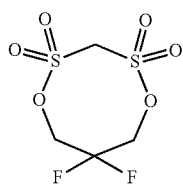
Compound No. 19-10
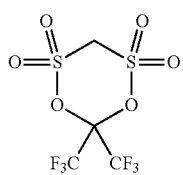
Compound No. 19-11
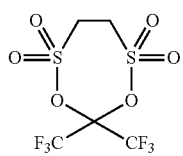
Compound No. 19-12
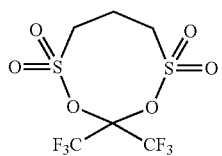
Compound No. 19-13
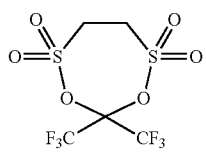
Compound No. 19-14
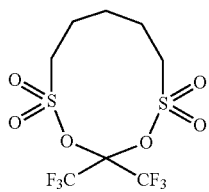
Compound No. 19-15
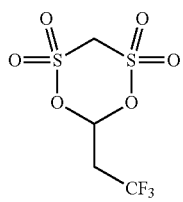
Compound No. 19-16
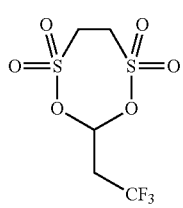
Compound No. 19-17
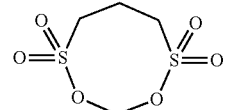
Compound No. 19-18
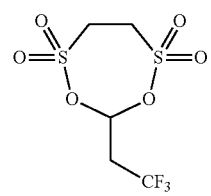
[Chem. 40]
Compound No. 19-19
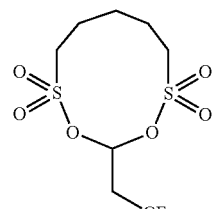
Compound No. 19-20
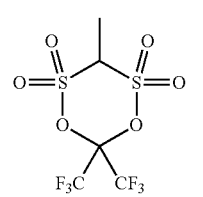
Compound No. 19-21
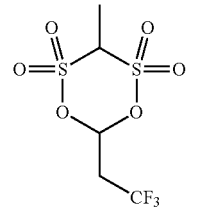
Compound No. 19-22
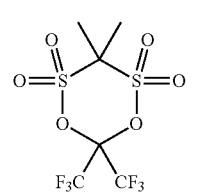
Compound No. 19-23
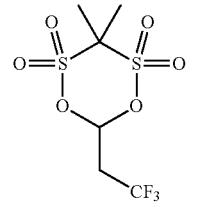

-continued

Compound No. 19-24
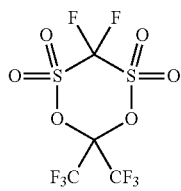

Compound No. 19-25
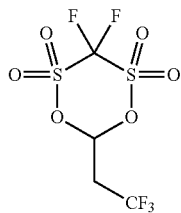

Compound No. 19-26
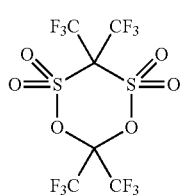

Compound No. 19-27
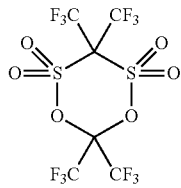

Compound No. 19-28
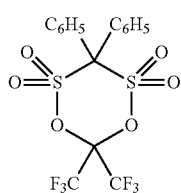

Compound No. 19-29
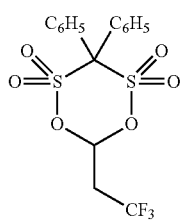

Examples of the cyclic disulfonate ester represented by the general formula (20) include compounds represented by the formulae (20-1) to (20-5) and the like. Among them, the compound represented by the formula (20-1), (20-2) or (20-5) is more preferable. Note here that the cyclic disulfonate ester represented by the general formula (20) is not limited to the compounds represented by the formulae (20-1) to (20-5) and may be the other compounds.

[Chem. 41]

Compound No. 20-1
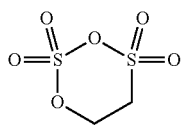

Compound No. 20-2
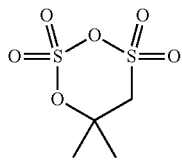

Compound No. 20-23
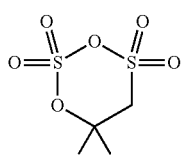

Compound No. 20-4
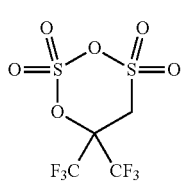

Compound No. 20-5
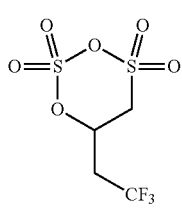

The cyclic disulfonate esters represented by general formulae (18) to (20), PS and PEGLST may be used singly, or two or more types may be used in combination.

[Fifth Compound]

Although not an essential aspect, it is preferable that the electrolyte for a nonaqueous electrolyte battery of the present invention further contains at least one fifth compound selected from the group consisting of cyclic carbonate compounds represented by the following general formula (21). Containing of the fifth compound can improve the cycle characteristics.

[Chem. 42]

(21)
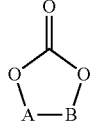

A suitable addition concentration of the fifth compound with respect to the total amount of the solute, the nonaqueous organic solvent, the ionic complex, and the fifth compound has a lower limit of 0.001 mass % or more, more preferably 0.01 mass % or more, and further preferably 0.1 mass % or more, and an upper limit of 10.0 mass % or less, more preferably 5.0 mass % or less, and further preferably 2.0 mass % or less. The concentration of less than 0.001 mass % is not preferable because it is difficult to sufficiently obtain the effect of improving the high-temperature cycle characteristics of a nonaqueous electrolyte battery using the nonaqueous electrolyte. On the other hand, the concentration of more than 10.0 mass % is not preferable because even with such concentration, it is difficult to sufficiently obtain the effect of improving the high-temperature cycle characteristics of a nonaqueous electrolyte battery using the nonaqueous electrolyte. These fifth compounds may be used singly or two or more types thereof may be used in any combination or ratio depending on the application as long as the above-mentioned concentration is in a range of not exceeding 10.0 mass %.

Examples of the fifth compound represented by general formula (21) include cyclic carbonate compounds represented by formulae (21-1) to (21-6). Among them, from the viewpoint that the effect of improving durability is high, the compound represented by formula (21-1) is more preferable. Note here that the cyclic carbonate compound represented by general formula (21) is not limited to the compounds represented by the formulae (21-1) to (21-6), and may be the other compounds.

[Chem. 43]

Compound No. 21-1

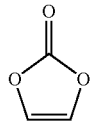

Compound No. 21-2

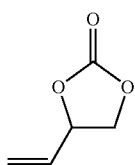

Compound No. 21-3

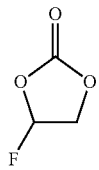

Compound No. 21-4

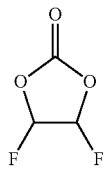

-continued

Compound No. 21-5

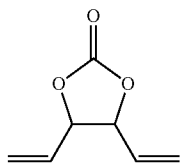

Compound No. 21-6

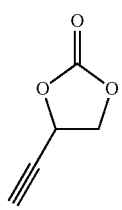

[Additive Agent]

In addition, additive agents which are generally used may be added to the electrolyte for a nonaqueous electrolyte battery of the present invention in any ratio as long as the purpose of the present invention is not affected. Specific examples include compounds having an overcharge prevention effect, a negative electrode coating formation effect and a positive electrode protection effect, for example, cyclohexylbenzene, biphenyl, t-butyl benzene, difluoroanisole, and dimethyl vinylene carbonate. Furthermore, as in the case of use for a nonaqueous electrolyte battery called a polymer battery, an electrolyte for a nonaqueous electrolyte battery can be used in a pseudo-solid state using a gelling agent or a cross linked polymer.

Nonaqueous Electrolyte Battery

A nonaqueous electrolyte battery of the present invention includes a positive electrode, a negative electrode including lithium or negative electrode material capable of absorbing/releasing lithium, and the above-mentioned electrolyte for the nonaqueous electrolyte battery. Alternatively, the battery of the present invention includes a positive electrode, a negative electrode including sodium or negative electrode material capable of absorbing/releasing sodium, and the above-mentioned electrolyte for the nonaqueous electrolyte battery.

[Positive Electrode]

Types of the positive electrode are not particularly limited, and a material which permits reversible insertion and elimination of an alkali metal ion such as a lithium ion and a sodium ion, or an alkaline earth metal ion is used.

When a cation is lithium, examples of the positive electrode material include lithium-containing transition metal composite oxide such as $LiCoO_2$, $LiNiO_2$, $LiMnO_2$, and $LiMn_2O_4$, a material mixture of a plurality of transition metals such as Co, Mn, and Ni of the lithium-containing transition metal composite oxide, a material in which a part of the transition metal in the lithium-containing transition metal composite oxide is substituted with metal other than the transition metal, a phosphate compound of transition metal, for example, $LiFePO_4$, $LiCoPO_4$, and $LiMnPO_4$, called olivine, oxide such as $TiO_2$, $V_2O_5$, and $MoO_3$, sulfide such as $TiS_2$ and FeS, or conductive polymer such as polyacetylene, polyparaphenylene, polyaniline, and polypyrrole, active carbon, polymer generating radical, carbon material, and the like.

Incidentally, in the present invention, regardless of the types of the positive electrode, even when the positive electrode is any of lithium cobaltate (LCO), nickel-cobalt-manganese (NCM), lithium iron phosphate (LFP), lithium nickelate (NCA), and lithium manganate (LMO), although there is difference in the strength of the effect of improving the cycle characteristics, any combinations may provide an excellent effect.

[Negative Electrode]

The types of the negative electrodes are not particularly limited, but a material which permits reversible insertion and elimination of an alkali metal ion such as a lithium ion or a sodium ion, or an alkaline earth metal ion, can be used.

When a cation is lithium, as the negative electrode material, lithium metal, an alloy of lithium and other metal, and an intermetallic compound and various carbon materials capable of absorbing and releasing lithium, metal oxide, metal nitride, active carbon, conductive polymer, and the like, are used. Examples of the above-mentioned carbon material include easily-graphitizable carbon or hardly-graphitizable carbon in which a spacing of a plane (002) is 0.37 nm or more (also called hard carbon), and graphite in which a spacing of a plane (002) is 0.37 nm or less. The latter includes artificial graphite, natural graphite, and the like.

Incidentally, in the present invention, regardless of types of the negative electrode, in any cases where the negative electrode is graphite, hard carbon, silicon, and LTO, although there is difference in the strength of the effect of improving the cycle characteristics, an excellent effect is found in any combinations. Among them, in particular, when silicon is used for the negative electrode, the effect of improving the cycle characteristics is high. This is supposed to be because a protective coating made of the ionic complex of the present invention suppresses a large volume change due to charge and discharge, which is the largest problem of a silicon negative electrode, to some degree.

[Others]

In the positive electrode and the negative electrode, acetylene black, Ketjen black, carbon fiber, or graphite is added as a conductive agent; and polytetrafluoroethylene, polyvinylidene fluoride, or SBR resin or the like is added as a binding agent can be added. Furthermore, an electrode sheet which has been molded into a sheet-shape can be used.

As a separator for preventing the positive electrode and negative electrode from being brought into contact with each other, non-woven fabric or porous sheet made of polypropylene, polyethylene, paper, glass fiber, or the like, can be used.

From the above-mentioned elements, a coin-shaped, cylindrical, prismatic, or aluminum laminate sheet type electrochemical devices are fabricated.

Method for Synthesizing an Ionic Complex

The method for synthesizing an ionic complex according to the present invention includes a reaction step of reacting phosphorus pentafluoride and/or boron trifluoride with at least one selected from the group consisting of carbosulfonic acid or salt thereof, disulfonic acid or salt thereof, amino acid or salt thereof, amide carboxylic acid or salt thereof, diamide or salt thereof, aminosulfonic acid or salt thereof, imine acid or salt thereof, and imine sulfonic acid or salt thereof (a counter cation of an acid anion is at least one cation selected from the group consisting of a proton ion, an alkali metal ion, an alkaline earth metal ion, and quaternary ammonium) in a solvent. Note here that after this synthesis method, an operation of exchanging cations may be carried out.

[Reaction Step]

Types of a solvent to be used for the reaction step are not particularly limited. From the viewpoint that raw material salt can be appropriately dissolved, the solvent is preferably at least one selected from the group consisting of ethyl methyl carbonate, dimethyl carbonate, diethyl carbonate, methyl propyl carbonate, ethyl propyl carbonate, methyl acetate, methyl propionate, diethyl ether, acetonitrile, tetrahydrofuran, 2-methyltetrahydrofuran, furan, tetrahydropyran, 1,3-dioxane, 1,4-dioxane, diisopropyl ether, and 1,2-dimethoxyethane.

An internal temperature during the reaction step is not particularly limited, but the temperature is preferably $-40°$ C. or more and $120°$ C. or less or $-40°$ C. or more and not more than a boiling point of the solvent, more preferably $-20°$ C. or more and $80°$ C. or less, and further preferably $-10°$ C. or more and $50°$ C. or less. When the internal temperature is too low, it may take a long time to synthesize the ionic complex. When the internal temperature is too high, the solvent is volatilized and the ionic complex may not be able to be appropriately synthesized.

[Purification Step]

Furthermore, although not an essential step, in order to enhance the purity of the ionic complex, it is preferable that a purification step is carried out after the reaction step.

One aspect of the purification step includes a purification step including adding sodium hexafluorophosphate to a solution including the ionic complex and 1 mass % or more lithium tetrafluoroborate, thereby precipitating and then filtrating a tetrafluoroborate anion as sodium tetrafluoroborate.

An addition amount of sodium hexafluorophosphate is not particularly limited, but the addition amount with respect to the lithium tetrafluoroborate is preferably 0.8 molar equivalent or more and 1.2 molar equivalent or less, more preferably 0.9 molar equivalent or more and 1.1 molar equivalent or less, and further preferably 0.98 molar equivalent or more and 1.02 molar equivalent or less. When the addition amount is too small, a residual amount of lithium tetrafluoroborate may be increased. When the addition amount is too large, a residual amount of unreacted sodium hexafluorophosphate may be increased.

EXAMPLES

Hereinafter, the present invention will be described in more detail by referring to Examples. It is to be noted that the present invention is not necessarily limited to these Examples.

First Embodiment

Electrolyte for Nonaqueous Electrolyte Battery Containing Specific Ionic Complex Examples 1-8 Synthesis of Ionic Complex

TABLE 1

| | Example 1 | Example 2 | Example 3 | Example 4 |
|---|---|---|---|---|
| Ionic complex | (1Bb-Li) | (1Bd-Li) | (1Bd-Na) | (3Pa) |
| | Example 5 | Example 6 | Example 7 | Example 8 |
| Ionic complex | (3Pd) | (3Ba) | (3Bi) | (3Bf) |

Ionic complexes of Examples 1 to 8 were synthesized by the following procedures. In any cases, raw materials and products were treated under nitrogen atmosphere at a dew point of −50° C. or less. Furthermore, a glass reactor, which had been dried at 150° C. for 12 hours or more and then cooled to room temperature under the stream of nitrogen at a dew point of −50° C. or less, was used.

Example 1 Synthesis of 1Bb-Li

Lithium methylene disulfonate (18.8 g, 100.0 mmol) and dimethyl carbonate (hereinafter, referred to as "DMC") (150 g) having a water content of 100 mass ppm or less were placed in a 500 mL-glass reactor. When boron trifluoride (hereinafter, referred to as "$BF_3$") (13.2 g, 200.0 mmol) was introduced into the reactor at 10° C. over 20 min while stirring, the properties of solid deposited on the bottom of the reactor were changed. The temperature was increased to room temperature, and stirring was continued for 24 hours. When the composition of the reaction liquid was analyzed by F-NMR, the reaction liquid contained 3 mol % 1Bb-Li and 97 mol % lithium tetrafluoroborate (hereinafter, referred to as $LiBF_4$). Solubility of 1Bb-Li into DMC was low and most of 1Bb-Li was precipitated.

Solids were recovered by filtration under reduced pressure, washed with 20 g of EMC, and further dried under reduced pressure at 40° C. for three hours to obtain 18.6 g of 1Bb-Li with purity of 98 mol % (F-NMR). Remaining 2 mol % was $LiBF_4$.

Example 2 Synthesis of 1Bd-Li

Lithium sulfoacetate (15.2 g, 100.0 mmol) and DMC (150 g) containing 100 mass ppm or less of water were placed in a 500 mL-glass reactor. When $BF_3$ (13.2 g, 200.0 mmol) was introduced into the reactor at 10° C. over 20 min while stirring, a considerable amount of slightly soluble lithium sulfoacetate disappeared, and the progress of reaction was demonstrated. The temperature was increased to room temperature, and stirring was continued for 24 hours. When the composition of the reaction liquid was analyzed by F-NMR, the reaction liquid contained 49 mol % 1Bb-Li and 51 mol % $LiBF_4$.

Sodium hexafluorophosphate (16.8 g, 100.0 mmol) was added to the resultant product, and the mixture was stirred at room temperature for four hours, followed by filtration to remove an insoluble product. The composition of recovered filtrate was analyzed by F-NMR, the filtrate included 47 mol % 1Bd-Li, 51 mol % lithium hexafluorophosphate (hereinafter, referred to as $LiPF_6$), and 2 mol % $LiBF_4$. $LiBF_4$ contained in large quantities was converted into slightly soluble lithium tetrafluoroborate (hereinafter, referred to as $NaBF_4$) by cation exchange with $NaPF_6$ to be precipitated, and most of the precipitates were removed by filtration. The filtrates were subjected to concentration under reduced pressure, and DMC was removed by evaporation so that the concentration reached about 30 mass %, and then cooled to 5° C. Crystals were precipitated. The crystals were recovered by filtration under reduced pressure, dried at 40° C. for three hours under reduced pressure to obtain 17.1 g of 1Bd-Li with purity of 97 mol % (F-NMR). Remaining 3 mol % was $LiPF_6$.

Example 3 Synthesis of 1Bd-Na

Sodium sulfoacetate (18.4 g, 100.0 mmol) and DMC (150 g) having a water content of 100 mass ppm or less were placed in a 500 mL-glass reactor. When $BF_3$ (13.2 g, 200.0 mmol) was introduced into the reactor at 10° C. over 20 min while stirring, the properties of solid deposited on the bottom of the reactor were changed. The temperature was increased to room temperature, and stirring was continued for 24 hours. When the composition of the reaction liquid was analyzed by F-NMR, almost all the composition was 1Bd-Na. However, the concentration thereof was small and a considerable amount of precipitate was deposited. The resultant product was separated into filtrate and a solid content by filtration under reduced pressure. The solid content was washed twice with 150 g of DMC. A washing solution recovered and the above-obtained filtrate were mixed with each other, and DMC was removed by evaporation under reduced pressure and heating to obtain 1Bd-Na having purity of 98 mol % (F-NMR). Remaining (2 mol %) was $NaBF_4$.

Example 4 Synthesis of 3Pa

Lithium picolinate (12.9 g, 100.0 mmol) and ethyl methyl carbonate (hereinafter, referred to as "EMC") (150 g) having a water content of 100 mass ppm or less were placed in a 500 mL-glass reactor. When phosphorus pentafluoride (hereinafter, referred to as "$PF_5$") (25.2 g, 200.0 mmol) was introduced into the reactor at room temperature over 20 min while stirring, a considerable amount of slightly soluble lithium picolinate disappeared. Thus, progress of reaction was demonstrated. Stirring was continued as it is at room temperature for 24 hours. Insoluble products were removed by filtration, and then the composition of the reaction liquid was analyzed by F-NMR. The composition includes 49 mol % 3Pa and 51 mol % $LiPF_6$.

Example 5 Synthesis of 3Pd

N,N-dimethylglycine lithium (10.9 g, 100.0 mmol) and EMC (150 g) having a water content of 100 mass ppm or less were placed in a 500 mL-glass reactor. When $PF_5$ (25.2 g, 200.0 mmol) was introduced into the reactor at room temperature over 20 min while stirring, most of slightly soluble N,N-dimethylglycine lithium disappeared. Thus, progress of reaction was demonstrated. Stirring was continued as it is at room temperature for 24 hours. Insoluble products were removed by filtration, and then the composition of reaction liquid was analyzed by F-NMR. As a result, the composition includes 48 mol % 3Pd and 52 mol % $LiPF_6$.

Example 6 Synthesis of 3Ba

Lithium picolinate (12.9 g, 100.0 mmol) and DMC (150 g) having a water content of 100 mass ppm or less were placed in a 500 mL-glass reactor. When $BF_3$ (13.2 g, 200.0 mmol) was introduced into the reactor at 10° C. over 20 min while stirring, a considerable amount of slightly soluble lithium picolinate disappeared, and the progress of reaction was demonstrated. The temperature was increased to room temperature, and stirring was continued for 24 hours. When the composition of the reaction liquid was analyzed by F-NMR, the composition includes 49 mol % 3Ba and 51 mol % $LiBF_4$. When insoluble products were removed by filtration, and the reaction liquid was concentrated under reduced pressure, white solids were precipitated. The precipitated solids were recovered by filtration under reduced pressure, and further dried at 40° C. for three hours under reduced pressure to obtain 3Ba having purity of more than 99 mol % (F-NMR).

Example 7 Synthesis of 3Bi

Lithium N,N-dimethylamino methane sulfonate (14.5 g, 100.0 mmol) and EMC (150 g) having a water content of 100 mass ppm or less were placed in a 500 mL-glass reactor. $BF_3$ (13.2 g, 200.0 mmol) was introduced into the reactor at 10° C. over 20 min while stirring. The temperature was increased to room temperature, and stirring was continued for 24 hours. Precipitates were recovered by filtration, and dried at 40° C. for three hours under reduced pressure to obtain 3Bi having purity of more than 99 mol % (F-NMR).

Example 8 Synthesis of 3Bf

Lithium pyridine-2-sulfonate (16.5 g, 100.0 mmol) and DMC (150 g) having a water content of 100 mass ppm or less were placed in a 500 mL-glass reactor. When $BF_3$ (13.2 g, 200.0 mmol) was introduced into the reactor at 10° C. over 20 min while stirring, a considerable amount of slightly soluble lithium pyridine-2-sulfonate disappeared, and progress of reaction was demonstrated. The temperature was increased to room temperature, and stirring was continued for 24 hours. When the composition of the reaction liquid was analyzed by F-NMR, the composition includes 50 mol % 3Bf and 50 mol % $LiBF_4$. When insoluble products were removed by filtration, and the reaction liquid was concentrated under reduced pressure, white solids were precipitated. The precipitated solids were recovered by filtration under reduced pressure, and dissolved in 100 g of EMC. When insoluble products were removed by filtration again, followed by concentration under reduced pressure, white solid was precipitated. The solids were recovered by filtration. Furthermore, the resultant product was dried at 40° C. for three hours under reduced pressure to obtain 3Bf having purity of 99 mol % (F-NMR).

Example 9

Synthesis was carried out by the same procedure as in Example 4 except that picolinic acid (12.3 g, 100.0 mmol) instead of lithium picolinate was used as the raw material, and then F-NMR was measured. The composition of the reaction liquid includes 49 mol % 3Pa and 51 mol % hexafluorophosphate ($HPF_6$). To this reaction liquid, LiCl (4.3 g, 102 mmol) was added. The mixture was stirred at room temperature for three hours, and the generated hydrochloric acid was removed under reduced pressure. $HPF_6$ generated as a by-product was converted into $LiPF_6$.

Examples 11-77 and Comparative Examples 11-18
Preparation of Electrolyte for Nonaqueous Electrolyte Battery

TABLE 2

| | Solute | | Ionic complex | | |
|---|---|---|---|---|---|
| Example | Type | Concentration [mol/L] | Type | Addition amount [mass %] | Nonaqueous organic solvent Type |
| 11 | $LiPF_6$ | 1 | 1Bb-Li (Example 1) | 0.01 | EMC:EC = 2:1 (Volume ratio) |
| 12 | | | | 0.1 | |
| 13 | | | | 0.2 | |
| 14 | $LiPF_6$ | 1 | 1Bd-Li (Example 2) | 0.01 | EMC:EC = 2:1 (Volume ratio) |
| 15 | | | | 0.1 | |
| 16 | | | | 1 | |
| 17 | | | | 3 | |
| 18 | $LiPF_6$ | 1 | 3Pa (Example 4) | 0.01 | EMC:EC = 2:1 (Volume ratio) |
| 19 | | | | 0.1 | |

TABLE 2-continued

| Example | Solute Type | Concentration [mol/L] | Ionic complex Type | Addition amount [mass %] | Nonaqueous organic solvent Type |
|---|---|---|---|---|---|
| 20 | | | | 1 | |
| 21 | | | | 3 | |
| 22 | $LiPF_6$ | 1 | 3Pd (Example 5) | 0.01 | EMC:EC = 2:1 (Volume ratio) |
| 23 | | | | 0.1 | |
| 24 | | | | 1 | |
| 25 | | | | 0 | |
| 26 | $LiPF_6$ | 1 | 3Ba (Example 6) | 0.01 | EMC:EC = 2:1 (Volume ratio) |
| 27 | | | | 0.1 | |
| 28 | | | | 1 | |
| 29 | | | | 0 | |
| 30 | $LiPF_6$ | 1 | 3Bi (Example 7) | 0.01 | EMC:EC = 2:1 (Volume ratio) |
| 31 | | | | 0.1 | |
| 32 | | | | 1 | |
| 33 | | | | 0 | |
| 34 | $LiPF_6$ | 1 | 3Bf (Example 8) | 0.01 | EMC:EC = 2:1 (Volume ratio) |
| 35 | | | | 0.1 | |
| 36 | | | | 1 | |
| 37 | | | | 3 | |
| 38 | $LiPF_6$ | 1.2 | 1Bd-Li (Example 2) | 0.01 | EMC:EC = 2:1 (Volume ratio) |
| 39 | | | | 0.1 | |
| 40 | | | | 1 | |
| 41 | | | | 3 | |
| 42 | $LiPF_6$ | 1.2 | 3Pa (Example 4) | 0.01 | EMC:EC = 2:1 (Volume ratio) |
| 43 | | | | 0.1 | |
| 44 | | | | 1 | |
| 45 | | | | 3 | |
| 46 | $LiBF_4$ | 1 | 3Pa (Example 4) | 0.01 | EMC:EC = 2:1 (Volume ratio) |
| 47 | | | | 0.1 | |
| 48 | | | | 1 | |
| 49 | | | | 3 | |
| 50 | LiFSI | 1 | 3Pa (Example 4) | 0.01 | EMC:EC = 2:1 (Volume ratio) |
| 51 | | | | 0.1 | |
| 52 | | | | 1 | |
| 53 | | | | 3 | |

TABLE 3

| Example | Solute Type | Concentration [mol/L] | Ionic complex Type | Addition amount [mass %] | Nonaqueous organic solvent Type |
|---|---|---|---|---|---|
| 54 | $LiPF_6$ | 1 | 1Bd-Li (Example 2) | 0.01 | DEC:PC = 2:1 (Volume ratio) |
| 55 | | | | 0.1 | |
| 56 | | | | 1 | |
| 57 | | | | 0 | |
| 58 | $LiPF_6$ | 1 | 3Pa (Example 4) | 0.01 | DEC:PC = 2:1 (Volume ratio) |
| 59 | | | | 0.1 | |
| 60 | | | | 1 | |
| 61 | | | | 0 | |
| 62 | $NaPF_6$ | 1 | 1Bd-Na (Example 3) | 0.01 | DEC:PC = 2:1 (Volume ratio) |
| 63 | | | | 0.1 | |
| 64 | | | | 1 | |
| 65 | | | | 0 | |
| 66 | $NaPF_6$ | 1 | 3Pa (Example 4) | 0.01 | DEC:PC = 2:1 (Volume ratio) |
| 67 | | | | 0.1 | |
| 68 | | | | 1 | |
| 69 | | | | 3 | |
| 70 | NaFSI | 1 | 1Bd-Na (Example 3) | 0.01 | DEC:PC = 2:1 (Volume ratio) |
| 71 | | | | 0.1 | |
| 72 | | | | 1 | |
| 73 | | | | 3 | |
| 74 | NaFSI | 1 | 3Pa (Example 4) | 0.01 | DEC:PC = 2:1 (Volume ratio) |
| 75 | | | | 0.1 | |
| 76 | | | | 1 | |
| 77 | | | | 3 | |

TABLE 4

| Comparative Example | Solute Type | Concentration [mol/L] | Ionic complex Type | Addition amount [mass %] | Nonaqueous organic solvent Type |
|---|---|---|---|---|---|
| 11 | $LiPF_6$ | 1 | Not added | 0 | EMC:EC = 2:1 (Volume ratio) |
| 12 | $LiPF_6$ | 1.2 | Not added | 0 | |
| 13 | $LiBF_4$ | 1 | Not added | 0 | |
| 14 | LiFSI | 1 | Not added | 0 | |
| 15 | $LiPF_6$ | 1 | 4Pa—Li | 1 | |
| 16 | $LiPF_6$ | 1 | Not added | 0 | DEC:PC = 2:1 (Volume ratio) |
| 17 | $NaPF_6$ | 1 | Not added | 0 | |
| 18 | NaFSI | 1 | Not added | 0 | |

In Tables 2 to 4, the ionic complex (4Pa—Li) is lithium tetrafluorooxalatophosphate.

Furthermore, in Tables 2 to 4, EMC represents ethyl methyl carbonate, EC represents ethylene carbonate, DEC represents diethyl carbonate, and PC represents propylene carbonate.

In Tables 2 to 4, a blank column means the same as above.

The solutes described in Tables 2 to 4 and the ionic complexes described in Tables 2 to 4 were mixed into the nonaqueous organic solvents described in Tables 2 to 4 in a ratio described in Tables 2 to 4 sequentially in the order from the solute to the ionic complex, and the mixture was stirred for one hour to obtain electrolytes for a nonaqueous electrolyte battery of Examples and Comparative Examples, respectively. Note here that the preparation of the electrolytes for a nonaqueous electrolyte battery described in Tables 2 to 4 were carried out while the liquid temperature was maintained at 40° C. or less.

Examples 101-109 and Comparative Examples 101, 102

Production and Evaluation of Nonaqueous Electrolyte Battery: 1A

TABLE 5

| | Positive electrode | Negative electrode | Electrolyte |
|---|---|---|---|
| Example 101 | LCO positive electrode | Graphite negative electrode | Example 13 |
| Example 102 | | | Example 16 |
| Example 103 | | | Example 20 |
| Example 104 | | | Example 24 |

TABLE 5-continued

| | Positive electrode | Negative electrode | Electrolyte |
|---|---|---|---|
| Example 105 | | | Example 28 |
| Example 106 | | | Example 32 |
| Example 107 | | | Example 36 |
| Example 108 | | | Example 40 |
| Example 109 | | | Example 44 |
| Comparative Example 101 | | | Comparative Example 11 |
| Comparative Example 102 | | | Comparative Example 12 |

In Table 5, a blank column means the same as above.

[Production of LCO Positive Electrode]

To 90 mass % LiCoO$_2$ powder, 5 mass % polyvinylidene fluoride (hereinafter, referred to as PVDF) as a binder and 5 mass % acetylene black as a conductive agent were mixed. Further, N-methyl-pyrrolidone (hereinafter, referred to as NMP) was added to the mixture so as to produce a positive electrode mixture paste. This paste was applied to an aluminum foil (current collector), dried, and pressurized, followed by being punched into a predetermined size to obtain a test LCO positive electrode.

[Production of Graphite Negative Electrode]

To 90 mass % graphite powder, 10 mass % PVDF as a binder was mixed. Further, NMP was added to the mixture so as to produce a negative electrode mixture paste. This paste was applied to a copper foil (current collector), dried, and pressurized, followed by being punched into a predetermined size to obtain a test graphite negative electrode.

[Production of Nonaqueous Electrolyte Battery]

An aluminum laminate outer package cell (capacity: 300 mAh) including the above-mentioned test LCO positive electrode, test graphite negative electrode, and a polyethylene separator with which the electrolyte described in Table 5 was impregnated was fabricated so as to obtain nonaqueous electrolyte batteries of Examples and Comparative Examples.

[Evaluation]

Each of the nonaqueous electrolyte batteries of Examples and Comparative Examples was subjected to a charge and discharge test at an environmental temperature of 60° C. to evaluate cycle characteristics at high temperature. Both charge and discharge were carried out at current density of 0.3 mA/cm$^2$. In charging, the voltage reached 4.2 V, and then was maintained at 4.2 V for one hour. The discharge was carried out to 3.0 V. Thus, the charge/discharge cycle was repeated. Then, the degree of deterioration of a cell was evaluated based on the discharge capacity maintenance rate after 500 cycles (evaluation of cycle characteristics). The discharge capacity maintenance rate was calculated from the following formula.

[Discharge capacity maintenance rate after 500 cycles]

Discharge capacity maintenance rate (%)=(Discharge capacity after 500 cycles/Initial discharge capacity)×100

The discharge capacity maintenance rates of nonaqueous electrolyte batteries of Examples 101 to 109 and Comparative Example 102 are respectively shown in Table 6 as a relative value when the discharge capacity maintenance rate of the nonaqueous electrolyte battery of Comparative Example 101 is defined as 100.

TABLE 6

| | Discharge capacity maintenance rate (Relative value) |
|---|---|
| Example 101 | 108 |
| Example 102 | 120 |
| Example 103 | 125 |
| Example 104 | 103 |
| Example 105 | 110 |
| Example 106 | 108 |
| Example 107 | 108 |
| Example 108 | 121 |
| Example 109 | 125 |
| Comparative Example 101 | 100 |
| Comparative Example 102 | 101 |

It was demonstrated that the nonaqueous electrolyte batteries including an electrolyte containing the ionic complex of Examples achieved higher cycle characteristics as compared with nonaqueous electrolyte batteries which do not include the ionic complex.

Examples 110, 111 and Comparative Examples 103, 104

Production and Evaluation of Nonaqueous Electrolyte Battery: 1B

TABLE 7

| | Positive electrode | Negative electrode | Electrolyte |
|---|---|---|---|
| Example 110 | LCO positive electrode | Graphite negative electrode | Example 48 |
| Comparative Example 103 | | | Comparative Example 13 |
| Example 111 | | | Example 52 |
| Comparative Example 104 | | | Comparative Example 14 |

In Table 7, a blank column means the same as above.

[Production of Nonaqueous Electrolyte Battery]

An aluminum laminate outer package cell (capacity: 300 mAh) was fabricated by the same procedure as in Example 101 except that the electrolyte was as described in Table 7 to obtain nonaqueous electrolyte batteries of Examples and Comparative Examples.

[Evaluation]

The discharge capacity maintenance rate was obtained by the same procedure as in Example 101. The discharge capacity maintenance rate of the nonaqueous electrolyte battery in accordance with Example 110 is shown in Table 8 as a relative value when the discharge capacity maintenance rate of the nonaqueous electrolyte battery of Comparative Example 103 is defined as 100. Furthermore, the discharge capacity maintenance rate of the nonaqueous electrolyte battery of Example 111 is shown in Table 8 as relative value when the discharge capacity maintenance rate of the nonaqueous electrolyte battery of Comparative Example 104 is defined as 100.

TABLE 8

| | Discharge capacity maintenance rate (Relative value) |
|---|---|
| Example 110 | 120 |
| Comparative Example 103 | 100 |
| Example 111 | 115 |
| Comparative Example 104 | 100 |

It was demonstrated that the nonaqueous electrolyte batteries including an electrolyte containing the ionic complex of Examples achieved higher cycle characteristics as compared with nonaqueous electrolyte batteries which do not include the ionic complex.

Examples 201-235 and Comparative Examples 201, 202

Production and Evaluation of Nonaqueous Electrolyte Battery: 2A

TABLE 9

| | Positive electrode | Negative electrode | Electrolyte |
|---|---|---|---|
| Example 201 | NCM positive electrode | Graphite negative electrode | Example 11 |
| Example 202 | | | Example 12 |
| Example 203 | | | Example 13 |
| Example 204 | | | Example 14 |
| Example 205 | | | Example 15 |
| Example 206 | | | Example 16 |
| Example 207 | | | Example 17 |
| Example 208 | | | Example 18 |
| Example 209 | | | Example 19 |
| Example 210 | | | Example 20 |
| Example 211 | | | Example 21 |
| Example 212 | | | Example 22 |
| Example 213 | | | Example 23 |
| Example 214 | | | Example 24 |
| Example 215 | | | Example 25 |
| Example 216 | | | Example 26 |
| Example 217 | | | Example 27 |
| Example 218 | | | Example 28 |
| Example 219 | | | Example 29 |
| Example 220 | | | Example 30 |
| Example 221 | | | Example 31 |
| Example 222 | | | Example 32 |
| Example 223 | | | Example 33 |
| Example 224 | | | Example 34 |
| Example 225 | | | Example 35 |
| Example 226 | | | Example 36 |
| Example 227 | | | Example 37 |
| Example 228 | | | Example 38 |
| Example 229 | | | Example 39 |
| Example 230 | | | Example 40 |
| Example 231 | | | Example 41 |
| Example 232 | | | Example 42 |
| Example 233 | | | Example 43 |
| Example 234 | | | Example 44 |
| Example 235 | | | Example 45 |
| Comparative Example 201 | | | Comparative Example 11 |
| Comparative Example 202 | | | Comparative Example 12 |

In Table 9, a blank column means the same as above.

[Production of NCM Positive Electrode]

To 90 mass % $LiNi_{1/3}Mn_{1/3}Co_{1/3}O_2$ powder, 5 mass % PVDF (binder) and 5 mass % acetylene black (conductive agent) were mixed. Further, NMP was added to the mixture so as to produce a positive electrode mixture paste. This paste was applied to an aluminum foil (current collector), dried, and pressurized, followed by being punched into a predetermined size to obtain a test NCM positive electrode.

[Production of Nonaqueous Electrolyte Battery]

An aluminum laminate outer package cell (capacity: 300 mAh) was fabricated by the same procedure as in Example 101 except that the positive electrode was a NCM positive electrode and the electrolyte was as shown in Table 9 to obtain nonaqueous electrolyte batteries of Examples and Comparative Examples.

[Evaluation]

The discharge capacity maintenance rate was obtained by the same procedure as in Example 101. Note here that in charging, the voltage reached 4.3 V, and then was maintained at 4.3 V for one hour. The discharge capacity maintenance rates of the nonaqueous electrolyte batteries of Examples 201 to 235 and Comparative Example 202 are shown in Table 10 as relative values when the discharge capacity maintenance rate of the nonaqueous electrolyte battery of Comparative Example 201 is defined as 100.

TABLE 10

| | Discharge capacity maintenance rate (Relative value) |
|---|---|
| Example 201 | 102 |
| Example 202 | 105 |
| Example 203 | 110 |
| Example 204 | 103 |
| Example 205 | 106 |
| Example 206 | 125 |
| Example 207 | 125 |
| Example 208 | 103 |
| Example 209 | 106 |
| Example 210 | 130 |
| Example 211 | 125 |
| Example 212 | 101 |
| Example 213 | 102 |
| Example 214 | 105 |
| Example 215 | 105 |
| Example 216 | 101 |
| Example 217 | 104 |
| Example 218 | 114 |
| Example 219 | 115 |
| Example 220 | 101 |
| Example 221 | 102 |
| Example 222 | 113 |
| Example 223 | 115 |
| Example 224 | 101 |
| Example 225 | 104 |
| Example 226 | 112 |
| Example 227 | 114 |
| Example 228 | 102 |
| Example 229 | 105 |
| Example 230 | 125 |
| Example 231 | 120 |
| Example 232 | 103 |
| Example 233 | 105 |
| Example 234 | 130 |
| Example 235 | 128 |
| Comparative Example 201 | 100 |
| Comparative Example 202 | 100 |

It was demonstrated that the nonaqueous electrolyte batteries including an electrolyte containing the ionic complex of Examples achieved higher cycle characteristics as compared with nonaqueous electrolyte batteries which do not include the ionic complex. The effect was found even when the content of the ionic complex was 0.01 mass %, although the effect was slight. It was demonstrated that the effect was enhanced as the content of the ionic complex was increased from 0.01 to 0.1, and further to 1 mass %. It was found that the content of the ionic complex of 3 mass % showed not only that higher cycle characteristics were obtained as compared with the case where the content was 1 mass % (Example 207 and others); but also it was hardly different from the case where the content was 1 mass % (Example 215), and that the cycle characteristics were deteriorated as compared with a case where the content was 1 mass % (Example 211). This is assumed to be because the content of the ionic complex reached 3 mass %, the viscosity of the electrolyte is increased to prevent movement of cations in the nonaqueous electrolyte battery, and the battery performance may be deteriorated.

The relationship between the types of the ionic complex and the strength of the effect of improving the cycle characteristics satisfied 3Pa>1Bd-Li>>3Ba>3Bi, 3Bf>>3Pd. When the ionic complex is 3Pa or 1Bd-Li, high cycle characteristics were obtained.

Note here that also when the ionic complex was 1Bb-Li, advantageous effects were obtained (Examples 201 to 203), but had low solubility into a nonaqueous organic solvent, and therefore comparison was not able to be carried out around 1 mass % that is presumed to be an optimum concentration.

Examples 236-243 and Comparative Examples 203, 204

Production and Evaluation of Nonaqueous Electrolyte Battery: 2B

TABLE 11

| | Positive electrode | Negative electrode | Electrolyte |
|---|---|---|---|
| Example 236 | NCM positive electrode | Graphite negative electrode | Example 46 |
| Example 237 | | | Example 47 |
| Example 238 | | | Example 48 |
| Example 239 | | | Example 49 |
| Comparative Example 203 | | | Comparative Example 13 |
| Example 240 | | | Example 50 |
| Example 241 | | | Example 51 |
| Example 242 | | | Example 52 |
| Example 243 | | | Example 53 |
| Comparative Example 204 | | | Comparative Example 14 |

In Table 11, a blank column means the same as above.
[Production of Nonaqueous Electrolyte Battery]
An aluminum laminate outer package cell (capacity: 300 mAh) was fabricated by the same procedure as in Example 101 except that the positive electrode was a NCM positive electrode and the electrolyte was as shown in Table 11 to obtain nonaqueous electrolyte batteries of Examples and Comparative Examples.
[Evaluation]
The discharge capacity maintenance rate was obtained by the same procedure as in Example 101. Note here that in charging, the voltage reached 4.3 V, and then was maintained at 4.3 V for one hour. The discharge capacity maintenance rates of the nonaqueous electrolyte batteries of Examples 236 to 239 are shown in Table 12 as relative values when the discharge capacity maintenance rate of the nonaqueous electrolyte battery of Comparative Example 203 is defined as 100. Furthermore, the discharge capacity maintenance rates of the nonaqueous electrolyte batteries of Examples 240 to 243 are shown in Table 12 as relative values when the discharge capacity maintenance rate of the nonaqueous electrolyte battery of Comparative Example 204 is defined as 100.

TABLE 12

| | Discharge capacity maintenance rate (Relative value) |
|---|---|
| Example 236 | 102 |
| Example 237 | 104 |
| Example 238 | 125 |
| Example 239 | 121 |
| Comparative Example 203 | 100 |

TABLE 12-continued

| | Discharge capacity maintenance rate (Relative value) |
|---|---|
| Example 240 | 101 |
| Example 241 | 105 |
| Example 242 | 120 |
| Example 243 | 115 |
| Comparative Example 204 | 100 |

It was demonstrated that the nonaqueous electrolyte batteries including an electrolyte containing the ionic complex of Examples achieved higher cycle characteristics as compared with nonaqueous electrolyte batteries which do not include the ionic complex.

In particular, in the ionic complex 3Pa, in any of the case where the concentration of the solute $LiPF_6$ is changed from 1 M to 1.2 M (Examples 210, 234), the case where the solute is changed from $LiPF_6$ to $LiBF_4$ (Examples 210, 238), and the case where the solute is changed from $LiPF_6$ to LiFSI (Examples 210, 242), a large effect of improving the cycle characteristics was found as compared with the case where the ionic complex of the present invention was not added.

Examples 301-313 and Comparative Examples 301-305

Production and Evaluation of Nonaqueous Electrolyte Battery: 3

TABLE 13

| | Positive electrode | Negative electrode | Electrolyte |
|---|---|---|---|
| Example 301 | NCM positive electrode | Hard carbon negative electrode | Example 13 |
| Example 302 | | | Example 16 |
| Example 303 | | | Example 20 |
| Example 304 | | | Example 24 |
| Example 305 | | | Example 28 |
| Example 306 | | | Example 32 |
| Example 307 | | | Example 36 |
| Example 308 | | | Example 40 |
| Example 309 | | | Example 44 |
| Comparative Example 301 | | | Comparative Example 11 |
| Comparative Example 302 | | | Comparative Example 12 |
| Example 310 | | | Example 48 |
| Comparative Example 303 | | | Comparative Example 13 |
| Example 311 | | | Example 52 |
| Comparative Example 304 | | | Comparative Example 14 |
| Example 312 | | | Example 56 |
| Example 313 | | | Example 60 |
| Comparative Example 305 | | | Comparative Example 16 |

In Table 13, a blank column means the same as above.
[Production of Hard Carbon Negative Electrode]
To 90 mass % hardly-graphitizable carbon (hereinafter, referred to as hard carbon) powder, 10 mass % PVDF as a binder was mixed. Further, NMP was added to the mixture so as to produce a negative electrode mixture paste. This paste was applied to a copper foil (current collector), dried, and pressurized, followed by being punched into a predetermined size to obtain a test hard carbon negative electrode.
[Production of Nonaqueous Electrolyte Battery]
An aluminum laminate outer package cell (capacity: 300 mAh) was fabricated by the same procedure as in Example 101 except that the positive electrode is a NCM positive electrode, the negative electrode is hard carbon negative electrode, and the electrolyte was as shown in Table 13 to obtain nonaqueous electrolyte batteries of Examples and Comparative Examples.

[Evaluation]

The discharge capacity maintenance rate was obtained by the same procedure as in Example 101. Note here that the discharge was carried out to 2.2 V. The discharge capacity maintenance rates of the nonaqueous electrolyte batteries of Examples 301 to 309 and Comparative Example 302 are shown in Table 14 as relative values when the discharge capacity maintenance rate of the nonaqueous electrolyte battery of Comparative Example 301 is defined as 100. The discharge capacity maintenance rate of the nonaqueous electrolyte battery of Example 310 is shown in Table 14 as a relative value when the discharge capacity maintenance rate of the nonaqueous electrolyte battery of Comparative Example 303 is defined as 100. Furthermore, the discharge capacity maintenance rate of the nonaqueous electrolyte battery of Example 311 is shown in Table 14 as a relative value when the discharge capacity maintenance rate of the nonaqueous electrolyte battery of Comparative Example 304 is defined as 100. The discharge capacity maintenance rates of the nonaqueous electrolyte batteries of Examples 312 and 313 are shown in Table 14 as a relative value when the discharge capacity maintenance rate of the nonaqueous electrolyte battery of Comparative Example 305 is defined as 100.

TABLE 14

| | Discharge capacity maintenance rate (Relative value) |
|---|---|
| Example 301 | 113 |
| Example 302 | 128 |
| Example 303 | 132 |
| Example 304 | 107 |
| Example 305 | 120 |
| Example 306 | 115 |
| Example 307 | 114 |
| Example 308 | 128 |
| Example 309 | 135 |
| Comparative Example 301 | 100 |
| Comparative Example 302 | 100 |
| Example 310 | 125 |
| Comparative Example 303 | 100 |
| Example 311 | 121 |
| Comparative Example 304 | 100 |
| Example 312 | 128 |
| Example 313 | 133 |
| Comparative Example 305 | 100 |

It was demonstrated that the nonaqueous electrolyte batteries including an electrolyte containing the ionic complex of Examples achieved higher cycle characteristics as compared with nonaqueous electrolyte batteries which do not include the ionic complex.

Furthermore, when the nonaqueous organic solvent is changed from EC/EMC to PC/DEC (Examples 303 and 313), a large effect of improving cycle characteristics was found as compared with the case where an ionic complex of the present invention was not added.

Examples 401-404 and Comparative Examples 401-403

Production and Evaluation of Nonaqueous Electrolyte Battery: 4

TABLE 15

| | Positive electrode | Negative electrode | Electrolyte |
|---|---|---|---|
| Example 401 | NCM positive electrode | Silicon negative electrode | Example 16 |
| Example 402 | | | Example 20 |
| Comparative Example 401 | | | Comparative Example 11 |
| Example 403 | | | Example 48 |
| Comparative Example 402 | | | Comparative Example 13 |
| Example 404 | | | Example 52 |
| Comparative Example 403 | | | Comparative Example 14 |

In Table 15, a blank column means the same as above.

[Production of Silicon Negative Electrode]

To 75 mass % elemental silicon powder, 10 mass % polyvinylidene fluoride (PVDF) as a binder and 15 mass % acetylene black as a conductive agent were mixed. Further, N-methyl-2-pyrrolidone (NMP) was added to the mixture so as to produce a negative electrode mixture paste. The paste was applied to a copper foil (current collector), dried, and pressurized, followed by being punched into a predetermined size to obtain a test silicon negative electrode.

[Production of Nonaqueous Electrolyte Battery]

An aluminum laminate outer package cell (capacity: 300 mAh) was fabricated by the same procedure as in Example 101 except that the positive electrode was a NCM positive electrode, negative electrode was a silicon negative electrode, and the electrolyte was as shown in Table 15 to obtain nonaqueous electrolyte batteries of Examples and Comparative Examples.

[Evaluation]

The discharge capacity maintenance rate was obtained by the same procedure as in Example 101. Note here that the degree of deterioration of a cell was evaluated based on the discharge capacity maintenance rate after 100 cycles. The discharge capacity maintenance rates of the nonaqueous electrolyte batteries of Examples 401 and 402 are shown in Table 16 as relative values when the discharge capacity maintenance rate of the nonaqueous electrolyte battery of Comparative Example 401 is defined as 100. The discharge capacity maintenance rate of the nonaqueous electrolyte battery of Example 403 is shown in Table 16 as a relative value when the discharge capacity maintenance rate of the nonaqueous electrolyte battery of Comparative Example 402 is defined as 100. The discharge capacity maintenance rate of the nonaqueous electrolyte battery of Example 404 is shown in Table 16 as a relative value when the discharge capacity maintenance rate of the nonaqueous electrolyte battery of Comparative Example 403 is defined as 100.

TABLE 16

| | Discharge capacity maintenance rate (Relative value) |
|---|---|
| Example 401 | 350 |
| Example 402 | 380 |
| Comparative Example 401 | 100 |
| Example 403 | 200 |
| Comparative Example 402 | 100 |

TABLE 16-continued

|  | Discharge capacity maintenance rate (Relative value) |
|---|---|
| Example 404 | 300 |
| Comparative Example 403 | 100 |

It was demonstrated that the nonaqueous electrolyte batteries including an electrolyte containing the ionic complex of Examples achieved higher cycle characteristics as compared with nonaqueous electrolyte batteries which do not include the ionic complex.

Examples 501-506 and Comparative Examples 501-504

Production and Evaluation of Nonaqueous Electrolyte Battery: 5

TABLE 17

|  | Positive electrode | Negative electrode | Electrolyte |
|---|---|---|---|
| Example 501 | NCM positive electrode | LTO negative electrode | Example 16 |
| Example 502 |  |  | Example 20 |
| Comparative Example 501 |  |  | Comparative Example 11 |
| Example 503 |  |  | Example 48 |
| Comparative Example 502 |  |  | Comparative Example 13 |
| Example 504 |  |  | Example 52 |
| Comparative Example 503 |  |  | Comparative Example 14 |
| Example 505 |  |  | Example 56 |
| Example 506 |  |  | Example 60 |
| Comparative Example 504 |  |  | Comparative Example 16 |

In Table 17, a blank column means the same as above.
[Production of LTO Negative Electrode]
To 90 mass % $Li_4Ti_5O_{12}$ powder, 5 mass % PVDF as a binder and 5 mass % acetylene black as a conductive agent were mixed. Further, NMP was added to the mixture so as to produce a negative electrode mixture paste. This paste was applied to a copper foil (current collector), dried, and pressurized, followed by being punched into a predetermined size to obtain a test LTO negative electrode.
[Production of Nonaqueous Electrolyte Battery]
An aluminum laminate outer package cell (capacity: 300 mAh) was fabricated by the same procedure as in Example 101 except that the positive electrode was a NCM positive electrode, negative electrode was a LTO negative electrode, and the electrolyte was as shown in Table 17 to obtain nonaqueous electrolyte batteries of Examples and Comparative Examples.
[Evaluation]
The discharge capacity maintenance rate was obtained by the same procedure as in Example 101. Note here that in charging, the voltage reached 2.8 V, and then was maintained at 2.8 V for one hour. Discharge was carried out to 1.5 V. The discharge capacity maintenance rates of the nonaqueous electrolyte batteries of Examples 501 and 502 are shown in Table 18 as relative values when the discharge capacity maintenance rate of the nonaqueous electrolyte battery of Comparative Example 501 is defined as 100. The discharge capacity maintenance rate of the nonaqueous electrolyte battery of Example 503 is shown in Table 18 as a relative value when the discharge capacity maintenance rate of the nonaqueous electrolyte battery of Comparative Example 502 is defined as 100. The discharge capacity maintenance rate of the nonaqueous electrolyte battery of Example 504 is shown in Table 18 as a relative value when the discharge capacity maintenance rate of the nonaqueous electrolyte battery of Comparative Example 503 is defined as 100. The discharge capacity maintenance rates of the nonaqueous electrolyte batteries of Examples 505 and 506 are shown in Table 18 as relative values when the discharge capacity maintenance rate of the nonaqueous electrolyte battery of Comparative Example 504 is defined as 100.

TABLE 18

|  | Discharge capacity maintenance rate (Relative value) |
|---|---|
| Example 501 | 110 |
| Example 502 | 113 |
| Comparative Example 501 | 100 |
| Example 503 | 110 |
| Comparative Example 502 | 100 |
| Example 504 | 115 |
| Comparative Example 503 | 100 |
| Example 505 | 112 |
| Example 506 | 114 |
| Comparative Example 504 | 100 |

It was demonstrated that the nonaqueous electrolyte batteries including an electrolyte containing the ionic complex of Examples achieved higher cycle characteristics as compared with nonaqueous electrolyte batteries which do not include the ionic complex.

Herein, results when the ionic complex is fixed to 1Bd-Li or 3Pa, and the positive electrode is fixed to NCM, while a negative electrode is changed are summarized. When the negative electrode was changed from graphite, hard carbon, silicon, to LTO, although there is difference in the strength of the effect of improving the cycle characteristics, an excellent effect was found in any combinations. In particular, the high effect was found when silicon was used for the negative electrode. This is supposed to be because a protective coating made of the ionic complex (1Bd-Li or 3Pa) suppressed a large volume change due to charge and discharge, which is the largest problem of a silicon negative electrode, to some degree. Furthermore, when the LTO negative electrode in which a volume change due to charge and discharge hardly occurs is used, the effect of improving the cycle characteristics by addition of the ionic complex (1Bd-Li or 3Pa) showed a smaller value as compared with the other negative electrodes.

Examples 601-604 and Comparative Examples 601-603

Production and Evaluation of Nonaqueous Electrolyte Battery: 6

TABLE 19

|  | Positive electrode | Negative electrode | Electrolyte |
|---|---|---|---|
| Example 601 | LFP positive electrode | Graphite negative electrode | Example 16 |
| Example 602 |  |  | Example 20 |
| Comparative Example 601 |  |  | Comparative Example 11 |
| Example 603 |  |  | Example 48 |
| Comparative Example 602 |  |  | Comparative Example 13 |

TABLE 19-continued

| | Positive electrode | Negative electrode | Electrolyte |
|---|---|---|---|
| Example 604 | | | Example 52 |
| Comparative Example 603 | | | Comparative Example 14 |

In Table 19, a blank column means the same as above.

[Production of LFP Positive Electrode]

To 90 mass % $LiFePO_4$ powder coated with amorphous carbon, 5 mass % PVDF (binder) and 5 mass % acetylene black (conductive agent) were mixed. Further, NMP was added to the mixture so as to produce a positive electrode mixture paste. This paste was applied to an aluminum foil (current collector), dried, and pressurized, followed by being punched into a predetermined size to obtain a test LFP positive electrode.

[Production of Nonaqueous Electrolyte Battery]

An aluminum laminate outer package cell (capacity: 300 mAh) was fabricated by the same procedure as in Example 101 except that the positive electrode was a LPF positive electrode and the electrolyte was as shown in Table 19 to obtain nonaqueous electrolyte batteries of Examples and Comparative Examples.

[Evaluation]

The discharge capacity maintenance rate was obtained by the same procedure as in Example 101. Note here that in charging, the voltage reached 4.1 V, and then was maintained at 4.1 V for one hour. Discharge was carried out to 2.5 V. The discharge capacity maintenance rates of the nonaqueous electrolyte batteries of Examples 601 and 602 are shown in Table 20 as relative values when the discharge capacity maintenance rate of the nonaqueous electrolyte battery of Comparative Example 601 is defined as 100. The discharge capacity maintenance rate of the nonaqueous electrolyte battery of Example 603 is shown in Table 20 as a relative value when the discharge capacity maintenance rate of the nonaqueous electrolyte battery of Comparative Example 602 is defined as 100. The discharge capacity maintenance rate of the nonaqueous electrolyte battery of Example 604 is shown in Table 20 as a relative value when the discharge capacity maintenance rate of the nonaqueous electrolyte battery of Comparative Example 603 is defined as 100.

TABLE 20

| | Discharge capacity maintenance rate (Relative value) |
|---|---|
| Example 601 | 122 |
| Example 602 | 123 |
| Comparative Example 601 | 100 |
| Example 603 | 120 |
| Comparative Example 602 | 100 |
| Example 604 | 114 |
| Comparative Example 603 | 100 |

It was demonstrated that the nonaqueous electrolyte batteries including an electrolyte containing the ionic complex of Examples achieved higher cycle characteristics as compared with nonaqueous electrolyte batteries which do not include the ionic complex.

Examples 701-704 and Comparative Examples 701-703

Production and Evaluation of Nonaqueous Electrolyte Battery: 7

TABLE 21

| | Positive electrode | Negative electrode | Electrolyte |
|---|---|---|---|
| Example 701 | NCA positive electrode | Graphite negative electrode | Example 16 |
| Example 702 | | | Example 20 |
| Comparative Example 701 | | | Comparative Example 11 |
| Example 703 | | | Example 48 |
| Comparative Example 702 | | | Comparative Example 13 |
| Example 704 | | | Example 52 |
| Comparative Example 703 | | | Comparative Example 14 |

In Table 21, a blank column means the same as above.

[Production of NCA Positive Electrode]

To 90 mass % $LiNi_{0.8}Co_{0.15}Al_{0.05}O_2$ powder, 5 mass % PVDF (binder) and 5 mass % acetylene black (conductive agent) were mixed. Further, NMP was added to the mixture so as to produce a positive electrode mixture paste. This paste was applied to an aluminum foil (current collector), dried, and pressurized, followed by being punched into a predetermined size to obtain a test NCA positive electrode.

[Production of Nonaqueous Electrolyte Battery]

An aluminum laminate outer package cell (capacity: 300 mAh) was fabricated by the same procedure as in Example 101 except that the positive electrode was a NCA positive electrode and the electrolyte was as shown in Table 21 to obtain nonaqueous electrolyte batteries of Examples and Comparative Examples.

[Evaluation]

The discharge capacity maintenance rate was obtained by the same procedure as in Example 101. Note here that in charging, the voltage reached 4.3 V, and then was maintained at 4.3 V for one hour. The discharge capacity maintenance rates of the nonaqueous electrolyte batteries of Examples 701 and 702 are shown in Table 22 as relative values when the discharge capacity maintenance rate of the nonaqueous electrolyte battery of Comparative Example 701 is defined as 100. The discharge capacity maintenance rate of the nonaqueous electrolyte battery of Example 703 is shown in Table 22 as a relative value when the discharge capacity maintenance rate of the nonaqueous electrolyte battery of Comparative Example 702 is defined as 100. The discharge capacity maintenance rate of the nonaqueous electrolyte battery of Example 704 is shown in Table 22 as a relative value when the discharge capacity maintenance rate of the nonaqueous electrolyte battery of Comparative Example 703 is defined as 100.

TABLE 22

| | Discharge capacity maintenance rate (Relative value) |
|---|---|
| Example 701 | 120 |
| Example 702 | 125 |
| Comparative Example 701 | 100 |
| Example 703 | 120 |
| Comparative Example 702 | 100 |

TABLE 22-continued

| | Discharge capacity maintenance rate (Relative value) |
|---|---|
| Example 704 | 115 |
| Comparative Example 703 | 100 |

It was demonstrated that the nonaqueous electrolyte batteries including an electrolyte containing the ionic complex of Examples achieved higher cycle characteristics as compared with nonaqueous electrolyte batteries which do not include the ionic complex.

Examples 801-804 and Comparative Examples 801-803

Production and Evaluation of Nonaqueous Electrolyte Battery: 8

TABLE 23

| | Positive electrode | Negative electrode | Electrolyte |
|---|---|---|---|
| Example 801 | LMO positive electrode | Graphite negative electrode | Example 16 |
| Example 802 | | | Example 20 |
| Comparative Example 801 | | | Comparative Example 11 |
| Example 803 | | | Example 48 |
| Comparative Example 802 | | | Comparative Example 13 |
| Example 804 | | | Example 52 |
| Comparative Example 803 | | | Comparative Example 14 |

In Table 23, a blank column means the same as above.

[Production of LMO Positive Electrode]

To 90 mass % $LiMn_2O_4$ powder, 5 mass % PVDF (binder) and 5 mass % acetylene black (conductive agent) were mixed. Further, NMP was added to the mixture so as to produce a positive electrode mixture paste. This paste was applied to an aluminum foil (current collector), dried, and pressurized, followed by being punched into a predetermined size to obtain a test LMO positive electrode.

[Production of Nonaqueous Electrolyte Battery]

An aluminum laminate outer package cell (capacity: 300 mAh) was fabricated by the same procedure as in Example 101 except that the positive electrode was a LMO positive electrode and the electrolyte was as shown in Table 23 to obtain nonaqueous electrolyte batteries of Examples and Comparative Examples.

[Evaluation]

The discharge capacity maintenance rate was obtained by the same procedure as in Example 101. The discharge capacity maintenance rates of the nonaqueous electrolyte batteries of Examples 801 and 802 are shown in Table 24 as relative values when the discharge capacity maintenance rate of the nonaqueous electrolyte battery of Comparative Example 801 is defined as 100. The discharge capacity maintenance rate of the nonaqueous electrolyte battery of Example 803 is shown in Table 24 as a relative value when the discharge capacity maintenance rate of the nonaqueous electrolyte battery of Comparative Example 802 is defined as 100. The discharge capacity maintenance rate of the nonaqueous electrolyte battery of Example 804 is shown in Table 24 as a relative value when the discharge capacity maintenance rate of the nonaqueous electrolyte battery of Comparative Example 803 is defined as 100.

TABLE 24

| | Discharge capacity maintenance rate (Relative value) |
|---|---|
| Example 801 | 115 |
| Example 802 | 117 |
| Comparative Example 801 | 100 |
| Example 803 | 110 |
| Comparative Example 802 | 100 |
| Example 804 | 110 |
| Comparative Example 803 | 100 |

It was demonstrated that the nonaqueous electrolyte batteries including an electrolyte containing the ionic complex of Examples achieved higher cycle characteristics as compared with nonaqueous electrolyte batteries which do not include the ionic complex.

Examples 901-904 and Comparative Examples 901-902

Production and Evaluation of Nonaqueous Electrolyte Battery: 9

TABLE 25

| | Positive electrode | Negative electrode | Electrolyte |
|---|---|---|---|
| Example 901 | $NaFe_{0.5}Co_{0.5}O_2$ positive electrode | Hard carbon negative electrode | Example 64 |
| Example 902 | | | Example 68 |
| Comparative Example 901 | | | Comparative Example 17 |
| Example 903 | | | Example 72 |
| Example 904 | | | Example 76 |
| Comparative Example 902 | | | Comparative Example 18 |

In Table 25, a blank column means the same as above.

[Production of $NaFe_{0.5}Co_{0.5}O_2$ Positive Electrode]

To 85 mass % $NaFe_{0.5}Co_{0.5}O_2$ powder, 5 mass % PVDF (binder) and 10 mass % acetylene black (conductive agent) were mixed. Further, NMP was added to the mixture so as to produce a positive electrode mixture paste. This paste was applied to an aluminum foil (current collector), dried, and pressurized, followed by being punched into a predetermined size to obtain a test $NaFe_{0.5}Co_{0.5}O_2$ positive electrode.

[Production of Nonaqueous Electrolyte Battery]

An aluminum laminate outer package cell (capacity: 300 mAh) was fabricated by the same procedure as in Example 101 except that the positive electrode was a $NaFe_{0.5}Co_{0.5}O_2$ positive electrode, the negative electrode was a hard carbon negative electrode, and the electrolytes were as shown in Table 25 to obtain nonaqueous electrolyte batteries of Examples and Comparative Examples.

[Evaluation]

The discharge capacity maintenance rate was obtained by the same procedure as in Example 101. Note here that in charging, the voltage reached 3.8 V, and then was maintained at 3.8 V for one hour. Discharge was carried out to 1.5 V. The degree of deterioration of a cell was evaluated based on the discharge capacity maintenance rate after 200 cycles. The discharge capacity maintenance rates of the nonaqueous electrolyte batteries of Examples 901 and 902 are shown in Table 26 as relative values when the discharge capacity maintenance rate of the nonaqueous electrolyte battery of Comparative Example 901 is defined as 100. The discharge capacity maintenance rates of the nonaqueous electrolyte batteries of Examples 903 and 904 are shown in Table 26 as relative values when the discharge capacity maintenance rate of the nonaqueous electrolyte battery of Comparative Example 902 is defined as 100.

TABLE 26

|  | Discharge capacity maintenance rate (Relative value) |
|---|---|
| Example 901 | 140 |
| Example 902 | 150 |
| Comparative Example 901 | 100 |
| Example 903 | 150 |
| Example 904 | 150 |
| Comparative Example 902 | 100 |

It was demonstrated that the nonaqueous electrolyte batteries including an electrolyte containing the ionic complex of Examples achieved higher cycle characteristics as compared with nonaqueous electrolyte batteries which do not include the ionic complex.

Herein, results when the ionic complex is fixed to 1Bd-Li or 3Pa, and the negative electrode is fixed to graphite, while the positive electrode is changed are summarized. When the positive electrode was changed from LCO, NCM, LFP, NCA, to LMO, although there is some differences in the strength of the effect of improving the cycle characteristics, an excellent effect was found in any combinations.

Also in a sodium ion battery in which the cation of the solute is changed from lithium to sodium, when an electrolyte containing the ionic complex 1Bd-Na or 3Pa is used, a high effect of improving the cycle characteristics was found.

Examples 901 to 904

Examples 206, 210 and Comparative Examples 201, 205

TABLE 27

|  | Positive electrode | Negative electrode | Electrolyte |
|---|---|---|---|
| Example 206 | NCM positive electrode | Graphite negative electrode | Example 16 |
| Example 210 |  |  | Example 20 |
| Comparative Example 201 |  |  | Comparative Example 11 |
| Comparative Example 205 |  |  | Comparative Example 15 |

In Table 27, a blank column means the same as above.
[Production of Nonaqueous Electrolyte Battery]

An aluminum laminate outer package cell (capacity: 300 mAh) was fabricated by the same procedure as in Example 101 except that the positive electrode was a NCM positive electrode and the electrolytes were as shown in Table 27 to obtain nonaqueous electrolyte batteries of Examples and Comparative Examples.
[Evaluation]

The nonaqueous electrolyte batteries of Examples and Comparative Examples were subjected to a charge and discharge test at an environmental temperature of 60° C. to evaluate high-temperature cycle characteristics and the amount of gas generated inside the batteries. Both charge and discharge were carried out at current density of 0.3 mA/cm$^2$. In charging, the voltage reached 4.3 V, and then was maintained at 4.3 V for one hour. The discharge was carried out to 3.0 V. Thus, the charge/discharge cycle was repeated. Then, the degree of deterioration of a cell was evaluated based on the amount of gas generated after 10 cycles and the discharge capacity maintenance rate after 500 cycles (evaluation of the amount of gas generated and the cycle characteristics).

The amount of gas generated (mL) was calculated from buoyancy when a laminate cell was taken off from a charge/discharge device, and completely soaked into silicone oil. The discharge capacity maintenance rate and the amount of gas generated are shown in Table 28, as relative values when those of Comparative Example 201 are defined as 100, respectively.

TABLE 28

|  | Amount of gas generated (Relative value) | Discharge capacity maintenance rate (Relative value) |
|---|---|---|
| Example 206 | 70 | 125 |
| Example 210 | 80 | 130 |
| Comparative Example 201 | 100 | 100 |
| Comparative Example 205 | 90 | 120 |

As shown in Table 28, it is found that the ionic complex in accordance with the present invention has not only the cycle characteristics equal or greater than those of a known ionic complex (4Pa—Li) (Comparative Example 205) having a high effect of improving the cycle characteristics, but also can considerably suppress the amount of gas generated at the initial stage of cycle.

Examples 1001-1008 and Comparative Examples 1001-1004

TABLE 29

|  | Positive electrode | Negative electrode | Ionic complex |  | Nanaqueous organic solvent (Volume ratio) | | |
|---|---|---|---|---|---|---|---|
| Example 1001 | NCM | Graphite | 1Bd-Li | 1 mass % | EMC: 2 | FEC: 1 | — |
| Example 1002 |  |  |  |  | EMC: 2 | PC: 1 | — |
| Example 1003 |  |  | 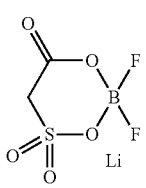 |  | EP: 2 | EC: 1 | — |
| Example 1004 |  |  |  |  | EP: 1 | EMC: 1 | EC: 1 |

TABLE 29-continued

| | Positive electrode | Negative electrode | Ionic complex | | Nanaqueous organic solvent (Volume ratio) | | |
|---|---|---|---|---|---|---|---|
| Example 1005 | | | 3Pa | 1 mass % | EMC: 2 | FEC: 1 | — |
| Example 1006 | | | | | EMC: 2 | PC: 1 | — |
| Example 1007 | | | | | EP: 2 | EC: 1 | — |
| Example 1008 | | | | | EP: 1 | EMC: 1 | EC:1 |
| Comparative Example 1001 | | | | | EMC: 2 | FEC: 1 | — |
| Comparative Example 1002 | | | | | EMC: 2 | PC: 1 | — |
| Comparative Example 1003 | | | | | EP: 2 | EC: 1 | — |
| Comparative Example 1004 | | | | | EP: 1 | EMC: 1 | EC: 1 |

Electrolytes for a nonaqueous electrolyte battery of Examples 1001, 1005 and Comparative Example 1001 were prepared in the same manner as in Examples 16, 20 and Comparative Example 11 except that a nonaqueous organic solvent is a mixed solvent of EMC:FEC=2:1 (volume ratio), respectively. These electrolytes were evaluated for the cycle characteristics at high temperature in the same manner as in Example 206. Results are shown in Table 30.

Electrolytes for a nonaqueous electrolyte battery of Examples 1002, 1006 and Comparative Example 1002 were prepared in the same manner as in Examples 16, 20 and Comparative Example 11 except that a nonaqueous organic solvent is a mixed solvent of EMC:PC=2:1 (volume ratio), respectively. These electrolytes were evaluated for the cycle characteristics at high temperature in the same manner as in Example 206. Results are shown in Table 30.

Electrolytes for a nonaqueous electrolyte battery of Examples 1003, 1007 and Comparative Example 1003 were prepared in the same manner as in Examples 16, 20 and Comparative Example 11 except that a nonaqueous organic solvent is a mixed solvent of EP:EC=2:1 (volume ratio), respectively. These electrolytes were evaluated for the cycle characteristics at high temperature in the same manner as in Example 206. Results are shown in Table 30.

Electrolytes for a nonaqueous electrolyte battery of Examples 1004, 1008 and Comparative Example 1004 were prepared in the same manner as in Examples 16, 20 and Comparative Example 11 except that a nonaqueous organic solvent is a mixed solvent of EP:EMC:EC=1:1:1 (volume ratio), respectively. These electrolytes were evaluated for the cycle characteristics at high temperature in the same manner as in Example 206. Results are shown in Table 30.

TABLE 30

| | Discharge capacity maintenance rate after 500 cycles at 60° C. |
|---|---|
| Example 1001 | 120 |
| Example 1002 | 127 |
| Example 1003 | 128 |
| Example 1004 | 130 |
| Example 1005 | 126 |
| Example 1006 | 133 |
| Example 1007 | 136 |
| Example 1008 | 135 |
| Comparative Example 1001 | 100 |
| Comparative Example 1002 | 100 |
| Comparative Example 1003 | 100 |
| Comparative Example 1004 | 100 |

Firstly, Examples 1001, 1005 and Comparative Example 1001 are compared with each other. When the discharge capacity maintenance rate when the electrolyte of Comparative Example 1001 is used is defined as 100, a relative value of the discharge capacity maintenance rate when the electrolyte of Example 1001 is used is 120, and that when the electrolyte of Example 1005 is used is 126.

Consequently, Examples 1002, 1006, and Comparative Example 1002 are compared with each other. When the discharge capacity maintenance rate when the electrolyte of Comparative Example 1002 is used is defined as 100, a relative value of the discharge capacity maintenance rate when the electrolyte of Example 1002 is used is 127, and that when the electrolyte of Example 1006 is used is 133.

Consequently, Examples 1003, 1007, and Comparative Example 1003 are compared with each other. When the discharge capacity maintenance rate when the electrolyte of Comparative Example 1003 is used is defined as 100, a relative value of the discharge capacity maintenance rate when the electrolyte of Example 1003 is used is 128, and that when the electrolyte of Example 1007 is used is 136.

Lastly, Examples 1004, 1008, and Comparative Example 1004 are compared each other. When the discharge capacity maintenance rate when the electrolyte of Comparative Example 1004 is used is defined as 100, a relative value of the discharge capacity maintenance rate when the electrolyte of Example 1004 is used is 130, and that when the electrolyte of Example 1008 is used is 135.

From these results, even when a solvent system is different, it can be said that the nonaqueous electrolyte battery including the electrolyte containing the ionic complex of Examples has higher cycle characteristics as compared with the nonaqueous electrolyte battery which does not include the ionic complex.

The above results will be summarized.

It was demonstrated that the nonaqueous electrolyte batteries including an electrolyte containing the ionic complex of Examples achieved higher cycle characteristics as compared with nonaqueous electrolyte batteries which do not include the ionic complex. The effect was found even when the content of the ionic complex was 0.01 mass %, although the effect was slight. It was demonstrated that the effect was enhanced as the content of the ionic complex was increased from 0.01 to 0.1, and further to 1 mass %. It was found that the content of the ionic complex of 3 mass % showed not only that higher cycle characteristics were obtained as compared with the case where the content was 1 mass % (Example 207 and others); but also it was hardly different from the case where the content was 1 mass % (Example 215), and that the cycle characteristics were deteriorated as compared with a case where the content was 1 mass % (Example 211).

The relationship between the types of the ionic complex and the strength of the effect of improving the cycle characteristics satisfied 3Pa>1Bd-Li>>3Ba>3Bi, 3Bf>>3Pd. When the ionic complex is 3Pa or 1Bd-Li, high cycle characteristics were obtained.

Note here that also when the ionic complex was 1Bb-Li, advantageous effects were obtained (Examples 201 to 203), but had low solubility into a nonaqueous organic solvent, and therefore comparison was not able to be carried out around 1 mass % that is presumed to be an optimum concentration.

Next results when the ionic complex is fixed to 1Bd-Li or 3Pa, and the positive electrode is fixed to NCM, while a negative electrode is changed are summarized. When the negative electrode was changed from graphite, hard carbon, silicon, to LTO, although there is difference in strength of the effect of improving the cycle characteristics, an excellent effect was found in any combinations. In particular, the high effect was found when silicon was used for the negative electrode. This is supposed to be because a protective coating made of the ionic complex (1Bd-Li or 3Pa) suppressed a large change in volume due to charge and discharge, which is the largest problem of a silicon negative electrode, to some degree. Furthermore, when the LTO negative electrode in which a volume change due to charge and discharge hardly occurs is used, the effect of improving the cycle characteristics by addition of the ionic complex (1Bd-Li or 3Pa) showed a smaller value as compared with the other negative electrodes.

Results when the ionic complex is fixed to 1Bd-Li or 3Pa, and the negative electrode is fixed to graphite, while the positive electrode is changed are summarized. When the positive electrode was changed from LCO, NCM, LFP, NCA, to LMO, although there is some differences in the strength of the effect of improving the cycle characteristics, an excellent effect was found in any combinations.

In the ionic complex 3Pa, in any of cases where the concentration of the solute $LiPF_6$ was changed from 1 M to 1.2 M (Examples 210 and 234), where the nonaqueous organic solvent was changed from EC/EMC to PC/DEC (Examples 303 and 313), where the solute was changed from $LiPF_6$ to $LiBF_4$ (Examples 210 and 238), and where solute was changed from $LiPF_6$ to LiFSI (Examples 210 and 242), the effect of improving the cycle characteristics was found to be larger than the case where the ionic complex of the present invention was not added. Furthermore, in a secondary battery system in which the cation was changed from Li to Na (Examples 901 to 904), the effect of improving the cycle characteristics was found to be larger than the case where the ionic complex of the present invention was not added.

Furthermore, even when the solvent system is different, the nonaqueous electrolyte battery including an electrolyte containing the ionic complex of Examples achieves higher cycle characteristics as compared with a nonaqueous electrolyte battery which does not include the ionic complex (Examples 1001 to 1008).

From the above mention, addition of the ionic complex of the present invention can improve the durability at high temperature (cycle characteristics) of the nonaqueous electrolyte battery regardless of the positive electrode, negative electrode, solute, and nonaqueous organic solvent.

Second Embodiment

Electrolyte for Nonaqueous Electrolyte Battery Further Containing Second Compound (Fluorine-Containing Compound) in Addition to Specific Ionic Complex
[1] Electrolytes Nos. A (1) to A (68)
[Preparation of Electrolytes Nos. A (1) to A (68)]

To a nonaqueous organic solvent including EMC and EC in a volume ratio of EMC:EC=2:1, $LiPF_6$ as a solute was added so that the concentration was 1 mol/L, 1Bd-Li synthesized in Example 2 as an ionic complex was added so that the concentration was 1 mass %, and a compound shown in Table 31 as a second compound was added so that the concentration was as described in Table 31. The solute, the ionic complex, and the second compound were mixed sequentially in this order, and the mixture was stirred for one hour to obtain electrolytes for a nonaqueous electrolyte battery in accordance with the electrolytes Nos. A (1) to A (68). In Table 31, the second compounds are metal salts of various negative ions shown in Table 32. For example, in the electrolyte No. A (1), the type of the second compound is 9-1-Li. This means a lithium salt of the negative ion 9-1 described in Table 32.

Note here that in Table 31, the second compound of Example A1-(10) is 9-2-N1 in which the cation is tetraethyl ammonium, and the second compound of Example A1-(11) is 9-2-P1 in which the cation is tetraethyl phosphonium. Furthermore, all preparation of electrolytes hereinafter was carried out while the liquid temperature was maintained at 40° C. or less.
[Evaluation]

An aluminum laminate outer package cell (capacity: 300 mAh) was fabricated by the same procedure as in Example 206 except that the electrolytes Nos. A (1) to A (68) were used as the electrolyte, and similarly, the degree of deterioration of a cell was evaluated based on the amount of gas generated after 10 cycles and the discharge capacity maintenance rate after 500 cycles (evaluation of the amount of gas generated and the cycle characteristics). Values are shown in Table 31, as relative values when the amount of gas generated and the discharge capacity maintenance rate in Comparative Example 201 are defined 100, respectively.

Furthermore, similar to the evaluation of the amount of gas generated, the output characteristics at low temperature were evaluated using cells after 10 cycles. That is to say, after 10 cycles, the cells were cooled to 25° C. and discharged to 3.0 V, and then charged at −20° C. at 0.2 C rate to 4.3 V, and 4.3 V was maintained for one hour. Furthermore, discharging was carried out at −20° C., at 5 C rate to 3.0 V, and discharge capacity at −20° C. was measured. Results are shown in Table 31. Note here that numerical values of discharge capacity (−20° C.) described in Table 31 are relative values when the discharge capacity (−20° C.) of Comparative Example 201 is defined as 100. It is suggested that the larger the value is, the more excellent the output characteristics at low temperature are.

From the results shown in Table 31, it is found that Examples A1-(1) to A1-(68) using the electrolytes Nos. A (1) to A (68) further including the second compound in addition to a specific ionic complex show not only the amount of gas generated equal to that in Example 206 and the cycle characteristics equal to or not less than those in Example 206, but also improvement of the output characteristics at low temperature.

TABLE 31

| Electrolyte No. | Evaluation | Positive electrode | Negative electrode | Ionic complex | Second compound Type | mass % | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|
| A(1) | Example | A1-(1) | NCM Graphite | | 9-1-Li | 0.2 | 70 | 127 | 128 |
| A(2) | | A1-(2) | | | " | 0.5 | 70 | 135 | 129 |
| A(3) | | A1-(3) | | | " | 1 | 70 | 146 | 130 |
| A(4) | | A1-(4) | | | 9-1-Na | 1 | 70 | 143 | 129 |
| A(5) | | A1-(5) | | | 10-1-Li | 0.2 | 70 | 127 | 128 |
| A(6) | | A1-(6) | | | " | 0.5 | 70 | 137 | 129 |
| A(7) | | A1-(7) | | | " | 1 | 70 | 152 | 133 |
| A(8) | | A1-(8) | | | 10-1Na | 1 | 70 | 152 | 132 |
| A(9) | | A1-(9) | | | 10-1-K | 1 | 70 | 150 | 131 |
| A(10) | | A1-(10) | | 1Bd-Li 1 mass % | 10-1-N1 | 1 | 70 | 147 | 129 |
| A(11) | | A1-(11) | | | 10-1-P1 | 1 | 70 | 148 | 128 |
| A(12) | | A1-(12) | | | 10-2-Li | 1 | 70 | 154 | 130 |
| A(13) | | A1-(13) | | | 10-3-Li | 1 | 70 | 155 | 129 |
| A(14) | | A1-(14) | | | 1-3-Na | 1 | 70 | 153 | 129 |
| A(15) | | A1-(15) | | | 10-4-Li | 1 | 70 | 150 | 129 |
| A(16) | | A1-(16) | | | 10-5-Li | 1 | 70 | 152 | 129 |
| A(17) | | A1-(17) | | | 10-6-Li | 1 | 70 | 154 | 131 |
| A(18) | | A1-(18) | | | 10-7-Li | 1 | 70 | 155 | 128 |
| A(19) | | A1-(19) | | | 10-8-Li | 1 | 70 | 152 | 128 |
| A(20) | | A1-(20) | | | 10-9-Li | 1 | 70 | 146 | 128 |
| A(21) | | A1-(21) | | | 10-10-Li | 1 | 70 | 127 | 128 |
| A(22) | | A1-(22) | | | 11-1-Li | 0.2 | 70 | 133 | 128 |
| A(23) | | A1-(23) | | | " | 0.5 | 70 | 144 | 129 |
| A(24) | | A1-(24) | | | " | 1 | 70 | 143 | 131 |
| A(25) | | A1-(25) | | | 11-1-Na | 1 | 70 | 148 | 130 |
| A(26) | | A1-(26) | | | 11-2-Li | 1 | 70 | 149 | 129 |
| A(27) | | A1-(27) | | | 11-3-Li | 1 | 70 | 148 | 128 |
| A(28) | | A1-(28) | | | 11-3-Na | 1 | 70 | 147 | 128 |
| A(29) | | A1-(29) | | | 11-4-Li | 1 | 70 | 152 | 129 |
| A(30) | | A1-(30) | | | 11-5-Li | 1 | 70 | 150 | 129 |
| A(31) | | A1-(31) | | | 11-5-Na | 1 | 70 | 147 | 128 |
| A(32) | | A1-(32) | | | 11-6-Li | 1 | 70 | 140 | 128 |
| A(33) | | A1-(33) | | | 11-7-Li | 1 | 70 | 127 | 128 |
| A(34) | | A1-(34) | | | 12-1-Li | 0.2 | 70 | 136 | 127 |
| A(35) | | A1-(35) | | | " | 0.5 | 70 | 144 | 128 |
| A(36) | | A1-(36) | | | " | 1 | 70 | 142 | 129 |
| A(37) | | A1-(37) | | | 12-1-Na | 1 | 70 | 128 | 129 |
| A(38) | | A1-(38) | | | 12-2-Li | 1 | 70 | 127 | 128 |
| A(39) | | A1-(39) | | | 12-3-Li | 1 | 70 | 128 | 128 |
| A(40) | | A1-(40) | | | 12-4-Li | 1 | 70 | 126 | 128 |
| A(41) | | A1-(41) | | | 12-4-Na | 1 | 70 | 127 | 126 |
| A(42) | | A1-(42) | | | 12-5-Li | 1 | 70 | 130 | 128 |
| A(43) | | A1-(43) | | | 13-1-Li | 0.2 | 70 | 138 | 128 |
| A(44) | | A1-(44) | | | " | 0.5 | 70 | 154 | 129 |
| A(45) | | A1-(45) | | | " | 1 | 70 | 153 | 131 |
| A(46) | | A1-(46) | | | 13-1-Na | 1 | 70 | 147 | 130 |
| A(47) | | A1-(47) | | | 13-2-Li | 1 | 70 | 151 | 129 |
| A(48) | | A1-(48) | | | 13-3-Li | 1 | 70 | 143 | 129 |
| A(49) | | A1-(49) | | | 13-4-Li | 1 | 70 | 124 | 129 |
| A(50) | | A1-(50) | | | 15-1-Li | 0.2 | 70 | 133 | 127 |
| A(51) | | A1-(51) | | | " | 0.5 | 70 | 145 | 128 |
| A(52) | | A1-(52) | | | " | 1 | 70 | 143 | 129 |
| A(53) | | A1-(53) | | | 15-1-Na | 1 | 70 | 137 | 129 |
| A(54) | | A1-(54) | | | 15-2-Li | 1 | 70 | 127 | 128 |
| A(55) | | A1-(55) | | | 15-3-Li | 1 | 70 | 125 | 128 |
| A(56) | | A1-(56) | | | 15-4-Li | 1 | 70 | 126 | 128 |
| A(57) | | A1-(57) | | | 15-5-Li | 1 | 70 | 124 | 128 |
| A(58) | | A1-(58) | | | 14-1-Li | 0.2 | 70 | 133 | 127 |
| A(59) | | A1-(59) | | | " | 0.5 | 70 | 141 | 128 |
| A(60) | | A1-(60) | | | " | 1 | 70 | 140 | 129 |
| A(61) | | A1-(61) | | | 14-1-Na | 1 | 70 | 126 | 129 |
| A(62) | | A1-(62) | | | 14-2-Li | 1 | 70 | 126 | 128 |
| A(63) | | A1-(63) | | | 14-3-Li | 1 | 70 | 128 | 128 |
| A(64) | | A1-(64) | | | 14-4-Li | 1 | 70 | 125 | 128 |
| A(65) | | A1-(65) | | | 16-1-Li | 0.2 | 70 | 125 | 127 |

TABLE 31-continued

| Electrolyte No. | Evaluation | Positive electrode | Negative electrode | Ionic complex | Second compound Type | mass % | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|
| A(66) | A1-(66) | | | | " | 0.5 | 70 | 125 | 128 |
| A(67) | A1-(67) | | | | " | 1 | 70 | 125 | 128 |
| A(68) | A1-(68) | | | | 16-1-Na | 1 | 70 | 125 | 127 |
| Example 16 | Example 206 | NCM | Graphite | 1Bd-Li | 1 mass % | — | — | 70 | 125 | 125 |
| Comparative Example 11 | Comparative Example 201 | NCM | Graphite | — | — | — | 100 | 100 | 100 |

TABLE 32

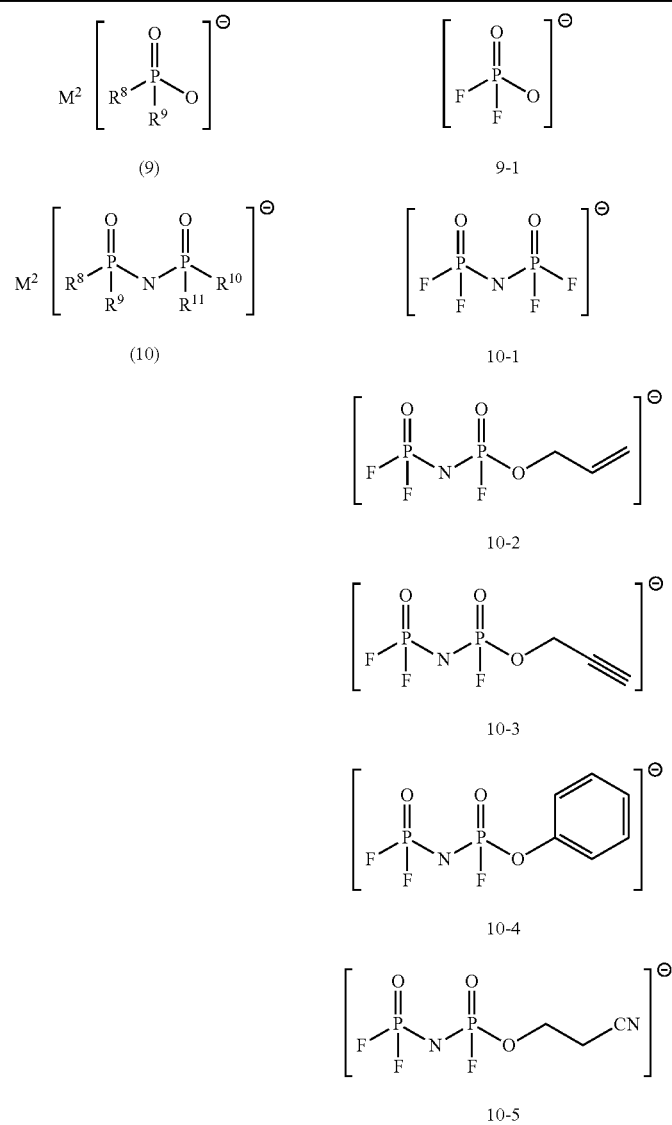

TABLE 32-continued

TABLE 32-continued
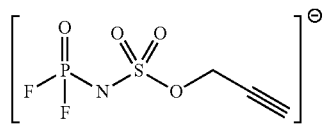
11-5
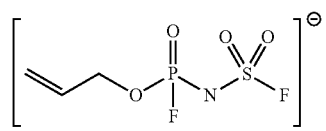
11-6
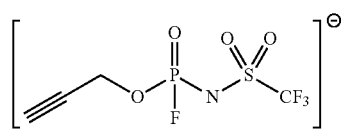
11-7
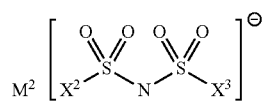
(12)
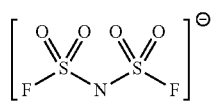
12-1
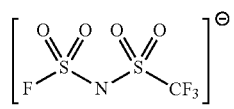
12-2
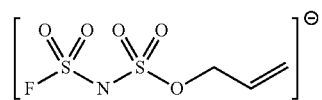
12-3
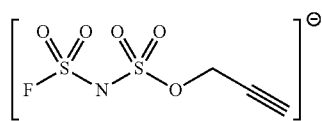
12-4
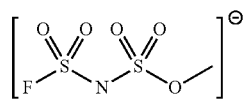
12-5

TABLE 32-continued
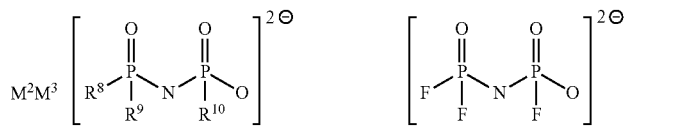
(13)            13-1
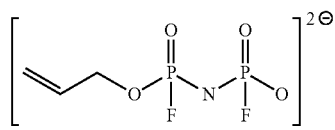
13-2
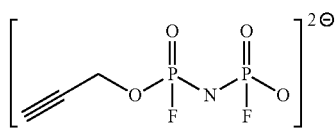
13-3
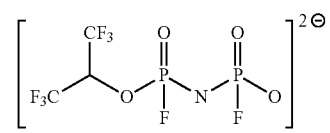
13-4
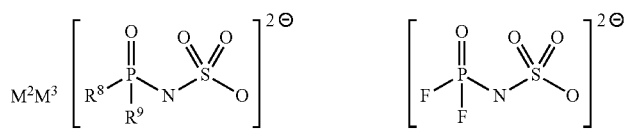
(14)            14-1
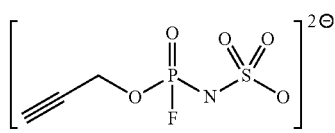
14-2
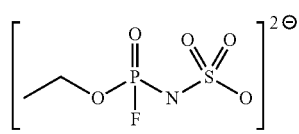
14-3
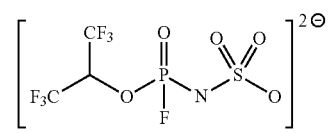
14-4

TABLE 32-continued

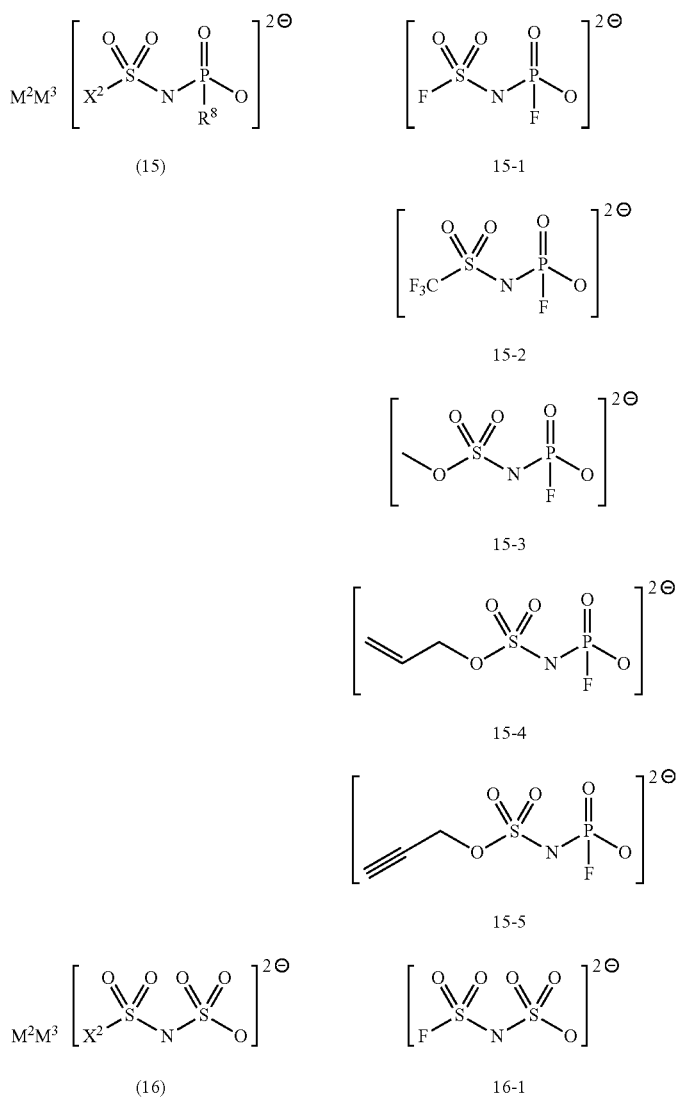

[2] Electrolytes Nos. A(69) to A(80)
[Preparation of Electrolyte Nos. A 69) to A(80)]

To a nonaqueous organic solvent including DEC and PC in a volume ratio of DEC:PC=2:1, NaPF$_6$ as a solute was added so that the concentration was 1 mol/L, 1Bd-Na synthesized in Example 3 as an ionic complex was added so that the concentration was 1 mass %, and a compound shown in Table 33 as a second compound was added so that the concentration was as described in Table 33. The solute, the ionic complex, and the second compound were mixed sequentially in this order, and the mixture was stirred for one hour to obtain the electrolytes for a nonaqueous electrolyte battery in accordance with the electrolytes Nos. A (69) to A (80). In Table 33, the second compounds are metal salts of various negative ions shown in Table 32.

[Evaluation]

An aluminum laminate outer package cell (capacity: 300 mAh) was fabricated by the same procedure as in Example 901 except that the electrolytes Nos. A(69) to A(80) were used as the electrolyte, and similarly, the degree of deterioration of a cell was evaluated based on the amount of gas generated after 10 cycles and the discharge capacity maintenance rate after 200 cycles (evaluation of the amount of gas generated and the cycle characteristics). Note here that in charging, the voltage reached 3.8 V and then was maintained at 3.8 V for one hour. Discharge was carried out to 1.5 V. Thus, the charge/discharge cycle was repeated. Values are shown in Table 33, as relative values when the amount of gas generated and the discharge capacity maintenance rate in Comparative Example 901 are defined 100, respectively.

Furthermore, similar to the evaluation of the amount of gas generated, the output characteristics at low temperature were evaluated using cells after 10 cycles. That is to say, after 10 cycles, the cells were cooled to 25° C. and discharged to 3.0 V, and then charged at −20° C. at 0.2 C rate to 3.8 V, and 3.8 V was maintained for one hour. Furthermore, discharging was carried out at −20° C. at 5 C rate to 1.5 V, and discharge capacity at −20° C. was measured. Note here that numerical values of discharge capacity (−20° C.)

described in Table 33 are relative values when the discharge capacity (−20° C.) of Comparative Example 901 is defined as 100.

From the results shown in Table 33, it is found that even in the case of a sodium ion battery, Examples A1-(69) to A1-(80) using the electrolytes Nos. A(69) to A(80) further including the second compound in addition to the specific ionic complex show not only the amount of gas generated equal to that in Example 901 and the cycle characteristics equal to or not less than those in Example 901, but also improvement of the output characteristics at low temperature.

210 except that the electrolytes Nos. A(81) to A(148) were used as the electrolyte, and similarly, the degree of deterioration of a cell was evaluated based on the amount of gas generated after 10 cycles and the discharge capacity maintenance rate after 500 cycles (evaluation of the amount of gas generated and the cycle characteristics). Values are shown in Table 34, as the relative values when the amount of gas generated and the discharge capacity maintenance rate in Comparative Example 201 are defined 100, respectively.

Furthermore, similar to the evaluation of the amount of gas generated, the output characteristics at low temperature

TABLE 33

| Electrolyte No. | Evaluation | Positive electrode | Negative electrode | Ionic complex | Second compound Type | mass % | Amount of gas generated after 10 cycles at 60° C. | Discharge capacity maintenance rate after 200 cycles at 60° C. | −20° C. discharge capacity after 10 cycles at 60° C. |
|---|---|---|---|---|---|---|---|---|---|
| A(69) | A1-(69) | NaFe$_{0.5}$Co$_{0.5}$O$_2$ | Hard carbon | (structure) | 9-1-Na | 1 | 70 | 160 | 130 |
| A(70) | A1-(70) | | | | 10-1-Na | 1 | 70 | 167 | 132 |
| A(71) | A1-(71) | | | | 10-3-Na | 1 | 70 | 170 | 129 |
| A(72) | A1-(72) | | | | 11-1-Na | 1 | 70 | 159 | 131 |
| A(73) | A1-(73) | | | | 11-3-Na | 1 | 70 | 163 | 128 |
| A(74) | A1-(74) | | | | 11-5-Na | 1 | 70 | 167 | 129 |
| A(75) | A1-(75) | | | | 12-1-Na | 1 | 70 | 158 | 128 |
| A(76) | A1-(76) | | | | 12-4-Na | 1 | 70 | 138 | 128 |
| A(77) | A1-(77) | | | | 13-1-Na | 1 | 70 | 170 | 133 |
| A(78) | A1-(78) | | | 1Bd-Na 1 mass % | 15-1-Na | 1 | 70 | 159 | 129 |
| A(79) | A1-(79) | | | | 14-1-Na | 1 | 70 | 155 | 129 |
| A(80) | A1-(80) | | | | 16-1-Na | 1 | 70 | 140 | 128 |
| Example 64 | Example 901 | | | 1Bd-Na 1 mass % | — | — | 70 | 140 | 125 |
| Comparative Example 17 | Comparative Example 901 | | | — | — | — | 100 | 100 | 100 |

[3] Electrolyte Nos. A(81) to A(148)
[Preparation of Electrolyte Nos. A(81) to A(148)]

To a nonaqueous organic solvent including EMC and EC in a volume ratio of EMC:EC=2:1, LiPF$_6$ as a solute was added so that the concentration was 1 mol/L, 3Pa synthesized in Example 4 as an ionic complex was added so that the concentration was 1 mass %, and a compound shown in Table 34 as a second compound was added so that the concentration was as described in Table 34. The solute, the ionic complex, and the second compound were mixed sequentially in this order, and the mixture was stirred for one hour to obtain the electrolytes for a nonaqueous electrolyte battery in accordance with the electrolytes Nos. A(81) to A(148). In Table 34, the second compounds are metal salts of various negative ions shown in Table 32.
[Evaluation]

An aluminum laminate outer package cell (capacity: 300 mAh) was fabricated by the same procedure as in Example were evaluated using cells after 10 cycles. That is to say, after 10 cycles, the cells were cooled to 25° C. and discharged to 3.0 V, and then charged at −20° C. at 0.2 C rate to 4.3 V, and 4.3 V was maintained for one hour. Furthermore, discharging was carried out at −20° C., at 5 C rate to 3.0 V, and discharge capacity at −20° C. was measured. Note here that numerical values of discharge capacity (−20° C.) described in Table 34 are relative values when the discharge capacity (−20° C.) of Comparative Example 201 is defined as 100.

From the results shown in Table 34, even when the type of the specific ionic complex is changed, it is found that Examples A1-(81) to A1-(148) using the electrolytes Nos. A(81) to A(148) further including the second compound in addition to the specific ionic complex show not only the amount of gas generated equal to that in Example 210 and the cycle characteristics equal to or not less than those in Example 210, but also improvement of the output characteristics at low temperature.

TABLE 34

| Electrolyte No. | Evaluation | Positive electrode | Negative electrode | Ionic complex | Second compound Type | mass % | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|
| A(81) | Example | A1-(81) | NCM | Graphite | 9-1-Li | 0.2 | 80 | 131 | 123 |
| A(82) | | A1-(82) | | | " | 0.5 | 80 | 143 | 124 |
| A(83) | | A1-(83) | | | " | 1 | 80 | 152 | 125 |
| A(84) | | A1-(84) | | | 9-1-Na | 1 | 80 | 150 | 124 |
| A(85) | | A1-(85) | | | 10-1-Li | 0.2 | 80 | 132 | 123 |
| A(86) | | A1-(86) | | | " | 0.5 | 80 | 144 | 124 |
| A(87) | | A1-(87) | | | " | 1 | 80 | 159 | 128 |
| A(88) | | A1-(88) | | | 10-1-Na | 1 | 80 | 158 | 127 |
| A(89) | | A1-(89) | | 3Pa  1 mass % | 10-1-K | 1 | 80 | 156 | 126 |
| A(90) | | A1-(90) | | | 10-1-N1 | 1 | 80 | 152 | 124 |
| A(91) | | A1-(91) | | | 10-1-P1 | 1 | 80 | 151 | 123 |
| A(92) | | A1-(92) | | | 10-2-Li | 1 | 80 | 158 | 125 |
| A(93) | | A1-(93) | | | 10-3-Li | 1 | 80 | 162 | 124 |
| A(94) | | A1-(94) | | | 10-3-Na | 1 | 80 | 159 | 124 |
| A(95) | | A1-(95) | | | 10-4-Li | 1 | 80 | 154 | 124 |
| A(96) | | A1-(96) | | | 10-5-Li | 1 | 80 | 159 | 124 |
| A(97) | | A1-(97) | | | 10-6-Li | 1 | 80 | 160 | 126 |
| A(98) | | A1-(98) | | | 10-7-Li | 1 | 80 | 162 | 123 |
| A(99) | | A1-(99) | | | 10-8-Li | 1 | 80 | 156 | 123 |
| A(100) | | A1-(100) | | | 10-9-Li | 1 | 80 | 155 | 123 |
| A(101) | | A1-(101) | | | 10-10-Li | 1 | 80 | 154 | 123 |
| A(102) | | A1-(102) | | | 11-1-Li | 0.2 | 80 | 132 | 123 |
| A(103) | | A1-(103) | | | " | 0.5 | 80 | 138 | 124 |
| A(104) | | A1-(104) | | | " | 1 | 80 | 149 | 126 |
| A(105) | | A1-(105) | | | 11-1-Na | 1 | 80 | 149 | 125 |
| A(106) | | A1-(106) | | | 11-2-Li | 1 | 80 | 154 | 124 |
| A(107) | | A1-(107) | | | 11-3-Li | 1 | 80 | 155 | 123 |
| A(108) | | A1-(108) | | | 11-3-Na | 1 | 80 | 154 | 123 |
| A(109) | | A1-(109) | | | 11-4-Li | 1 | 80 | 153 | 124 |
| A(110) | | A1-(110) | | | 11-5-Li | 1 | 80 | 158 | 124 |
| A(111) | | A1-(111) | | | 11-5-Na | 1 | 80 | 156 | 123 |
| A(112) | | A1-(112) | | | 11-6-Li | 1 | 80 | 153 | 123 |
| A(113) | | A1-(113) | | | 11-7-Li | 1 | 80 | 146 | 123 |
| A(114) | | A1-(114) | | | 12-1-Li | 0.2 | 80 | 132 | 122 |
| A(115) | | A1-(115) | | | " | 0.5 | 80 | 140 | 123 |
| A(116) | | A1-(116) | | | " | 1 | 80 | 149 | 124 |
| A(117) | | A1-(117) | | | 12-1-Na | 1 | 80 | 148 | 124 |
| A(118) | | A1-(118) | | | 12-2-Li | 1 | 80 | 133 | 123 |
| A(119) | | A1-(119) | | | 12-3-Li | 1 | 80 | 132 | 123 |
| A(120) | | A1-(120) | | | 12-4-Li | 1 | 80 | 134 | 122 |
| A(121) | | A1-(121) | | | 12-4-Na | 1 | 80 | 133 | 121 |
| A(122) | | A1-(122) | | | 12-5-Li | 1 | 80 | 132 | 123 |
| A(123) | | A1-(123) | | | 13-1Li | 0.2 | 80 | 136 | 123 |
| A(124) | | A1-(124) | | | " | 0.5 | 80 | 145 | 124 |
| A(125) | | A1-(125) | | | " | 1 | 80 | 159 | 126 |
| A(126) | | A1-(126) | | | 13-1-Na | 1 | 80 | 160 | 125 |
| A(127) | | A1-(127) | | | 13-2-Li | 1 | 80 | 153 | 124 |
| A(128) | | A1-(128) | | | 13-3-Li | 1 | 80 | 157 | 124 |
| A(129) | | A1-(129) | | | 13-4-Li | 1 | 80 | 149 | 124 |
| A(130) | | A1-(130) | | | 15-1-Li | 0.2 | 80 | 128 | 122 |
| A(131) | | A1-(131) | | | " | 0.5 | 80 | 138 | 123 |
| A(132) | | A1-(132) | | | " | 1 | 80 | 151 | 124 |
| A(133) | | A1-(133) | | | 15-1-Na | 1 | 80 | 149 | 124 |
| A(134) | | A1-(134) | | | 15-2-Li | 1 | 80 | 143 | 123 |
| A(135) | | A1-(135) | | | 15-3-Li | 1 | 80 | 132 | 123 |
| A(136) | | A1-(136) | | | 15-4-Li | 1 | 80 | 130 | 123 |
| A(137) | | A1-(137) | | | 15-5-Li | 1 | 80 | 132 | 123 |
| A(138) | | A1-(138) | | | 14-1-Li | 0.2 | 80 | 131 | 122 |
| A(139) | | A1-(139) | | | " | 0.5 | 80 | 138 | 123 |
| A(140) | | A1-(140) | | | " | 1 | 80 | 147 | 124 |
| A(141) | | A1-(141) | | | 14-1-Na | 1 | 80 | 146 | 124 |
| A(142) | | A1-(142) | | | 14-2-Li | 1 | 80 | 130 | 123 |
| A(143) | | A1-(143) | | | 14-3-Li | 1 | 80 | 131 | 123 |
| A(144) | | A1-(144) | | | 14-4-Li | 1 | 80 | 133 | 123 |

TABLE 34-continued

| Electrolyte No. | Evaluation | Positive electrode | Negative electrode | Ionic complex | Second compound Type | Second compound mass % | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|
| A(145) | A1-(145) | | | | 16-1-Li | 0.2 | 80 | 130 | 122 |
| A(146) | A1-(146) | | | | " | 0.5 | 80 | 130 | 123 |
| A(147) | A1-(147) | | | | " | 1 | 80 | 130 | 123 |
| A(148) | A1-(148) | | | | 16-1-Na | 1 | 80 | 130 | 122 |
| Example 20 | Example 210 | NCM | Graphite | 3Pa | 1 mass % | — | — | 80 | 130 | 120 |
| Comparative Example 11 | Comparative Example 201 | NCM | Graphite | — | — | — | 100 | 100 | 100 |

[4] Electrolytes Nos. A(149) to A(154)
[Preparation of Electrolytes Nos. A(149) to A(154)]

To a nonaqueous organic solvent including DEC and PC in a volume ratio of DEC:PC=2:1, NaPF$_6$ as a solute was added so that the concentration was 1 mol/L, 3Pa synthesized in Example 4 as an ionic complex was added so that the concentration was 1 mass %, and a compound shown in Table 35 as a second compound was added so that the concentration was as described in Table 35. The solute, the ionic complex, and the second compound were mixed sequentially in this order, and the mixture was stirred for one hour to obtain the electrolytes for a nonaqueous electrolyte battery in accordance with the electrolytes Nos. A (149) to A (154). In Table 35, the second compounds are metal salts of various negative ions shown in Table 32.

[Evaluation]

An aluminum laminate outer package cell (capacity: 300 mAh) was fabricated by the same procedure as in Example 902 except that the electrolytes Nos. A(149) to A(154) were used as the electrolyte, and similarly, the degree of deterioration of a cell was evaluated based on the amount of gas generated after 10 cycles and the discharge capacity maintenance rate after 200 cycles (evaluation of the amount of gas generated and the cycle characteristics). Note here that in charging, the voltage reached 3.8 V and then was maintained at 3.8 V for one hour. Discharge was carried out to 1.5 V. Thus, the charge/discharge cycle was repeated. Values are shown in Table 35, as relative values when the amount of gas generated and the discharge capacity maintenance rate in Comparative Example 901 are defined 100, respectively.

Furthermore, similar to the evaluation of the amount of gas generated, the output characteristics at low temperature were evaluated using cells after 10 cycles. That is to say, after 10 cycles, the cells were cooled to 25° C. and discharged to 3.0 V, and then charged at −20° C. at 0.2 C rate to 3.8 V, and 3.8 V was maintained for one hour. Furthermore, discharging was carried out at −20° C., at 5 C rate to 1.5 V, and discharge capacity at −20° C. was measured. Note here that numerical values of discharge capacity (−20° C.) described in Table 35 are relative values when the discharge capacity (−20° C.) of Comparative Example 901 is defined as 100.

From the results shown in Table 35, in the case of a sodium ion battery, it is found that Examples A1-(149) to A1-(154) using the electrolytes Nos. A(149) to A(154) further including the second compound in addition to the ionic complex show the amount of gas generated equal to that in Example 902 and further show improved cycle characteristics and output characteristics at low temperature.

TABLE 35

| Electrolyte No. | Evaluation | Positive electrode | Negative electrode | Ionic complex | | Second compound Type | Second compound mass % | Amount of gas generated after 10 cycles at 60° C. | Discharge capacity maintenance rate after 200 cycles at 60° C. | −20° C. discharge capacity after 10 cycles at 60° C. |
|---|---|---|---|---|---|---|---|---|---|---|
| A(149) | A1-(149) | NaFe$_{0.5}$Co$_{0.5}$O$_2$ | Hard carbon | 3Pa | 1 mass % | 9-1-Li | 1 | 75 | 153 | 127 |
| A(150) | A1-(150) | | | | | 10-1-Li | 1 | 75 | 159 | 128 |
| A(151) | A1-(151) | | | | | 11-1-Li | 1 | 75 | 146 | 128 |
| A(152) | A1-(152) | | | | | 11-3-Li | 1 | 75 | 154 | 125 |
| A(153) | A1-(153) | | | | | 12-1-Li | 1 | 75 | 146 | 125 |
| A(154) | A1-(154) | | | | | 13-1-Li | 1 | 75 | 164 | 128 |
| Example 68 | Example 902 | | | 3Pa | 1 mass % | — | — | 75 | 150 | 120 |
| Comparative Example 17 | Comparative Example 901 | | | — | — | — | — | 100 | 100 | 100 |

[5] Various Combinations of Specific Ionic Complex and Second Compound

Hereinafter, electrolytes having typical combinations of an ionic complex and a second compound and concentration were evaluated while the types of positive electrodes, negative electrodes, and the like, are varied. For reference, list of combinations of the positive electrodes and the negative electrodes used in all the Examples and Comparative Examples of the present invention and evaluation conditions are shown in Table 36.

TABLE 36

| Positive electrode | Negative electrode | Evaluation of cycle characteristics and amount of gas generated (At the time of 10th cycle) | | | Evaluation of output characteristics at low temperature (After 10 cycles) | | |
|---|---|---|---|---|---|---|---|
| | | Current density [mA/cm$^2$] (Both charge and discharge) | Charge end voltage [V] | Discharge end voltage [V] | Discharge rate | Charge end voltage [V] | Discharge end voltage [V] |
| LCO | Graphite | 0.3 | 4.2 | 3.0 | 5C | 4.2 | 3.0 |
| NCM | Graphite | 0.3 | 4.3 | 3.0 | 5C | 4.3 | 3.0 |
| NCM | Hard carbon | 0.3 | 4.2 | 2.2 | 5C | 4.2 | 2.2 |
| NCM | Silicon | 0.3 | 4.2 | 3.0 | 5C | 4.2 | 3.0 |
| NCM | LTO | 0.3 | 2.8 | 1.5 | 5C | 2.8 | 1.5 |
| LFP | Graphite | 0.3 | 4.1 | 2.5 | 5C | 4.1 | 2.5 |
| NCA | Graphite | 0.3 | 4.3 | 3.0 | 5C | 4.3 | 3.0 |
| LMO | Graphite | 0.3 | 4.2 | 3.0 | 5C | 4.2 | 3.0 |
| NaFe$_{0.5}$Co$_{0.5}$O$_2$ | Hard carbon | 0.3 | 3.8 | 1.5 | 5C | 3.8 | 1.5 |

The above-mentioned evaluation results are shown in Tables 37 and 38. Note here that it is demonstrated that electrolytes other than the electrolytes having the combination of an ionic complex and a second compound and the concentration mentioned below show the same tendency as mentioned above.

In Table 37, in each battery configuration, the values of the amount of gas generated, the discharge capacity maintenance rate, and the discharge capacity (−20° C.) of Examples using the electrolytes Nos. A(3), A(7), A(24), A(27), A(36), and A(45) are respectively shown as relative values when the amount of gas generated, the discharge capacity maintenance rate, and the discharge capacity (−20° C.) in Comparative Examples using the electrolyte of Comparative Example 11 in the corresponding battery configuration are defined 100. From the above-mentioned results, it is found that even when the types of the positive electrode and the negative electrode are changed, Examples using electrolytes Nos. A(3), A(7), A(24), A(27), A(36), and A(45), which further include the second compound in addition to the ionic complex, show not only the amount of gas generated equal to that in Example using the electrolyte of Example 16 and the cycle characteristics equal to or not less than the electrolyte of Example 16, but also improvement of the output characteristics at low temperature.

In Table 38, in each battery configuration, the values of the amount of gas generated, the discharge capacity maintenance rate, and the discharge capacity (−20° C.) of Examples using the electrolytes Nos. A(83), A(87), A(104), A(107), A(116), and A(125) are respectively shown as relative values when the amount of gas generated, the discharge capacity maintenance rate, and the discharge capacity (−20° C.) in Comparative Examples using the electrolyte of Comparative Example 11 in the corresponding battery configuration are defined 100.

From the above-mentioned results, it is found that even when the types of the positive electrode and the negative electrode are changed, Examples using electrolytes Nos. A(83), A(87), A(104), A(107), A(116), and A(125), which further include the second compound in addition to the ionic complex, not only show the amount of gas generated equal to that in Example using the electrolyte of Example 20 and the cycle characteristics equal to or not less than the electrolyte of Example 16, but also improves the output characteristics at low temperature.

TABLE 37

| Electrolyte No. | Evaluation | Positive electrode | Negative electrode | Ionic complex | Second compound Type | mass % | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|
| A(3) | A2-(3) | NCM | Hard carbon | 1Bd-Li 1 mass % | 9-1-Li | 1 | 65 | 150 | 131 |
| A(7) | A2-(7) | | | | 10-1-Li | 1 | 65 | 156 | 134 |
| A(24) | A2-(24) | | | | 11-1-Li | 1 | 65 | 143 | 133 |
| A(27) | A2-(27) | | | | 11-3-Li | 1 | 65 | 150 | 129 |
| A(36) | A2-(36) | | | | 12-1-Li | 1 | 65 | 143 | 129 |
| A(45) | A2-(45) | | | | 13-1-Li | 1 | 65 | 160 | 134 |
| Example 16 | Example A2-16 | | | 1Bd-Li 1 mass % | — | — | 65 | 128 | 126 |
| Comparative Example 11 | Comparative Example A2-11 | | | — | — | — | 100 | 100 | 100 |
| A(3) | A3-(3) | NCM | Silicon | 1Bd-Li 1 mass % | 9-1-Li | 1 | 70 | 352 | 272 |
| A(7) | A3-(7) | | | | 10-1-Li | 1 | 70 | 361 | 277 |
| A(24) | A3-(24) | | | | 11-1-Li | 1 | 70 | 355 | 278 |
| A(27) | A3-(27) | | | | 11-3-Li | 1 | 70 | 351 | 270 |
| A(36) | A3-(36) | | | | 12-1-Li | 1 | 70 | 351 | 268 |
| A(45) | A3-(45) | | | | 13-1-Li | 1 | 70 | 350 | 283 |
| Example 16 | Example A3-16 | | | 1Bd-Li 1 mass % | — | — | 70 | 350 | 260 |
| Comparative Example 11 | Comparative Example A3-11 | | | — | — | — | 100 | 100 | 100 |
| A(3) | A4-(3) | NCM | LTO | 1Bd-Li 1 mass % | 9-1-Li | 1 | 80 | 112 | 110 |
| A(7) | A4-(7) | | | | 10-1-Li | 1 | 80 | 116 | 115 |
| A(24) | A4-(24) | | | | 11-1-Li | 1 | 80 | 115 | 115 |
| A(27) | A4-(27) | | | | 11-3-Li | 1 | 80 | 111 | 112 |
| A(36) | A4-(36) | | | | 12-1-Li | 1 | 80 | 110 | 112 |
| A(45) | A4-(45) | | | | 13-1-Li | 1 | 80 | 110 | 113 |
| Example 16 | Example A4-16 | | | 1Bd-Li 1 mass % | — | — | 80 | 110 | 105 |
| Comparative Example 11 | Comparative Example A4-11 | | | — | — | — | 100 | 100 | 100 |
| A(3) | A5-(3) | LFP | Graphite | 1Bd-Li 1 mass % | 9-1-Li | 1 | 70 | 125 | 127 |
| A(7) | A5-(7) | | | | 10-1-Li | 1 | 70 | 131 | 130 |
| A(24) | A5-(24) | | | | 11-1-Li | 1 | 70 | 123 | 130 |
| A(27) | A5-(27) | | | | 11-3-Li | 1 | 70 | 127 | 126 |
| A(36) | A5-(36) | | | | 12-1-Li | 1 | 70 | 120 | 124 |
| A(45) | A5-(45) | | | | 13-1-Li | 1 | 70 | 125 | 128 |

TABLE 37-continued

| Electrolyte No. | Evaluation | Positive electrode | Negative electrode | Ionic complex | | Second compound Type | mass % | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|---|
| Example 16 | Example A5-16 | | | 1Bd-Li | 1 mass % | — | — | 70 | 122 | 120 |
| Comparative Example 11 | Comparative Example A5-11 | | | — | — | — | — | 100 | 100 | 100 |
| A(3) | A6-(3) | NCA | Graphite | 1Bd-Li | 1 mass % | 9-1-Li | 1 | 65 | 149 | 130 |
| A(7) | A6-(7) | | | | | 10-1-Li | 1 | 65 | 155 | 133 |
| A(24) | A6-(24) | | | | | 11-1-Li | 1 | 65 | 152 | 131 |
| A(27) | A6-(27) | | | | | 11-3-Li | 1 | 65 | 147 | 128 |
| A(36) | A6-(36) | | | | | 12-1-Li | 1 | 65 | 147 | 128 |
| A(45) | A6-(45) | | | | | 13-1-Li | 1 | 65 | 163 | 131 |
| Example 16 | Example A6-16 | | | 1Bd-Li | 1 mass % | — | — | 65 | 120 | 125 |
| Comparative Example 11 | Comparative Example A6-11 | | | — | — | — | — | 100 | 100 | 100 |
| A(3) | A7-(3) | LMO | Graphite | 1Bd-Li | 1 mass % | 9-1-Li | 1 | 60 | 144 | 125 |
| A(7) | A7-(7) | | | | | 10-1-Li | 1 | 60 | 123 | 128 |
| A(24) | A7-(24) | | | | | 11-1-Li | 1 | 60 | 138 | 126 |
| A(27) | A7-(27) | | | | | 11-3-Li | 1 | 60 | 120 | 124 |
| A(36) | A7-(36) | | | | | 12-1-Li | 1 | 60 | 122 | 124 |
| A(45) | A7-(45) | | | | | 13-1-Li | 1 | 60 | 143 | 129 |
| Example 16 | Example A7-16 | | | 1Bd-Li | 1 mass % | — | — | 60 | 115 | 112 |
| Comparative Example 11 | Comparative Example A7-11 | | | — | — | — | — | 100 | 100 | 100 |
| A(3) | A8-(3) | LCO | Graphite | 1Bd-Li | 1 mass % | 9-1-Li | 1 | 75 | 142 | 121 |
| A(7) | A8-(7) | | | | | 10-1-Li | 1 | 75 | 149 | 124 |
| A(24) | A8-(24) | | | | | 11-1-Li | 1 | 75 | 144 | 123 |
| A(27) | A8-(27) | | | | | 11-3-Li | 1 | 75 | 139 | 119 |
| A(36) | A8-(36) | | | | | 12-1-Li | 1 | 75 | 137 | 119 |
| A(45) | A8-(45) | | | | | 13-1-Li | 1 | 75 | 134 | 124 |
| Example 16 | Example A8-16 | | | 1Bd-Li | 1 mass % | — | — | 75 | 120 | 115 |
| Comparative Example 11 | Comparative Example A8-11 | | | — | — | — | — | 100 | 100 | 100 |

TABLE 38

| Electrolyte No. | Evaluation | Positive electrode | Negative electrode | Ionic complex | | Second compound Type | mass % | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|---|
| A(83) | Example A2-(83) | NCM | Hard carbon | 3Pa | 1 mass % | 9-1-Li | 1 | 75 | 154 | 127 |
| A(87) | A2-(87) | | | | | 10-1-Li | 1 | 75 | 161 | 129 |
| A(104) | A2-(104) | | | | | 11-1-Li | 1 | 75 | 147 | 128 |
| A(107) | A2-(107) | | | | | 11-3-Li | 1 | 75 | 154 | 125 |
| A(116) | A2-(116) | | | | | 12-1-Li | 1 | 75 | 147 | 125 |
| A(125) | A2-(125) | | | | | 13-1-Li | 1 | 75 | 165 | 129 |

TABLE 38-continued

| Electrolyte No. | Evaluation | Positive electrode | Negative electrode | Ionic complex | Second compound Type | mass % | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|
| Example 20 | Example A2-20 | | | 3Pa 1 mass % | — | — | 75 | 132 | 121 |
| Comparative Example 11 | Comparative Example A2-11 | | | — | — | — | 100 | 100 | 100 |
| A(83) | A3-(83) | NCM | Silicon | 3Pa 1 mass % | 9-1-Li | 1 | 80 | 381 | 250 |
| A(87) | A3-(87) | | | | 10-1-Li | 1 | 80 | 384 | 252 |
| A(104) | A3-(104) | | | | 11-1-Li | 1 | 80 | 388 | 252 |
| A(107) | A3-(107) | | | | 11-3-Li | 1 | 80 | 381 | 245 |
| A(116) | A3-(116) | | | | 12-1-Li | 1 | 80 | 381 | 242 |
| A(125) | A3-(125) | | | | 13-1-Li | 1 | 80 | 390 | 254 |
| Example 20 | Example A3-20 | | | 3Pa 1 mass % | — | — | 80 | 380 | 240 |
| Comparative Example 11 | Comparative Example A3-11 | | | — | — | — | 100 | 100 | 100 |
| A(83) | A4-(83) | NCM | LTO | 3Pa 1 mass % | 9-1-Li | 1 | 90 | 116 | 105 |
| A(87) | A4-(87) | | | | 10-1-Li | 1 | 90 | 120 | 105 |
| A(104) | A4-(104) | | | | 11-1-Li | 1 | 90 | 119 | 105 |
| A(107) | A4-(107) | | | | 11-3-Li | 1 | 90 | 115 | 104 |
| A(116) | A4-(116) | | | | 12-1-Li | 1 | 90 | 113 | 104 |
| A(125) | A4-(125) | | | | 13-1-Li | 1 | 90 | 113 | 104 |
| Example 20 | Example A4-20 | | | 3Pa 1 mass % | — | — | 90 | 113 | 103 |
| Comparative Example 11 | Comparative Example A4-11 | | | — | — | — | 100 | 100 | 100 |
| A(83) | A5-(83) | LFP | Graphite | 3Pa 1 mass % | 9-1-Li | 1 | 80 | 126 | 120 |
| A(87) | A5-(87) | | | | 10-1-Li | 1 | 80 | 131 | 122 |
| A(104) | A5-(104) | | | | 11-1-Li | 1 | 80 | 124 | 122 |
| A(107) | A5-(107) | | | | 11-3-Li | 1 | 80 | 127 | 118 |
| A(116) | A5-(116) | | | | 12-1-Li | 1 | 80 | 120 | 117 |
| A(125) | A5-(125) | | | | 13-1-Li | 1 | 80 | 126 | 121 |
| Example 20 | Example A5-20 | | | 3Pa 1 mass % | — | — | 80 | 123 | 115 |
| Comparative Example 11 | Comparative Example A5-11 | | | — | — | — | 100 | 100 | 100 |
| A(83) | A6-(83) | NCA | Graphite | 3Pa 1 mass % | 9-1-Li | 1 | 75 | 156 | 125 |
| A(87) | A6-(87) | | | | 10-1-Li | 1 | 75 | 162 | 127 |
| A(104) | A6-(104) | | | | 11-1-Li | 1 | 75 | 159 | 126 |
| A(107) | A6-(107) | | | | 11-3-Li | 1 | 75 | 154 | 122 |
| A(116) | A6-(116) | | | | 12-1-Li | 1 | 75 | 153 | 122 |
| A(125) | A6-(125) | | | | 13-1-Li | 1 | 75 | 170 | 126 |

TABLE 38-continued

| Electrolyte No. | | Evaluation | Positive electrode | Negative electrode | Ionic complex | Second compound Type | mass % | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|---|
| Example | 20 | Example A6-20 | | | 3Pa | 1 mass % | — | — | 75 | 125 | 120 |
| Comparative Example | 11 | Comparative Example A6-11 | | | — | — | — | — | 100 | 100 | 100 |
| | A(83) | A7-(83) | LMO | Graphite | 3Pa 1 mass % | 9-1-Li | 1 | 70 | 147 | 113 |
| | A(87) | A7-(87) | | | | 10-1-Li | 1 | 70 | 126 | 116 |
| | A(104) | A7-(104) | | | | 11-1-Li | 1 | 70 | 141 | 114 |
| | A(107) | A7-(107) | | | | 11-3-Li | 1 | 70 | 123 | 112 |
| | A(116) | A7-(116) | | | | 12-1-Li | 1 | 70 | 125 | 112 |
| | A(125) | A7-(125) | | | | 13-1-Li | 1 | 70 | 146 | 117 |
| Example | 20 | Example A7-20 | | | 3Pa | 1 mass % | — | — | 70 | 117 | 109 |
| Comparative Example | 11 | Comparative Example A7-11 | | | — | — | — | — | 100 | 100 | 100 |
| | A(83) | A8-(83) | LCO | Graphite | 3Pa 1 mass % | 9-1-Li | 1 | 85 | 149 | 118 |
| | A(87) | A8-(87) | | | | 10-1-Li | 1 | 85 | 156 | 120 |
| | A(104) | A8-(104) | | | | 11-1-Li | 1 | 85 | 151 | 119 |
| | A(107) | A8-(107) | | | | 11-3-Li | 1 | 85 | 146 | 115 |
| | A(116) | A8-(116) | | | | 12-1-Li | 1 | 85 | 144 | 115 |
| | A(125) | A8-(125) | | | | 13-1-Li | 1 | 85 | 141 | 120 |
| Example | 20 | Example A8-20 | | | 3Pa | 1 mass % | — | — | 85 | 125 | 112 |
| Comparative Example | 11 | Comparative Example A8-11 | | | — | — | — | — | 100 | 100 | 100 |

Third Embodiment

Electrolyte for Nonaqueous Electrolyte Battery Further Containing Third Compound $(Si(R^{12})_x(R^{13})_{4-x})$ in Addition to Specific Ionic Complex

[1] Electrolytes Nos. B(1) to B(21)

[Preparation of Electrolytes Nos. B(1) to B(21)]

To a nonaqueous organic solvent including EMC and EC in a volume ratio of EMC:EC=2:1, LiPF$_6$ as a solute was added so that the concentration was 1 mol/L, 1Bd-Li synthesized in Example 2 as an ionic complex was added so that the concentration was 1 mass %, and a compound shown in Table 39 as a third compound was added so that the concentration was as described in Table 39. The solute, the ionic complex, and the third compound were mixed sequentially in this order, and the mixture was stirred for one hour to obtain electrolytes for a nonaqueous electrolyte battery in accordance with the electrolytes Nos. B(1) to B(21). In Table 39, the third compounds are compounds shown in Table 40. Note here that all preparation of electrolytes hereinafter was carried out while the liquid temperature was maintained at 40° C. or less.

[Evaluation]

An aluminum laminate outer package cell (capacity: 300 mAh) was fabricated by the same procedure as in Example 206 except that the electrolytes Nos. B(1) to B(21) were used as the electrolyte, and similarly, the degree of deterioration of a cell was evaluated based on the amount of gas generated after 10 cycles and the discharge capacity maintenance rate after 500 cycles (evaluation of the amount of gas generated and the cycle characteristics). Values are shown in Table 39, as relative values when the amount of gas generated and the discharge capacity maintenance rate in Comparative Example 201 are defined 100, respectively.

From the results shown in Table 39, it is found that Examples B1-(1) to B1-(21) using the electrolytes Nos. B(1) to B(21) further including the third compound in addition to the ionic complex can further improve the reduction of the amount of gas generated and the cycle characteristics as compared with Example 206.

TABLE 39

| Electrolyte No. | Evaluation | Positive electrode | Negative electrode | Ionic complex | Third compound Type | Third compound mass % | Amount of gas generated after 10 cycles at 60° C. | Discharge capacity maintenance rate after 500 cycles at 60° C. |
|---|---|---|---|---|---|---|---|---|
| B(1) | Example | NCM | Graphite | 1Bd-Li  1 mass % | 17-2 | 0.5 | 55 | 143 |
| B(2) | B1-(2) | | | | 17-5 | 0.2 | 60 | 152 |
| B(3) | B1-(3) | | | | " | 0.5 | 50 | 165 |
| B(4) | B1-(4) | | | | " | 1 | 45 | 168 |
| B(5) | B1-(5) | | | | 17-6 | 0.5 | 60 | 144 |
| B(6) | B1-(6) | | | | 17-8 | 0.5 | 60 | 140 |
| B(7) | B1-(7) | | | | 17-10 | 0.5 | 60 | 148 |
| B(8) | B1-(8) | | | | 17-11 | 0.5 | 60 | 140 |
| B(9) | B1-(9) | | | | 17-12 | 0.2 | 60 | 155 |
| B(10) | B1-(10) | | | | " | 0.5 | 50 | 167 |
| B(11) | B1-(11) | | | | " | 1 | 45 | 169 |
| B(12) | B1-(12) | | | | 17-13 | 0.5 | 60 | 138 |
| B(13) | B1-(13) | | | | 17-14 | 0.5 | 60 | 137 |
| B(14) | B1-(14) | | | | 17-15 | 0.5 | 60 | 135 |
| B(15) | B1-(15) | | | | 17-16 | 0.5 | 60 | 132 |
| B(16) | B1-(16) | | | | 17-22 | 0.5 | 60 | 130 |
| B(17) | B1-(17) | | | | 17-23 | 0.5 | 60 | 130 |
| B(18) | B1-(18) | | | | 17-4 | 0.5 | 55 | 150 |
| B(19) | B1-(19) | | | | 17-1 | 0.2 | 60 | 150 |
| B(20) | B1-(20) | | | | " | 0.5 | 50 | 160 |
| B(21) | B1-(21) | | | | " | 1 | 45 | 162 |
| Example 16 | Example 206 | | | | — | — | 70 | 125 |
| Comparative Example 11 | Comparative Example 201 | | | — | — | — | 100 | 100 |

TABLE 40

$Si(R^{12})_x(R^{13})_{4-x}$ (17)

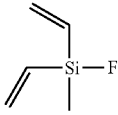

17-1

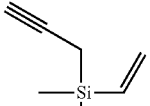

17-2

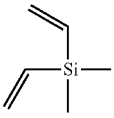

17-4

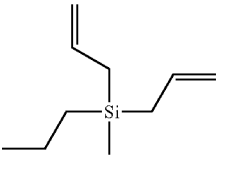

17-5

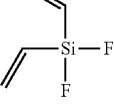

17-6

TABLE 40-continued

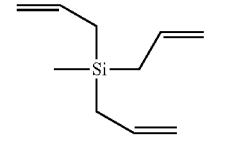

17-8

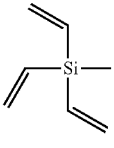

17-10

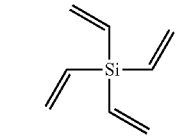

17-11

17-12

TABLE 40-continued 17-13

17-14

17-15

17-16

17-22

17-23

[2] Electrolytes Nos. B(22) to B(24)
[Preparation of Electrolytes Nos. B(22) to B(24)]

To a nonaqueous organic solvent including DEC and PC in a volume ratio of DEC:PC=2:1, NaPF$_6$ as a solute was added so that the concentration was 1 mol/L, 1Bd-Na synthesized in Example 3 as an ionic complex was added so that the concentration was 1 mass %, and a compound shown in Table 41 as the third compound was added so that the concentration was as descried in Table 41. The solute, the ionic complex, and the third compound were mixed sequentially in this order, and the mixture was stirred for one hour to obtain the electrolytes for a nonaqueous electrolyte battery. In Table 41, the third compounds are compounds shown in Table 40.

[Evaluation]

An aluminum laminate outer package cell (capacity: 300 mAh) was fabricated by the same procedure as in Example 901 except that the electrolytes Nos. B(22) to B(24) were used as the electrolyte, and similarly, the degree of deterioration of a cell was evaluated based on the amount of gas generated after 10 cycles and the discharge capacity maintenance rate after 200 cycles (evaluation of amount of gas generated and cycle characteristics). Note here that in charging, the voltage reached 3.8 V and then was maintained at 3.8 V for one hour. Discharge was carried out to 1.5 V. Thus, the charge/discharge cycle was repeated. Values are shown in Table 41, as relative values when the amount of gas generated and the discharge capacity maintenance rate in Comparative Example 901 are defined 100, respectively.

From the results shown in Table 41, even in the case of a sodium ion battery, it is found that Examples B1-(22) to B1-(24) using the electrolytes Nos. B(22) to B(24) further including the third compound in addition to the ionic complex can further improve the reduction of the amount of gas generated and the cycle characteristics as compared with Example 901.

TABLE 41

| Electrolyte No. | Evaluation | Positive electrode | Negative electrode | Ionic complex | Third compound Type | mass % | Amount of gas generated after 10 cycles at 60° C. | Discharge capacity maintenance rate after 200 cycles at 60° C. |
|---|---|---|---|---|---|---|---|---|
| B(22) | B1-(22) | NaFe$_{0.5}$ | Hard carbon | 1Bd-Na  1 mass % | 17-5 | 0.5 | 50 | 174 |
| B(23) | B1-(23) | Co$_{0.5}$O$_2$ | | | 17-12 | 0.5 | 50 | 175 |
| B(24) | B1-(24) | | | | 17-1 | 0.5 | 50 | 168 |
| Example 64 | Example 901 | | | | | | 70 | 140 |
| Comparative Example 17 | Comparative Example 901 | | | — | — | — | 100 | 100 |

[3] Electrolytes Nos. B(25) to B(45)
[Preparation of Electrolytes Nos. B(25) to B(45)]

To a nonaqueous organic solvent including EMC and EC in a volume ratio of EMC:EC=2:1, $LiPF_6$ as a solute was added so that the concentration was 1 mol/L, 3Pa synthesized in Example 4 as an ionic complex was added so that the concentration was 1 mass %, and a compound shown in Table 42 as a third compound was added so that the concentration was as described in Table 42. The solute, the ionic complex, and the third compound were mixed sequentially in this order, and the mixture was stirred for one hour to obtain the electrolytes for a nonaqueous electrolyte battery.

[Evaluation]

An aluminum laminate outer package cell (capacity: 300 mAh) was fabricated by the same procedure as in Example 210 except that the electrolytes Nos. B(25) to B(45) were used as the electrolyte, and similarly, the degree of deterioration of a cell was evaluated based on the amount of gas generated after 10 cycles and the discharge capacity maintenance rate after 500 cycles (evaluation of the amount of gas generated and the cycle characteristics). Values are shown in Table 42, as relative values when the amount of gas generated and the discharge capacity maintenance rate in Comparative Example 201 are defined 100, respectively.

From the results shown in Table 42, it is found that even when the types of the ionic complex are changed, Examples B1-(25) to B1-(45) using the electrolytes Nos. B(25) to B(45) further including the third compound in addition to the ionic complex can further improve the reduction of the amount of gas generated and the cycle characteristics as compared with Example 210.

[4] Electrolytes Nos. B(46) to B(48)
[Preparation of Electrolytes Nos. B(46) to B(48)]

To a nonaqueous organic solvent including DEC and PC in a volume ratio of DEC:PC=2:1, $NaPF_6$ as a solute was added so that the concentration was 1 mol/L, 3Pa synthesized in Example 4 as an ionic complex was added so that the concentration was 1 mass %, and a compound shown in Table 43 as the third compound was added so that the concentration was as described in Table 43. The solute, the ionic complex, and the third compound were mixed sequentially in this order, and the mixture was stirred for one hour to obtain the electrolytes for a nonaqueous electrolyte battery.

[Evaluation]

An aluminum laminate outer package cell (capacity: 300 mAh) was fabricated by the same procedure as in Example 902 except that the electrolytes Nos. B(46) to B(48) were used as the electrolyte, and similarly, the degree of deterioration of a cell was evaluated based on the amount of gas generated after 10 cycles and the discharge capacity maintenance rate after 200 cycles (evaluation of amount of gas generated and cycle characteristics). Note here that in charging, the voltage reached 3.8 V and then was maintained at 3.8 V for one hour. Discharge was carried out to 1.5 V. Thus, the charge/discharge cycle was repeated. Values are shown in Table 43, as relative values when the amount of gas generated and the discharge capacity maintenance rate in Comparative Example 901 are defined 100, respectively.

From the results shown in Table 43, even in the case of a sodium ion battery, it is found that Examples B1-(46) to B1-(48) using the electrolytes Nos. B(46) to B(48) further including the third compound in addition to the ionic complex can further improve the reduction of the amount of gas generated and the cycle characteristics as compared with Example 902.

TABLE 42

| Electrolyte No. | Evaluation | Positive electrode | Negative electrode | Ionic complex | Third compound Type | mass % | Amount of gas generated after 10 cycles at 60° C. | Discharge capacity maintenance rate after 500 cycles at 60° C. |
|---|---|---|---|---|---|---|---|---|
| B(25) | Example B1-(25) | NCM | Graphite | 3PA  1 mass % 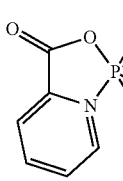 | 17-2 | 0.5 | 65 | 149 |
| B(26) | B1-(26) | | | | 17-5 | 0.2 | 70 | 158 |
| B(27) | B1-(27) | | | | " | 0.5 | 60 | 172 |
| B(28) | B1-(28) | | | | " | 1 | 50 | 175 |
| B(29) | B1-(29) | | | | 17-6 | 0.5 | 70 | 150 |
| B(30) | B1-(30) | | | | 17-8 | 0.5 | 70 | 146 |
| B(31) | B1-(31) | | | | 17-10 | 0.5 | 70 | 154 |
| B(32) | B1-(32) | | | | 17-11 | 0.5 | 70 | 146 |
| B(33) | B1-(33) | | | | 17-12 | 0.2 | 70 | 161 |
| B(34) | B1-(34) | | | | " | 0.5 | 55 | 174 |
| B(35) | B1-(35) | | | | " | 1 | 50 | 177 |
| B(36) | B1-(36) | | | | 17-13 | 0.5 | 70 | 144 |
| B(37) | B1-(37) | | | | 17-14 | 0.5 | 70 | 142 |
| B(38) | B1-(38) | | | | 17-15 | 0.5 | 70 | 140 |
| B(39) | B1-(39) | | | | 17-16 | 0.5 | 70 | 137 |
| B(40) | B1-(40) | | | | 17-22 | 0.5 | 70 | 135 |
| B(41) | B1-(41) | | | | 17-23 | 0.5 | 70 | 135 |
| B(42) | B1-(42) | | | | 17-4 | 0.5 | 65 | 156 |
| B(43) | B1-(43) | | | | 17-1 | 0.2 | 70 | 156 |
| B(44) | B1-(44) | | | | " | 0.5 | 55 | 166 |
| B(45) | B1-(45) | | | | " | 1 | 50 | 168 |
| Example 20 | Example 210 | | | | — | — | 80 | 130 |
| Comparative Example 11 | Comparative Example 201 | | | — | — | — | 100 | 100 |

TABLE 43

| Electrolyte No. | | Evaluation | | Positive electrode | Negative electrode | Ionic complex | | Third compound Type | mass % | Amount of gas generated after 10 at 60° C. | Discharge capacity maintenance rate after 200 cycles at 60° C. |
|---|---|---|---|---|---|---|---|---|---|---|---|
| | B(46) | | B1-(46) | NaFe$_{0.5}$Co$_{0.5}$O$_2$ | Hard carbon | 3Pa | 1 mass % | 17-5 | 0.5 | 55 | 180 |
| | B(47) | | B1-(47) | | | | | 17-12 | 0.5 | 55 | 178 |
| | B(48) | | B1-(48) | | | | | 17-1 | 0.5 | 55 | 175 |
| Example | 68 | Example | 902 | | | — | — | — | — | 75 | 150 |
| Comparative Example | 17 | Comparative Example | 901 | | | — | — | — | — | 100 | 100 |

[5] Various Combinations of Specific Ionic Complex and Third Compound

Hereinafter, electrolytes having typical combinations of a specific ionic complex and a third compound and concentration were evaluated while the types of positive electrodes, negative electrodes, and the like, are varied. The combinations of positive and negative electrodes and evaluation conditions are as shown in Table 36.

The above-mentioned evaluation results are shown in Tables 44 and 45. Note here that it is demonstrated that electrolytes other than the electrolytes having the combination of an ionic complex and a third compound and the concentration mentioned below show the same tendency as mentioned above.

In Table 44, in each battery configuration, the values of the amount of gas generated, and the discharge capacity maintenance rate of Examples using the electrolytes Nos. B(3), B(10), and B(20) are respectively shown as relative values when the amount of gas generated and the discharge capacity maintenance rate in Comparative Examples using the electrolyte of Comparative Example 11 in the corresponding battery configuration are defined 100. From the results mentioned above, even when the types of the positive electrode and the negative electrode are changed, it is found that Examples using electrolytes Nos. B(3), B(10), and B(20), which further include the third compound in addition to the ionic complex, can further improve the reduction of the amount of gas generated and the cycle characteristics as compared with Example using the electrolyte of Example 16.

In Table 45, in each battery configuration, the values of the amount of gas generated, and the discharge capacity maintenance rate of Examples using the electrolytes Nos. B(27), B(34), and B(44) are respectively shown as relative values when the amount of gas generated, and the discharge capacity maintenance rate in Comparative Examples using the electrolyte of Comparative Example 11 in the corresponding battery configuration are defined 100.

From the results mentioned above, even when the types of the positive electrode and the negative electrode are changed, it is found that Examples using electrolytes Nos. B(27), B(34), and B(44), which further include the third compound in addition to the ionic complex, can further improve the reduction of the amount of gas generated and the cycle characteristics as compared with Example using the electrolyte of Example 20.

TABLE 44

| Electrolyte No. | | Evaluation | | Positive electrode | Negative electrode | Ionic complex | | Third compound Type | mass % | Amount of gas generated after 10 cycles at 60° C. | Discharge capacity maintenance rate after 500 cycles at 60° C. |
|---|---|---|---|---|---|---|---|---|---|---|---|
| | B(3) | | B2-(3) | NCM | Hard carbon | 1Bd-Li | 1 mass % | 17-5 | 0.5 | 45 | 167 |
| | B(10) | | B2-(10) | | | | | 17-12 | 0.5 | 45 | 170 |
| | B(20) | | B2-(20) | | | | | 17-1 | 0.5 | 50 | 165 |
| Example | 16 | Example | A2-16 | | | | | — | — | 65 | 128 |
| Comparative Example | 11 | Comparative Example | A2-11 | | | — | — | — | — | 100 | 100 |
| | B(3) | | B3-(3) | NCM | シリコン | 1Bd-Li | 1 mass % | 17-5 | 0.5 | 55 | 392 |
| | B(10) | | B3-(10) | | | | | 17-12 | 0.5 | 55 | 388 |
| | B(20) | | B3-(20) | | | | | 17-1 | 0.5 | 65 | 360 |
| Example | 16 | Example | A3-16 | | | | | — | — | 70 | 350 |
| Comparative Example | 11 | Comparative Example | A3-11 | | | — | — | — | — | 100 | 100 |
| | B(3) | | B4-(3) | NCM | LTO | 1Bd-Li | 1 mass % | 17-5 | 0.5 | 70 | 120 |
| | B(10) | | B4-(10) | | | | | 17-12 | 0.5 | 70 | 118 |
| | B(20) | | B4-(20) | | | | | 17-1 | 0.5 | 70 | 111 |

TABLE 44-continued

Ionic complex structure (shown in header):
$$\text{1Bd-Li: cyclic structure with } O=C, O, B(F)(F), O, S(=O)(=O), \text{Li}$$

| Electrolyte No. | | Evaluation | | Positive electrode | Negative electrode | Ionic complex | | Third compound Type | mass % | Amount of gas generated after 10 cycles at 60° C. | Discharge capacity maintenance rate after 500 cycles at 60° C. |
|---|---|---|---|---|---|---|---|---|---|---|---|
| Example | 16 | Example | A4-16 | | | — | | — | — | 80 | 110 |
| Comparative Example | 11 | Comparative Example | A4-11 | | | — | | — | — | 100 | 100 |
| | B(3) | | B5-(3) | LFP | Graphite | 1Bd-Li | 1 mass % | 17-5 | 0.5 | 50 | 161 |
| | B(10) | | B5-(10) | | | | | 17-12 | 0.5 | 50 | 162 |
| | B(20) | | B5-(20) | | | | | 17-1 | 0.5 | 50 | 155 |
| Example | 16 | Example | A5-16 | | | — | | — | — | 70 | 122 |
| Comparative Example | 11 | Comparative Example | A5-11 | | | — | | — | — | 100 | 100 |
| | B(3) | | B6-(3) | NCA | Graphite | 1Bd-Li | 1 mass % | 17-5 | 0.5 | 50 | 158 |
| | B(10) | | B6-(10) | | | | | 17-12 | 0.5 | 50 | 160 |
| | B(20) | | B6-(20) | | | | | 17-1 | 0.5 | 55 | 153 |
| Example | 16 | Example | A6-16 | | | — | | — | — | 65 | 120 |
| Comparative Example | 11 | Comparative Example | A6-11 | | | — | | — | — | 100 | 100 |
| | B(3) | | B7-(3) | LMO | Graphite | 1Bd-Li | 1 mass % | 17-5 | 0.5 | 45 | 152 |
| | B(10) | | B7-(10) | | | | | 17-12 | 0.5 | 45 | 153 |
| | B(20) | | B7-(20) | | | | | 17-1 | 0.5 | 45 | 148 |
| Example | 16 | Example | A7-16 | | | — | | — | — | 60 | 115 |
| Comparative Example | 11 | Comparative Example | A7-11 | | | — | | — | — | 100 | 100 |
| | B(3) | | B8-(3) | LCO | Graphite | 1Bd-Li | 1 mass % | 17-5 | 0.5 | 60 | 157 |
| | B(10) | | B8-(10) | | | | | 17-12 | 0.5 | 60 | 157 |
| | B(20) | | B8-(20) | | | | | 17-1 | 0.5 | 60 | 154 |
| Example | 16 | Example | A8-16 | | | — | | — | — | 75 | 120 |
| Comparative Example | 11 | Comparative Example | A8-11 | | | — | | — | — | 100 | 100 |

TABLE 45

Ionic complex structure (shown in header): 3Pa — pyridine-carboxylate coordinated with $PF_4$

| Electrolyte No. | | Evaluation | | Positive electrode | Negative electrode | Ionic complex | | Third compound Type | mass % | Amount of gas generated after 10 cycles at 60° C. | Discharge capacity maintenance rate after 500 cycles at 60° C. |
|---|---|---|---|---|---|---|---|---|---|---|---|
| | B(27) | Example | B2-(27) | NCM | Hard carbon | 3Pa | 1 mass % | 17-5 | 0.5 | 55 | 175 |
| | B(34) | | B2-(34) | | | | | 17-12 | 0.5 | 50 | 177 |
| | B(44) | | B2-(44) | | | | | 17-1 | 0.5 | 50 | 169 |
| Example | 20 | Example | A2-20 | | | — | | — | — | 75 | 132 |
| Comparative Example | 11 | Comparative Example | A2-11 | | | — | | — | — | 100 | 100 |
| | B(27) | | B3-(27) | NCM | Silicon | 3Pa | 1 mass % | 17-5 | 0.5 | 60 | 401 |
| | B(34) | | B3-(34) | | | | | 17-12 | 0.5 | 55 | 415 |
| | B(44) | | B3-(44) | | | | | 17-1 | 0.5 | 60 | 385 |
| Example | 20 | Example | A3-20 | | | — | | — | — | 80 | 380 |
| Comparative Example | 11 | Comparative Example | A3-11 | | | — | | — | — | 100 | 100 |
| | B(27) | | B4-(27) | NCM | LTO | 3Pa | 1 mass % | 17-5 | 0.5 | 70 | 150 |
| | B(34) | | B4-(34) | | | | | 17-12 | 0.5 | 70 | 151 |
| | B(44) | | B4-(44) | | | | | 17-1 | 0.5 | 75 | 165 |

TABLE 45-continued

| Electrolyte No. | | Evaluation | | Positive electrode | Negative electrode | Ionic complex | Third compound Type | mass % | Amount of gas generated after 10 cycles at 60° C. | Discharge capacity maintenance rate after 500 cycles at 60° C. |
|---|---|---|---|---|---|---|---|---|---|---|
| Example | 20 | Example | A4-20 | | | | — | — | 90 | 113 |
| Comparative Example | 11 | Comparative Example | A4-11 | — | | — | — | — | 100 | 100 |
| | B(27) | | B5-(27) | LFP | Graphite | 3Pa  1 mass % | 17-5 | 0.5 | 60 | 163 |
| | B(34) | | B5-(34) | | | | 17-12 | 0.5 | 60 | 166 |
| | B(44) | | B5-(44) | | | | 17-1 | 0.5 | 65 | 156 |
| Example | 20 | Example | A5-20 | | | | — | — | 80 | 123 |
| Comparative Example | 11 | Comparative Example | A5-11 | — | | — | — | — | 100 | 100 |
| | B(27) | | B6-(27) | NCA | Graphite | 3Pa  1 mass % | 17-5 | 0.5 | 55 | 165 |
| | B(34) | | B6-(34) | | | | 17-12 | 0.5 | 50 | 167 |
| | B(44) | | B6-(44) | | | | 17-1 | 0.5 | 60 | 159 |
| Example | 20 | Example | A6-20 | | | | — | — | 75 | 125 |
| Comparative Example | 11 | Comparative Example | A6-11 | — | | — | — | — | 100 | 100 |
| | B(27) | | B7-(27) | LMO | Graphite | 3Pa  1 mass % | 17-5 | 0.5 | 55 | 155 |
| | B(34) | | B7-(34) | | | | 17-12 | 0.5 | 50 | 157 |
| | B(44) | | B7-(44) | | | | 17-1 | 0.5 | 55 | 149 |
| Example | 20 | Example | A7-20 | | | | — | — | 70 | 117 |
| Comparative Example | 11 | Comparative Example | A7-11 | — | | — | — | — | 100 | 100 |
| | B(27) | | B8-(27) | LCO | Graphite | 3Pa  1 mass % | 17-5 | 0.5 | 70 | 164 |
| | B(34) | | B8-(34) | | | | 17-12 | 0.5 | 70 | 167 |
| | B(44) | | B8-(44) | | | | 17-1 | 0.5 | 75 | 160 |
| Example | 20 | Example | A8-20 | | | | — | — | 85 | 125 |
| Comparative Example | 11 | Comparative Example | A8-11 | — | | — | — | — | 100 | 100 |

Fourth Embodiment

Electrolyte for Nonaqueous Electrolyte Battery Further Containing Fourth Compound (Cyclic Sulfonic Acid Compound) in Addition to Specific Ionic Complex
[1] Electrolytes Nos. C(1) to C(18)
[Preparation of Electrolytes Nos. C(1) to C(18)]

To a nonaqueous organic solvent including EMC and EC in a volume ratio of EMC:EC=2:1, LiPF$_6$ as a solute was added so that the concentration was 1 mol/L, 1Bd-Li synthesized in Example 2 as an ionic complex was added so that the concentration was 1 mass %, and a compound shown in Table 46 as a fourth compound was added so that the concentration was as described in Table 46. The solute, the ionic complex, and the fourth compound were mixed sequentially in this order, and the mixture was stirred for one hour to obtain electrolytes for a nonaqueous electrolyte battery. In Table 46, the fourth compounds are compounds shown in Table 47. Note here that all preparation of electrolytes hereinafter was carried out while the liquid temperature was maintained at 40° C. or less.
[Evaluation]

An aluminum laminate outer package cell (capacity: 300 mAh) was fabricated by the same procedure as in Example 206 except that the electrolytes Nos. C(1) to C(18) were used as the electrolyte, and similarly, the degree of deterioration of a cell was evaluated based on the amount of gas generated after 10 cycles and the discharge capacity maintenance rate after 500 cycles (evaluation of the amount of gas generated and the cycle characteristics). Values are shown in Table 46, as relative values when the amount of gas generated and the discharge capacity maintenance rate in Comparative Example 201 are defined 100, respectively.

Furthermore, similar to the evaluation of the amount of gas generated, the output characteristics at low temperature were evaluated using cells after 10 cycles. That is to say, after 10 cycles, the cells were cooled to 25° C. and discharged to 3.0 V, and then charged at −20° C. at 0.2 C rate to 4.3 V, and 4.3 V was maintained for one hour. Furthermore, discharging was carried out at −20° C., at 5 C rate to 3.0 V, and discharge capacity at −20° C. was measured. The larger the value is, the more excellent the output characteristics at low temperature are. Note here that numerical values of discharge capacity (−20° C.) described in Table 46 are relative values when the discharge capacity (−20° C.) of Comparative Example 201 is defined as 100.

From the results shown in Table 46, it is found that Examples C1-(1) to C1-(18) using the electrolytes Nos. C(1) to C(18) further including the fourth compound in addition to the ionic complex can further improve at least one of the reduction of the amount of gas generated, the cycle characteristics, and the output characteristics at low temperature as compared with Example 206.

TABLE 46

| Electrolyte No. | Evaluation | Positive electrode | Negative electrode | Ionic complex | Fourth compound Type | mass % | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|
| C(1) | Example | C1-(1) | NCM | Graphite | PS | 0.5 | 70 | 127 | 125 |
| C(2) | | C1-(2) | | | " | 1 | 70 | 131 | 128 |
| C(3) | | C1-(3) | | | " | 2 | 70 | 133 | 130 |
| C(4) | | C1-(4) | | | 1,3-PRS | 0.2 | 70 | 126 | 125 |
| C(5) | | C1-(5) | | | " | 0.5 | 65 | 130 | 125 |
| C(6) | | C1-(6) | | | " | 1 | 65 | 135 | 125 |
| C(7) | | C1-(7) | | | PEGLST | 0.2 | 70 | 126 | 126 |
| C(8) | | C1-(8) | | | " | 0.5 | 70 | 129 | 129 |
| C(9) | | C1-(9) | | 1Bd-Li 1 mass % | " | 1 | 70 | 134 | 132 |
| C(10) | | C1-(10) | | | 19-1 | 0.2 | 70 | 126 | 128 |
| C(11) | | C1-(11) | | | " | 0.5 | 65 | 133 | 133 |
| C(12) | | C1-(12) | | | " | 1 | 60 | 138 | 136 |
| C(13) | | C1-(13) | | | 19-15 | 0.2 | 70 | 126 | 127 |
| C(14) | | C1-(14) | | | " | 0.5 | 65 | 134 | 132 |
| C(15) | | C1-(15) | | | " | 1 | 60 | 140 | 135 |
| C(16) | | C1-(16) | | | 20-1 | 0.2 | 70 | 126 | 128 |
| C(17) | | C1-(17) | | | " | 0.5 | 65 | 134 | 134 |
| C(18) | | C1-(18) | | | " | 1 | 60 | 139 | 137 |
| Example 16 | Example | 206 | | | — | — | 70 | 125 | 125 |
| Comparative Example 11 | Comparative Example | 201 | | — | — | — | 100 | 100 | 100 |

TABLE 47

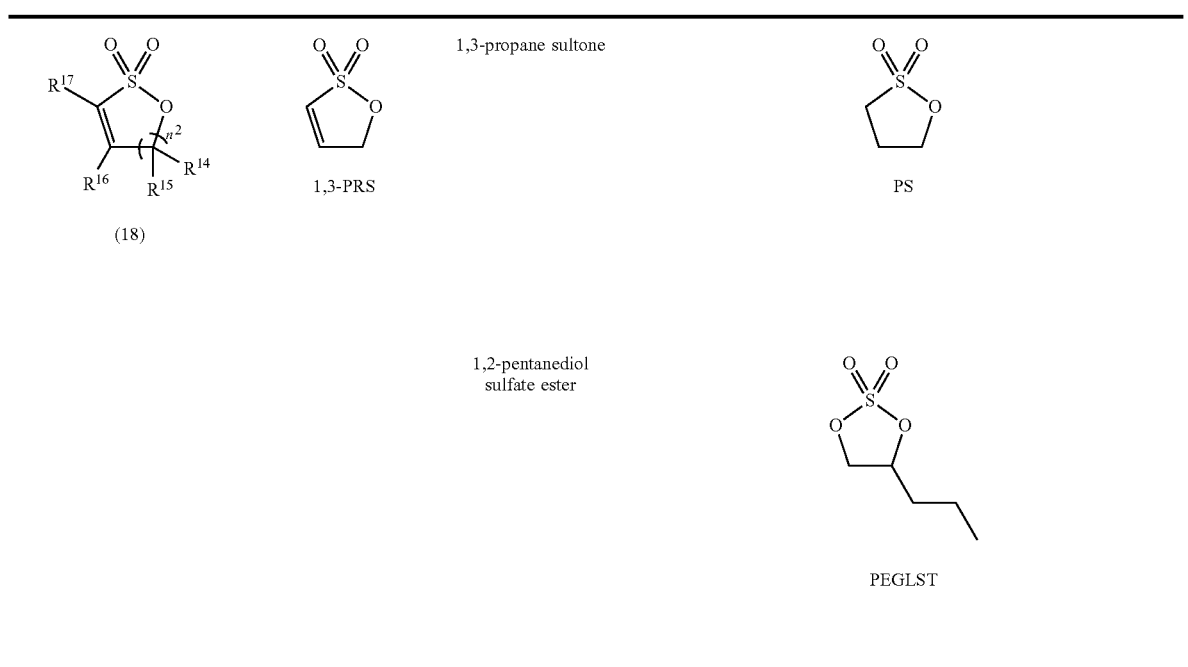

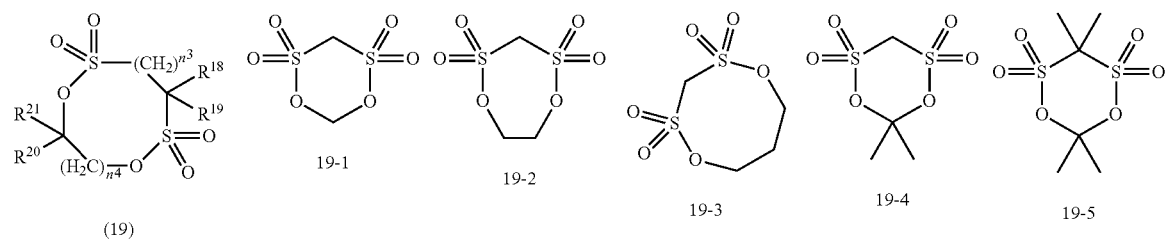

TABLE 47-continued

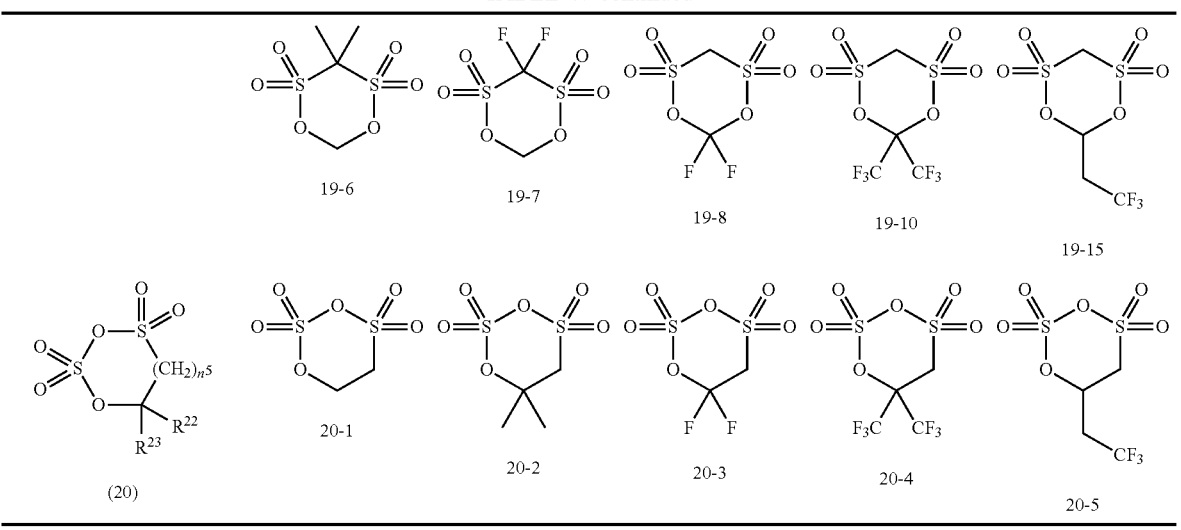

[2] Electrolytes Nos. C(19) to C(24)
[Preparation of Electrolytes Nos. C(19) to C(24)]

To a nonaqueous organic solvent including DEC and PC in a volume ratio of DEC:PC=2:1, $NaPF_6$ as a solute was added so that the concentration was 1 mol/L, 1Bd-Na synthesized in Example 3 as an ionic complex was added so that the concentration was 1 mass %, and a compound shown in Table 48 as a fourth compound was added so that the concentration was as descried in Table 48. The solute, the ionic complex, and the fourth compound were mixed sequentially in this order, and the mixture was stirred for one hour to obtain an electrolyte for a nonaqueous electrolyte battery.

[Evaluation]

An aluminum laminate outer package cell (capacity: 300 mAh) was fabricated by the same procedure as in Example 901 except that the electrolytes Nos. C(19) to C(24) were used as the electrolyte, and similarly, the degree of deterioration of a cell was evaluated based on the amount of gas generated after 10 cycles and the discharge capacity maintenance rate after 200 cycles (evaluation of the amount of gas generated and the cycle characteristics). Note here that in charging, the voltage reached 3.8 V and then was maintained at 3.8 V for one hour. Discharge was carried out to 1.5 V. Thus, the charge/discharge cycle was repeated. Values are shown in Table 48, as relative values when the amount of gas generated and the discharge capacity maintenance rate in Comparative Example 901 are defined 100, respectively.

Furthermore, similar to the evaluation of the amount of gas generated, the output characteristics at low temperature were evaluated using cells after 10 cycles. That is to say, after 10 cycles, the cells were cooled to 25° C. and discharged to 3.0 V, and then charged at −20° C. at 0.2 C rate to 3.8 V, and 3.8 V was maintained for one hour. Furthermore, discharging was carried out at −20° C. at 5 C rate to 1.5 V, and discharge capacity at −20° C. was measured. Note here that numerical values of discharge capacity (−20° C.) described in Table 48 are relative values when the discharge capacity (−20° C.) of Comparative Example 901 is defined as 100.

From the results shown in Table 48, it is found that even in the case of a sodium ion battery, Examples C1-(19) to C1-(24) using the electrolytes Nos. C(19) to C(24) further including the fourth compound in addition to the ionic complex can further improve at least one of the reduction of the amount of gas generated, the cycle characteristics, and the output characteristics at low temperature, as compared with Example 901.

TABLE 48

| Electrolyte No. | | Evaluation | | Positive electrode | Negative electrode | Ionic complex | | Fourth compound Type | mass % | Amount of gas generated after 10 cycles at 60° C. | Discharge capacity maintenance rate after 200 cycles at 60° C. | −20° C. discharge capacity after 10 cycles at 60° C. |
|---|---|---|---|---|---|---|---|---|---|---|---|---|
| | C(19) | | C1-(19) | $NaFe_{0.5}Co_{0.5}O_2$ | Hard carbon | 1Bd-Na | 1 mass % | PS | 2 | 70 | 142 | 129 |
| | C(20) | | C1-(20) | | | | | 1,3-PRS | 1 | 65 | 145 | 125 |
| | C(21) | | C1-(21) | | | | | PEGLST | 1 | 70 | 143 | 132 |
| | C(22) | | C1-(22) | | | | | 19-1 | 1 | 60 | 147 | 135 |
| | C(23) | | C1-(23) | | | | | 19-15 | 1 | 60 | 149 | 135 |
| | C(24) | | C1-(24) | | | | | 20-1 | 1 | 60 | 149 | 136 |
| Example | 64 | Example | 901 | | | | | — | — | 70 | 140 | 125 |
| Comparative Example | 17 | Comparative Example | 901 | | | — | — | — | — | 100 | 100 | 100 |

[3] Electrolytes Nos. C(25) to C(42)
[Preparation of Electrolytes Nos. C(25) to C(42)]

To a nonaqueous organic solvent including EMC and EC in a volume ratio of EMC:EC=2:1, $LiPF_6$ as a solute was added so that the concentration was 1 mol/L, 3Pa synthesized in Example 4 as an ionic complex was added so that the concentration was 1 mass %, and a compound shown in Table 49 as a fourth compound was added so that the concentration was as descried in Table 49. The solute, the ionic complex, and the fourth compound were mixed sequentially in this order, and the mixture was stirred for one hour to obtain electrolytes for a nonaqueous electrolyte battery.

[Evaluation]

An aluminum laminate outer package cell (capacity: 300 mAh) was fabricated by the same procedure as in Example 210 except that the electrolytes Nos. C(25) to C(42) were used as the electrolyte, and similarly, the degree of deterioration of a cell was evaluated based on the amount of gas generated after 10 cycles and the discharge capacity maintenance rate after 500 cycles (evaluation of the amount of gas generated and the cycle characteristics). Values are shown in Table 49, as the relative values when the amount of gas generated and the discharge capacity maintenance rate in Comparative Example 201 are defined 100, respectively.

Furthermore, similar to the evaluation of the amount of gas generated, the output characteristics at low temperature were evaluated using cells after 10 cycles. That is to say, after 10 cycles, the cells were cooled to 25° C. and discharged to 3.0 V, and then charged at −20° C. at 0.2 C rate to 4.3 V, and 4.3 V was maintained for one hour. Furthermore, discharging was carried out at −20° C., at 5 C rate to 3.0 V, and discharge capacity at −20° C. was measured. Note here that numerical values of discharge capacity (−20° C.) described in Table 49 are relative values when the discharge capacity (−20° C.) of Comparative Example 201 is defined as 100.

From the results shown in Table 49, even when the types of the ionic complex are changed, it is found that Examples C1-(25) to C1-(42) using electrolytes Nos. C(25) to C(42) further including the fourth compound in addition to the ionic complex can further improve at least one of the reduction of the amount of gas generated, the cycle characteristics, and the output characteristics at low temperature as compared with Example 210.

TABLE 49

| Electrolyte No. | | Evaluation | Positive electrode | Negative electrode | Ionic complex | | Fourth compound | | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|---|---|
| | | | | | | | Type | mass % | | | |
| C(25) | Example | C1-(25) | NCM | Graphite | (structure) | | PS | 0.5 | 70 | 127 | 125 |
| C(26) | | C1-(26) | | | | | " | 1 | 70 | 131 | 128 |
| C(27) | | C1-(27) | | | | | " | 2 | 70 | 133 | 130 |
| C(28) | | C1-(28) | | | | | 1,3-PRS | 0.2 | 70 | 126 | 125 |
| C(29) | | C1-(29) | | | | | " | 0.5 | 65 | 130 | 125 |
| C(30) | | C1-(30) | | | | | " | 1 | 65 | 135 | 125 |
| C(31) | | C1-(31) | | | | | PEGLST | 0.2 | 70 | 126 | 126 |
| C(32) | | C1-(32) | | | | | " | 0.5 | 70 | 129 | 129 |
| C(33) | | C1-(33) | | | 3Pa | 1 mass % | " | 1 | 70 | 134 | 132 |
| C(34) | | C1-(34) | | | | | 19-1 | 0.2 | 70 | 126 | 128 |
| C(35) | | C1-(35) | | | | | " | 0.5 | 65 | 133 | 133 |
| C(36) | | C1-(36) | | | | | " | 1 | 60 | 138 | 136 |
| C(37) | | C1-(37) | | | | | 19-15 | 0.2 | 70 | 126 | 127 |
| C(38) | | C1-(38) | | | | | " | 0.5 | 65 | 134 | 132 |
| C(39) | | C1-(39) | | | | | " | 1 | 60 | 140 | 135 |
| C(40) | | C1-(40) | | | | | 20-1 | 0.2 | 70 | 126 | 128 |
| C(41) | | C1-(41) | | | | | " | 0.5 | 65 | 134 | 134 |
| C(42) | | C1-(42) | | | | | " | 1 | 60 | 139 | 137 |
| Example 20 | Example | 210 | | | — | — | — | — | 70 | 130 | 120 |
| Comparative Example 11 | Comparative Example | 201 | | | — | — | — | — | 100 | 100 | 100 |

[4] Electrolytes Nos. C(43) to C(48)
[Preparation of Electrolytes Nos. C(43) to C(48)]

To a nonaqueous organic solvent including DEC and PC in a volume ratio of DEC:PC=2:1, $NaPF_6$ as a solute was added so that the concentration was 1 mol/L, 1Bd-Na synthesized in Example 3 as an ionic complex was added so that the concentration was 1 mass %, and a compound shown in Table 50 as a fourth compound was added so that the concentration was as descried in Table 50. The solute, the ionic complex, and the fourth compound were mixed sequentially in this order, and the mixture was stirred for one hour to obtain electrolytes for a nonaqueous electrolyte battery.

[Evaluation]

An aluminum laminate outer package cell (capacity: 300 mAh) was fabricated by the same procedure as in Example 902 except that the electrolytes Nos. C(43) to C(48) were used as the electrolyte, and similarly, the degree of deterioration of a cell was evaluated based on the amount of gas generated after 10 cycles and the discharge capacity maintenance rate after 200 cycles (evaluation of the amount of gas generated and the cycle characteristics). Note here that in charging, the voltage reached 3.8 V and then was maintained at 3.8 V for one hour. Discharge was carried out to 1.5 V. Thus, the charge/discharge cycle was repeated. Values are shown in Table 50, as relative values when the amount of gas generated and the discharge capacity maintenance rate in Comparative Example 901 are defined 100, respectively.

Furthermore, similar to the evaluation of the amount of gas generated, the output characteristics at low temperature were evaluated using cells after 10 cycles. That is to say, after 10 cycles, the cells were cooled to 25° C. and discharged to 3.0 V, and then charged at −20° C. at 0.2 C rate to 3.8 V, and 3.8 V was maintained for one hour. Furthermore, discharging was carried out at −20° C. at 5 C rate to 1.5 V, and discharge capacity at −20° C. was measured. Note here that numerical values of discharge capacity (−20° C.) described in Table 50 are relative values when the discharge capacity (−20° C.) of Comparative Example 901 is defined as 100.

From the results shown in Table 50, it is found that even in the case of a sodium ion battery, Examples C1-(43) to C1-(48) using the electrolytes Nos. C(43) to C(48) further including the fourth compound in addition to the ionic complex can further improve at least one of the reduction of the amount of gas generated, the cycle characteristics, and the output characteristics at low temperature, as compared with Example 902.

Examples using the electrolytes Nos. C(3), C(6), C(9), C(12), C(15), and C(18) are respectively shown as relative values when the amount of gas generated, the discharge capacity maintenance rate, and the discharge capacity (−20° C.) in comparative Examples using the electrolyte of Comparative Example 11 in the corresponding battery configuration are defined 100.

From the above-mentioned results, even when the types of the positive electrode and the negative electrode are changed, it is found that Examples using electrolytes Nos. C(3), C(6), C(9), C(12), C(15), and C(18), which further include the fourth compound in addition to the ionic complex, can further improve at least one of the reduction of the amount of gas generated, the cycle characteristics, and the output characteristics at a low temperature as compared with Example using the electrolyte of Example 16.

In Table 52, in each battery configuration, the values of the amount of gas generated, the discharge capacity main-

TABLE 50

| Electrolyte No. | Evaluation | Positive electrode | Negative electrode | Ionic complex | Fourth compound Type | mass % | Amount of gas generated after 10 cycles at 60° C. | Discharge capacity maintenance rate after 200 cycles at 60° C. | −20° C. discharge capacity after 10 cycles at 60° C. |
|---|---|---|---|---|---|---|---|---|---|
| C(43) | C1-(43) | NaFe$_{0.5}$Co$_{0.5}$O$_2$ | Hard carbon | 3Pa 1 mass % | PS | 2 | 70 | 150 | 122 |
| C(44) | C1-(44) | | | | 1,3-PRS | 1 | 75 | 152 | 120 |
| C(45) | C1-(45) | | | | PEGLST | 1 | 75 | 151 | 125 |
| C(46) | C1-(46) | | | | 19-1 | 1 | 65 | 155 | 125 |
| C(47) | C1-(47) | | | | 19-15 | 1 | 65 | 157 | 125 |
| C(48) | C1-(48) | | | | 20-1 | 1 | 70 | 157 | 127 |
| Example 68 | Example 902 | | | — | — | — | 75 | 150 | 120 |
| Comparative Example 17 | Comparative Example 901 | | | — | — | — | 100 | 100 | 100 |

[5] Various Combinations of Specific Ionic Complex and Fourth Compound

Hereinafter, electrolytes having typical combinations of a specific ionic complex and a fourth compound and concentration were evaluated while the types of positive electrodes, negative electrodes, and the like, are varied. The combinations of positive and negative electrodes and evaluation conditions are as shown in Table 36.

The above-mentioned evaluation results are shown in Tables 51 and 52. Note here that it is demonstrated that electrolytes other than the electrolytes having the combination of an ionic complex and a fourth compound and the concentration mentioned below show the same tendency as mentioned above.

In Table 51, in each battery configuration, the values of the amount of gas generated, the discharge capacity maintenance rate, and the discharge capacity (−20° C.) of Examples using the electrolytes Nos. C(27), C(30), C(33), C(36), C(39), and C(42) are respectively shown as relative values when the amount of gas generated, the discharge capacity maintenance rate, and the discharge capacity (−20° C.) in Comparative Examples using the electrolyte of Comparative Example 11 in the corresponding battery configuration are defined 100.

From the above-mentioned results, even when the types of the positive electrode and the negative electrode are changed, it is found that Examples using electrolytes Nos. C(27), C(30), C(33), C(36), C(39), and C(42), further including the fourth compound in addition to the ionic complex can further improve at least one of the reduction of the amount of gas generated, the cycle characteristics, and the output characteristics at low temperature as compared with Example using the electrolyte of Example 20.

TABLE 51

| Electrolyte No. | Evaluation | Positive electrode | Negative electrode | Ionic complex | Fourth compound 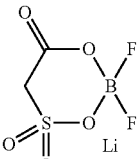 1Bd-Li 1 mass % Type | mass % | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|
| C(3) | Example C2-(3) | NCM | Hard carbon | 1Bd-Li 1 mass % | PS | 2 | 65 | 134 | 132 |
| C(6) | C2-(6) | | | | 1,3-PRS | 1 | 60 | 137 | 127 |
| C(9) | C2-(9) | | | | PEGLST | 1 | 65 | 136 | 135 |
| C(12) | C2-(12) | | | | 19-1 | 1 | 55 | 140 | 137 |
| C(15) | C2-(15) | | | | 19-15 | 1 | 55 | 141 | 137 |
| C(18) | C2-(18) | | | | 20-1 | 1 | 60 | 140 | 136 |
| Example 16 | Example A2-16 | | | | — | — | 65 | 128 | 126 |
| Comparative Example 11 | Comparative Example A2-11 | | | — | — | — | 100 | 100 | 100 |
| C(3) | Example C3-(3) | NCM | Silicon | 1Bd-Li 1 mass % | PS | 2 | 70 | 355 | 273 |
| C(6) | C3-(6) | | | | 1,3-PRS | 1 | 65 | 353 | 275 |
| C(9) | C3-(9) | | | | PEGLST | 1 | 70 | 355 | 270 |
| C(12) | C3-(12) | | | | 19-1 | 1 | 60 | 365 | 283 |
| C(15) | C3-(15) | | | | 19-15 | 1 | 60 | 360 | 282 |
| C(18) | C3-(18) | | | | 20-1 | 1 | 60 | 363 | 285 |
| Example 16 | Example A3-16 | | | | — | — | 70 | 350 | 260 |
| Comparative Example 11 | Comparative Example A3-11 | | | — | — | — | 100 | 100 | 100 |
| C(3) | Example C4-(3) | NCM | LTO | 1Bd-Li 1 mass % | PS | 2 | 80 | 118 | 107 |
| C(6) | C4-(6) | | | | 1,3-PRS | 1 | 80 | 120 | 107 |
| C(9) | C4-(9) | | | | PEGLST | 1 | 80 | 121 | 106 |
| C(12) | C4-(12) | | | | 19-1 | 1 | 75 | 128 | 110 |
| C(15) | C4-(15) | | | | 19-15 | 1 | 75 | 130 | 110 |
| C(18) | C4-(18) | | | | 20-1 | 1 | 75 | 132 | 110 |
| Example 16 | Example A4-16 | | | | — | — | 80 | 110 | 105 |
| Comparative Example 11 | Comparative Example A4-11 | | | — | — | — | 100 | 100 | 100 |
| C(3) | Example C5-(3) | LFP | Graphite | 1Bd-Li 1 mass % | PS | 2 | 70 | 130 | 124 |
| C(6) | C5-(6) | | | | 1,3-PRS | 1 | 70 | 128 | 123 |
| C(9) | C5-(9) | | | | PEGLST | 1 | 70 | 131 | 122 |
| C(12) | C5-(12) | | | | 19-1 | 1 | 65 | 136 | 128 |
| C(15) | C5-(15) | | | | 19-15 | 1 | 65 | 135 | 129 |
| C(18) | C5-(18) | | | | 20-1 | 1 | 65 | 134 | 129 |
| Example 16 | Example A5-16 | | | | — | — | 70 | 122 | 120 |
| Comparative Example 11 | Comparative Example A5-11 | | | — | — | — | 100 | 100 | 100 |
| C(3) | Example C6-(3) | NCA | Graphite | 1Bd-Li 1 mass % | PS | 2 | 60 | 125 | 133 |
| C(6) | C6-(6) | | | | 1,3-PRS | 1 | 65 | 128 | 128 |
| C(9) | C6-(9) | | | | PEGLST | 1 | 65 | 129 | 132 |
| C(12) | C6-(12) | | | | 19-1 | 1 | 55 | 133 | 137 |
| C(15) | C6-(15) | | | | 19-15 | 1 | 55 | 132 | 138 |
| C(18) | C6-(18) | | | | 20-1 | 1 | 55 | 135 | 138 |
| Example 16 | Example A6-16 | | | | — | — | 65 | 120 | 125 |
| Comparative Example 11 | Comparative Example A6-11 | | | — | — | — | 100 | 100 | 100 |
| C(3) | Example C7-(3) | LMO | Graphite | 1Bd-Li 1 mass % | PS | 2 | 60 | 118 | 117 |
| C(6) | C7-(6) | | | | 1,3-PRS | 1 | 60 | 120 | 116 |
| C(9) | C7-(9) | | | | PEGLST | 1 | 60 | 121 | 115 |
| C(12) | C7-(12) | | | | 19-1 | 1 | 55 | 128 | 120 |
| C(15) | C7-(15) | | | | 19-15 | 1 | 55 | 125 | 121 |
| C(18) | C7-(18) | | | | 20-1 | 1 | 55 | 127 | 121 |
| Example 16 | Example A7-16 | | | | — | — | 60 | 115 | 112 |
| Comparative Example 11 | Comparative Example A7-11 | | | — | — | — | 100 | 100 | 100 |
| C(3) | Example C8-(3) | LCO | Graphite | 1Bd-Li 1 mass % | PS | 2 | 70 | 124 | 118 |
| C(6) | C8-(6) | | | | 1,3-PRS | 1 | 75 | 128 | 116 |
| C(9) | C8-(9) | | | | PEGLST | 1 | 75 | 130 | 116 |
| C(12) | C8-(12) | | | | 19-1 | 1 | 65 | 132 | 121 |
| C(15) | C8-(15) | | | | 19-15 | 1 | 65 | 135 | 121 |
| C(18) | C8-(18) | | | | 20-1 | 1 | 70 | 136 | 122 |
| Example 16 | Example A8-16 | | | | — | — | 75 | 120 | 115 |
| Comparative Example 11 | Comparative Example A8-11 | | | — | — | — | 100 | 100 | 100 |

TABLE 52

| Electrolyte No. | | Evaluation | Positive electrode | Negative electrode | Ionic complex | | Fourth compound  | | Amount of gas generated after 10 cycles at 60° C. | Discharge capacity maintenance rate after 500 cycles at 60° C. | −20° C. discharge capacity after 10 cycles at 60° C. |
|---|---|---|---|---|---|---|---|---|---|---|---|
| | | | | | | | Type | mass % | | | |
| | | C(27) | C2-(27) | NCM | Hard carbon | 3Pa | 1 mass % | PS | 2 | 70 | 139 | 130 |
| | | C(30) | C2-(30) | | | | | 1,3-PRS | 1 | 65 | 142 | 126 |
| | | C(33) | C2-(33) | | | | | PEGLST | 1 | 65 | 141 | 131 |
| | | C(36) | C2-(36) | | | | | 19-1 | 1 | 60 | 144 | 132 |
| | | C(39) | C2-(39) | | | | | 19-15 | 1 | 60 | 144 | 132 |
| | | C(42) | C2-(42) | | | | | 20-1 | 1 | 65 | 144 | 134 |
| Example | 20 | Example | A2-20 | | | | | — | — | 75 | 132 | 121 |
| Comparative Example | 11 | Comparative Example | A2-11 | | | — | — | — | — | 100 | 100 | 100 |
| | | C(27) | C3-(27) | NCM | Silicon | 3Pa | 1 mass % | PS | 2 | 75 | 390 | 260 |
| | | C(30) | C3-(30) | | | | | 1,3-PRS | 1 | 70 | 385 | 260 |
| | | C(33) | C3-(33) | | | | | PEGLST | 1 | 75 | 390 | 255 |
| | | C(36) | C3-(36) | | | | | 19-1 | 1 | 65 | 392 | 265 |
| | | C(39) | C3-(39) | | | | | 19-15 | 1 | 65 | 395 | 265 |
| | | C(42) | C3-(42) | | | | | 20-1 | 1 | 65 | 395 | 268 |
| Example | 20 | Example | A3-20 | | | | | — | — | 80 | 380 | 240 |
| Comparative Example | 11 | Comparative Example | A3-11 | | | — | — | — | — | 100 | 100 | 100 |
| | | C(27) | C4-(27) | NCM | LTO | 3Pa | 1 mass % | PS | 2 | 85 | 121 | 105 |
| | | C(30) | C4-(30) | | | | | 1,3-PRS | 1 | 80 | 123 | 105 |
| | | C(33) | C4-(33) | | | | | PEGLST | 1 | 85 | 123 | 104 |
| | | C(36) | C4-(36) | | | | | 19-1 | 1 | 80 | 130 | 107 |
| | | C(39) | C4-(39) | | | | | 19-15 | 1 | 80 | 132 | 107 |
| | | C(42) | C4-(42) | | | | | 20-1 | 1 | 80 | 133 | 107 |
| Example | 20 | Example | A4-20 | | | | | — | — | 90 | 113 | 103 |
| Comparative Example | 11 | Comparative Example | A4-11 | | | — | — | — | — | 100 | 100 | 100 |
| | | C(27) | C5-(27) | LFP | Graphite | 3Pa | 1 mass % | PS | 2 | 75 | 130 | 122 |
| | | C(30) | C5-(30) | | | | | 1,3-PRS | 1 | 75 | 129 | 120 |
| | | C(33) | C5-(33) | | | | | PEGLST | 1 | 75 | 132 | 119 |
| | | C(36) | C5-(36) | | | | | 19-1 | 1 | 70 | 136 | 125 |
| | | C(39) | C5-(39) | | | | | 19-15 | 1 | 70 | 137 | 125 |
| | | C(42) | C5-(42) | | | | | 20-1 | 1 | 70 | 137 | 126 |
| Example | 20 | Example | A5-20 | | | | | — | — | 80 | 123 | 115 |
| Comparative Example | 11 | Comparative Example | A5-11 | | | — | — | — | — | 100 | 100 | 100 |
| | | C(27) | C6-(27) | NCA | Graphite | 3Pa | 1 mass % | PS | 2 | 65 | 130 | 131 |
| | | C(30) | C6-(30) | | | | | 1,3-PRS | 1 | 70 | 131 | 125 |
| | | C(33) | C6-(33) | | | | | PEGLST | 1 | 70 | 133 | 124 |
| | | C(36) | C6-(36) | | | | | 19-1 | 1 | 65 | 138 | 132 |
| | | C(39) | C6-(39) | | | | | 19-15 | 1 | 60 | 138 | 133 |
| | | C(42) | C6-(42) | | | | | 20-1 | 1 | 60 | 137 | 134 |
| Example | 20 | Example | A6-20 | | | | | — | — | 75 | 125 | 120 |
| Comparative Example | 11 | Comparative Example | A6-11 | | | — | — | — | — | 100 | 100 | 100 |
| | | C(27) | C7-(27) | LMO | Graphite | 3Pa | 1 mass % | PS | 2 | 65 | 120 | 114 |
| | | C(30) | C7-(30) | | | | | 1,3-PRS | 1 | 65 | 121 | 114 |
| | | C(33) | C7-(33) | | | | | PEGLST | 1 | 60 | 122 | 112 |
| | | C(36) | C7-(36) | | | | | 19-1 | 1 | 65 | 130 | 116 |
| | | C(39) | C7-(39) | | | | | 19-15 | 1 | 60 | 128 | 117 |
| | | C(42) | C7-(42) | | | | | 20-1 | 1 | 60 | 129 | 118 |
| Example | 20 | Example | A7-20 | | | | | — | — | 70 | 117 | 109 |
| Comparative Example | 11 | Comparative Example | A7-11 | | | — | — | — | — | 100 | 100 | 100 |
| | | C(27) | C8-(27) | LCO | Graphite | 3Pa | 1 mass % | PS | 2 | 80 | 128 | 115 |
| | | C(30) | C8-(30) | | | | | 1,3-PRS | 1 | 80 | 130 | 114 |
| | | C(33) | C8-(33) | | | | | PEGLST | 1 | 85 | 132 | 113 |
| | | C(36) | C8-(36) | | | | | 19-1 | 1 | 80 | 135 | 118 |
| | | C(39) | C8-(39) | | | | | 19-15 | 1 | 75 | 137 | 119 |
| | | C(42) | C8-(42) | | | | | 20-1 | 1 | 75 | 137 | 119 |
| Example | 20 | Example | A8-20 | | | | | — | — | 85 | 125 | 112 |
| Comparative Example | 11 | Comparative Example | A8-11 | | | — | — | — | — | 100 | 100 | 100 |

Fifth Embodiment

Electrolyte for Nonaqueous Electrolyte Battery Further Containing Fifth Compound (Cyclic Carbonate Compound) in Addition to Specific Ionic Complex
[1] Electrolytes Nos. D(1) to D(12)
[Preparation of Electrolytes Nos. D(1) to D(12)]

To a nonaqueous organic solvent including EMC and EC in a volume ratio of EMC:EC=2:1, $LiPF_6$ as a solute was added so that the concentration was 1 mol/L, 1Bd-Li synthesized in Example 2 as an ionic complex was added so that the concentration was 1 mass %, and a compound shown in Table 53 as a fifth compound was added so that the concentration was as descried in Table 53. The solute, the ionic complex, and the fifth compound were mixed sequentially in this order, and the mixture was stirred for one hour to obtain electrolytes for a nonaqueous electrolyte battery. In Table 53, the fifth compounds are compounds shown in Table 54. Note here that also all preparation of electrolytes hereinafter was carried out while the liquid temperature was maintained at 40° C. or less.

[Evaluation]

An aluminum laminate outer package cell (capacity: 300 mAh) was fabricated by the same procedure as in Example 206 except that the electrolytes Nos. D(1) to D(12) were used as the electrolyte, and similarly, the degree of deterioration of a cell was evaluated based on the amount of gas generated after 10 cycles and the discharge capacity maintenance rate after 500 cycles (evaluation of the amount of gas generated and the cycle characteristics). Values are shown in Table 53, as the relative values when the amount of gas generated and the discharge capacity maintenance rate in Comparative Example 201 are defined 100, respectively.

From the results shown in Table 53, it is found that Examples D1-(1) to D1-(12) using the electrolytes Nos. D(1) to D(12) further including the fifth compound in addition to the ionic complex show the amount of gas generated equal to that in Example 206 and further improved cycle characteristics.

TABLE 53

| Electrolyte No. | | Evaluation | | Positive electrode | Negative electrode | Ionic complex | | Fifth compound Type | mass % | Amount of gas generated after 10 cycles at 60° C. | Discharge capacity maintenance rate after 500 cycles at 60° C. |
|---|---|---|---|---|---|---|---|---|---|---|---|
| | D(1) | Example | D1-(1) | NCM | Graphite | | | 21-1 | 0.5 | 65 | 135 |
| | D(2) | | D1-(2) | | | | | " | 1 | 60 | 140 |
| | D(3) | | D1-(3) | | | | | " | 3 | 60 | 150 |
| | D(4) | | D1-(4) | | | | | 21-2 | 0.5 | 70 | 133 |
| | D(5) | | D1-(5) | | | | | " | 1 | 65 | 138 |
| | D(6) | | D1-(6) | | | | | " | 3 | 65 | 146 |
| | D(7) | | D1-(7) | | | | | 21-3 | 0.5 | 70 | 129 |
| | D(8) | | D1-(8) | | | | | " | 1 | 75 | 134 |
| | D(9) | | D1-(9) | | | 1Bd-Li | 1 mass % | " | 3 | 75 | 138 |
| | D(10) | | D1-(10) | | | | | 21-4 | 0.5 | 70 | 128 |
| | D(11) | | D1-(11) | | | | | " | 1 | 75 | 134 |
| | D(12) | | D1-(12) | | | | | " | 3 | 75 | 138 |
| Example | 16 | Example | 206 | | | | | — | — | 70 | 125 |
| Comparative Example | 11 | Comparative Example | 201 | | | — | — | — | — | 100 | 100 |

TABLE 54

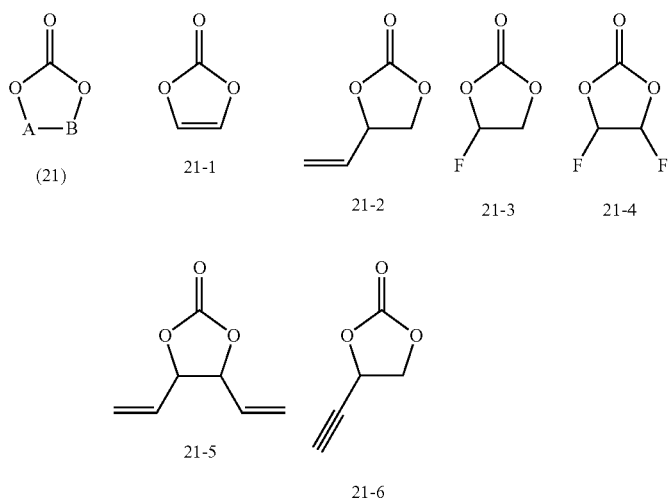

In Table 54,
O is oxygen atom,
A is hydrocarbon having 10 or less carbon atoms and optionally including an unsaturated bond or a ring structure or a halogen atom, and
B is hydrocarbon having 10 or less carbon atoms and optionally including an unsaturated bond or a ring structure or a halogen atom.
Furthermore, a double bond may be formed between A and B.

[2] Electrolytes Nos. D(13) to D(16)
[Preparation of Electrolytes Nos. D(13) to D(16)]

To a nonaqueous organic solvent including DEC and PC in a volume ratio of DEC:PC=2:1, $NaPF_6$ as a solute was added so that the concentration was 1 mol/L, 1Bd-Na synthesized in Example 3 as an ionic complex was added so that the concentration was 1 mass %, and a compound shown in Table 55 as a fifth compound was added so that the concentration was the concentration descried in Table 55. The solute, the ionic complex, and the fifth compound were mixed sequentially in this order, and the mixture was stirred for one hour to obtain electrolytes for a nonaqueous electrolyte battery.

[Evaluation]

An aluminum laminate outer package cell (capacity: 300 mAh) was fabricated by the same procedure as in Example 901 except that the electrolytes Nos. D(13) to D(16) were used as the electrolyte, and similarly, the degree of deterioration of a cell was evaluated based on the amount of gas generated after 10 cycles and the discharge capacity maintenance rate after 200 cycles (evaluation of the amount of gas generated and the cycle characteristics). Note here that in charging, the voltage reached 3.8 V and then was maintained at 3.8 V for one hour. Discharge was carried out to 1.5 V. Thus, the charge/discharge cycle was repeated. Values are shown in Table 55, as relative values when the amount of gas generated and the discharge capacity maintenance rate in Comparative Example 901 are defined 100, respectively.

From the results shown in Table 55, it is found that even in the case of a sodium ion battery, Examples D1-(13) to D1-(16) using the electrolytes Nos. D(13) to D(16) further including the fifth compound in addition to the ionic complex show the amount of gas generated that is equal to or not more than that in Example 901 and the improved cycle characteristics.

[3] Electrolytes Nos. D(17) to D(28)

[Preparation of Electrolytes Nos. D(17) to D(28)]

To a nonaqueous organic solvent including EMC and EC in a volume ratio of EMC:EC=2:1, $LiPF_6$ as a solute was added so that the concentration was 1 mol/L, 3Pa synthesized in Example 4 as an ionic complex was added so that the concentration was 1 mass %, and a compound shown in Table 56 as a fifth compound was added so that the concentration was as descried in Table 56. The solute, the ionic complex, and the fifth compound were mixed sequentially in this order, and the mixture was stirred for one hour to obtain electrolytes for a nonaqueous electrolyte battery.

[Evaluation]

An aluminum laminate outer package cell (capacity: 300 mAh) was fabricated by the same procedure as in Example 210 except that the electrolytes Nos. D(17) to D(28) were used as the electrolyte, and similarly, the degree of deterioration of a cell was evaluated based on the amount of gas generated after 10 cycles and the discharge capacity maintenance rate after 500 cycles (evaluation of the amount of gas generated and the cycle characteristics). Values are shown in Table 56, as the relative values when the amount of gas generated and the discharge capacity maintenance rate in Comparative Example 201 are defined 100, respectively.

From the results shown in Table 56, it is found that even when the types of the ionic complex is changed, Examples D1-(17) to D1-(28) using the electrolytes Nos. D(17) to D(28) further including the fifth compound in addition to the ionic complex show the amount of gas generated equal to that in Example 210 and further improve the cycle characteristics.

TABLE 55

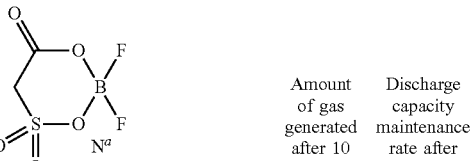

| Electrolyte No. | | Evaluation | | Positive electrode | Negative electrode | Ionic complex | Fifth compound Type | mass % | Amount of gas generated after 10 cycles at 60° C. | Discharge capacity maintenance rate after 200 cycles at 60° C. |
|---|---|---|---|---|---|---|---|---|---|---|
| | D(13) | | D1-(13) | $NaFe_{0.5}Co_{0.5}O_2$ | Hard carbon | 1Bd-Na 1 mass % | 21-1 | 3 | 60 | 148 |
| | D(14) | | D1-(14) | | | | 21-2 | 3 | 65 | 146 |
| | D(15) | | D1-(15) | | | | 21-3 | 3 | 50 | 155 |
| | D(16) | | D1-(16) | | | | 21-4 | 3 | 50 | 153 |
| Example | 64 | Example | 901 | | | | — | — | 70 | 140 |
| Comparative Example | 17 | Comparative Example | 901 | | | — | — | — | 100 | 100 |

TABLE 56

| Electrolyte No. | | Evaluation | | Positive electrode | Negative electrode | Ionic complex | | Fifth compound Type | mass % | Amount of gas generated after 10 cycles at 60° C. | Discharge capacity maintenance rate after 500 cycles at 60° C. |
|---|---|---|---|---|---|---|---|---|---|---|---|
| | D(17) | Example | D1-(17) | NCM | Graphite | (structure) | | 21-1 | 0.5 | 75 | 138 |
| | D(18) | | D1-(18) | | | | | " | 1 | 70 | 141 |
| | D(19) | | D1-(19) | | | | | " | 3 | 70 | 155 |
| | D(20) | | D1-(20) | | | | | 21-2 | 0.5 | 80 | 136 |
| | D(21) | | D1-(21) | | | | | " | 1 | 75 | 140 |
| | D(22) | | D1-(22) | | | | | " | 3 | 75 | 152 |
| | D(23) | | D1-(23) | | | | | 21-3 | 0.5 | 80 | 131 |
| | D(24) | | D1-(24) | | | | | " | 1 | 85 | 134 |
| | D(25) | | D1-(25) | | | 2Pa | 1 mass % | " | 3 | 85 | 140 |
| | D(26) | | D1-(26) | | | | | 21-4 | 0.5 | 80 | 132 |
| | D(27) | | D1-(27) | | | | | " | 1 | 85 | 135 |
| | D(28) | | D1-(28) | | | | | " | 3 | 85 | 140 |
| Example | 20 | Example | 210 | | | | | — | — | 80 | 130 |
| Comparative Example | 11 | Comparative Example | 201 | | | — | | — | — | 100 | 100 |

[4] Electrolytes Nos. D(29) to D(32)
[Preparation of Electrolytes Nos. D(29) to D(32)]

To a nonaqueous organic solvent including DEC and PC in a volume ratio of DEC:PC=2:1, $NaPF_6$ as a solute was added so that the concentration was 1 mol/L, 1Bd-Na synthesized in Example 3 as an ionic complex was added so that the concentration was 1 mass %, and a compound shown in Table 57 as a fifth compound was added so that the concentration was as descried in Table 57. The solute, the ionic complex, and the fifth compound were mixed sequentially in this order, and the mixture was stirred for one hour to obtain electrolytes for a nonaqueous electrolyte battery.
[Evaluation]

An aluminum laminate outer package cell (capacity: 300 mAh) was fabricated by the same procedure as in Example 902 except that the electrolytes Nos. D(29) to D(32) were used as the electrolyte, and similarly, the degree of deterioration of a cell was evaluated based on the amount of gas generated after 10 cycles and the discharge capacity maintenance rate after 200 cycles (evaluation of the amount of gas generated and the cycle characteristics). Note here that in charging, the voltage reached 3.8 V and then was maintained at 3.8 V for one hour. Discharge was carried out to 1.5 V. Thus, the charge/discharge cycle was repeated. Values are shown in Table 57, as relative values when the amount of gas generated and the discharge capacity maintenance rate in Comparative Example 901 are defined 100, respectively.

From the results shown in Table 57, it is found that in the case of a sodium ion battery, Examples D1-(29) to D1-(32) using the electrolytes Nos. D(29) to D(32) further including the fifth compound in addition to the ionic complex show the amount of gas generated that is equal to or not more than that in Example 902 and further improved cycle characteristics.

TABLE 57

| Electrolyte No. | | Evaluation | | Positive electrode | Negative electrode | Ionic complex | | Fifth compound Type | mass % | Amount of gas generated after 10 cycles at 60° C. | Discharge capacity maintenance rate after 200 cycles at 60° C. |
|---|---|---|---|---|---|---|---|---|---|---|---|
| | D(29) | | D1-(29) | $NaFe_{0.5}Co_{0.5}O_2$ | Hard carbon | 3Pa | 1 mass % | 21-1 | 3 | 65 | 156 |
| | D(30) | | D1-(30) | | | | | 21-2 | 3 | 70 | 155 |
| | D(31) | | D1-(31) | | | | | 21-3 | 3 | 60 | 165 |
| | D(32) | | D1-(32) | | | | | 21-4 | 3 | 60 | 165 |
| Example | 68 | Example | 902 | | | — | | — | — | 75 | 150 |
| Comparative Example | 17 | Comparative Example | 901 | | | — | | — | — | 100 | 100 |

[5] Various Combinations of Specific Ionic Complex and Fifth Compound

Hereinafter, electrolytes having typical combinations of a specific ionic complex and a fifth compound and concentration were evaluated while the types of positive electrodes, negative electrodes, and the like, are varied. The combinations of positive and negative electrodes and evaluation conditions are as shown in Table 36.

The above-mentioned evaluation results are shown in Tables 58 and 59. Note here that it is demonstrated that electrolytes other than the electrolytes having the combination of an ionic complex and a fifth compound and the concentration mentioned below show the same tendency as mentioned above.

In Table 58, in each battery configuration, the values of the amount of gas generated, and the discharge capacity maintenance rate of Examples using the electrolytes Nos. D(3), D(6), D(9), and D(12) are respectively shown as relative values when the amount of gas generated and the discharge capacity maintenance rate in Comparative Examples using the electrolyte of Comparative Example 11 in the corresponding battery configuration are defined 100.

From the results mentioned above, even when the types of the positive electrode and the negative electrode are changed, it is found that Examples using electrolytes Nos. D(3), D(6), D(9), and D(12), which further include the fifth compound in addition to the ionic complex, show an amount of gas generated that is equal or not more than that of Example using the electrolyte of Example 16, and also show further improved cycle characteristics.

In Table 59, in each battery configuration, the values of the amount of gas generated, and the discharge capacity maintenance rate of Examples using the electrolytes Nos. C(19), C(22), C(25), and C(28) are respectively shown as relative values when the amount of gas generated, and the discharge capacity maintenance rate in Comparative Examples using the electrolyte of Comparative Example 11 in the corresponding battery configuration are defined 100.

From the results mentioned above, even when the types of the positive electrode and the negative electrode are changed, it is found that Examples using electrolytes Nos. C(19), C(22), C(25), and C(28), which further include the fifth compound in addition to the ionic complex, show an amount of gas generated that is equal or not more than that of Example using the electrolyte of Example 20, and also show further improved cycle characteristics.

TABLE 58

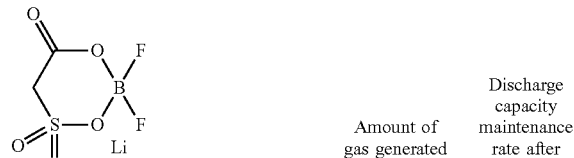

| Electrolyte No. | | Evaluation | | Positive electrode | Negative electrode | Ionic complex | | Fifth compound | | Amount of gas generated after 10 cycles at 60° C. | Discharge capacity maintenance rate after 500 cycles at 60° C. |
|---|---|---|---|---|---|---|---|---|---|---|---|
| | | | | | | | | Type | mass % | | |
| D(3) | | | D2-(3) | NCM | Hard carbon | 1Bd-Li | 1 mass % | 21-1 | 3 | 60 | 135 |
| D(6) | | | D2-(6) | | | | | 21-2 | 3 | 65 | 130 |
| D(9) | | | D2-(9) | | | | | 21-3 | 3 | 50 | 140 |
| D(12) | | | D2-(12) | | | | | 21-4 | 3 | 50 | 145 |
| Example | 16 | Example | A2-16 | | | | | — | — | 65 | 128 |
| Comparative Example | 11 | Comparative Example | A2-11 | | | — | — | — | — | 100 | 100 |
| D(3) | | | D3-(3) | NCM | Silicon | 1Bd-Li | 1 mass % | 21-1 | 3 | 65 | 365 |
| D(6) | | | D3-(6) | | | | | 21-2 | 3 | 70 | 355 |
| D(9) | | | D3-(9) | | | | | 21-3 | 3 | 60 | 376 |
| D(12) | | | D3-(12) | | | | | 21-4 | 3 | 60 | 382 |
| Example | 16 | Example | A3-16 | | | | | — | — | 70 | 350 |
| Comparative Example | 11 | Comparative Example | A3-11 | | | — | — | — | — | 100 | 100 |
| D(3) | | | D4-(3) | NCM | LTO | 1Bd-Li | 1 mass % | 21-1 | 3 | 75 | 120 |
| D(6) | | | D4-(6) | | | | | 21-2 | 3 | 75 | 116 |
| D(9) | | | D4-(9) | | | | | 21-3 | 3 | 80 | 113 |
| D(12) | | | D4-(12) | | | | | 21-4 | 3 | 80 | 112 |
| Example | 16 | Example | A4-16 | | | | | — | — | 80 | 110 |
| Comparative Example | 11 | Comparative Example | A4-11 | | | — | — | — | — | 100 | 100 |
| D(3) | | | D5-(3) | LFP | Graphite | 1Bd-Li | 1 mass % | 21-1 | 3 | 60 | 155 |
| D(6) | | | D5-(6) | | | | | 21-2 | 3 | 60 | 150 |
| D(9) | | | D5-(9) | | | | | 21-3 | 3 | 70 | 135 |
| D(12) | | | D5-(12) | | | | | 21-4 | 3 | 70 | 132 |
| Example | 16 | Example | A5-16 | | | | | — | — | 70 | 122 |
| Comparative Example | 11 | Comparative Example | A5-11 | | | — | — | — | — | 100 | 100 |
| D(3) | | | D6-(3) | NCA | Graphite | 1Bd-Li | 1 mass % | 21-1 | 3 | 55 | 135 |
| D(6) | | | D6-(6) | | | | | 21-2 | 3 | 55 | 131 |
| D(9) | | | D6-(9) | | | | | 21-3 | 3 | 65 | 125 |
| D(12) | | | D6-(12) | | | | | 21-4 | 3 | 65 | 125 |
| Example | 16 | Example | A6-16 | | | | | — | — | 65 | 120 |
| Comparative Example | 11 | Comparative Example | A6-11 | | | — | — | — | — | 100 | 100 |
| D(3) | | | D7-(3) | LMO | Graphite | 1Bd-Li | 1 mass % | 21-1 | 3 | 45 | 145 |
| D(6) | | | D7-(6) | | | | | 21-2 | 3 | 50 | 143 |
| D(9) | | | D7-(9) | | | | | 21-3 | 3 | 60 | 130 |
| D(12) | | | D7-(12) | | | | | 21-4 | 3 | 60 | 130 |
| Example | 16 | Example | A7-16 | | | | | — | — | 60 | 115 |
| Comparative Example | 11 | Comparative Example | A7-11 | | | — | — | — | — | 100 | 100 |
| D(3) | | | D8-(3) | LCO | Graphite | 1Bd-Li | 1 mass % | 21-1 | 3 | 60 | 150 |
| D(6) | | | D8-(6) | | | | | 21-2 | 3 | 65 | 146 |
| D(9) | | | D8-(9) | | | | | 21-3 | 3 | 75 | 128 |
| D(12) | | | D8-(12) | | | | | 21-4 | 3 | 75 | 130 |
| Example | 16 | Example | A8-16 | | | | | — | — | 75 | 120 |
| Comparative Example | 11 | Comparative Example | A8-11 | | | — | — | — | — | 100 | 100 |

TABLE 59

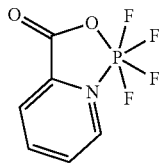

| Electrolyte No. | | Evaluation | | Positive electrode | Negative electrode | Ionic complex | Fifth compound Type | mass % | Amount of gas generated after 10 cycles at 60° C. | Discharge capacity maintenance rate after 500 cycles at 60° C. |
|---|---|---|---|---|---|---|---|---|---|---|
| | D(19) | | D2-(19) | NCM | Hard carbon | 3Pa | 21-1 | 3 | 65 | 138 |
| | D(22) | | D2-(22) | | | | 21-2 | 3 | 70 | 133 |
| | D(25) | | D2-(25) | | | | 21-3 | 3 | 60 | 145 |
| | D(26) | | D2-(26) | | | | 21-4 | 3 | 60 | 148 |
| Example | 20 | Example | A2-20 | | | | — | — | 75 | 132 |
| Comparative Example | 11 | Comparative Example | A2-11 | | | — | — | — | 100 | 100 |
| | D(19) | | D3-(19) | NCM | Silicon | 3Pa | 21-1 | 3 | 75 | 385 |
| | D(22) | | D3-(22) | | | | 21-2 | 3 | 80 | 381 |
| | D(25) | | D3-(25) | | | | 21-3 | 3 | 70 | 396 |
| | D(26) | | D3-(26) | | | | 21-4 | 3 | 70 | 399 |
| Example | 20 | Example | A3-20 | | | | — | — | 80 | 380 |
| Comparative Example | 11 | Comparative Example | A3-11 | | | — | — | — | 100 | 100 |
| | D(19) | | D4-(19) | NCM | LTO | 3Pa | 21-1 | 3 | 85 | 121 |
| | D(22) | | D4-(22) | | | | 21-2 | 3 | 85 | 118 |
| | D(25) | | D4-(25) | | | | 21-3 | 3 | 90 | 115 |
| | D(26) | | D4-(26) | | | | 21-4 | 3 | 90 | 114 |
| Example | 20 | Example | A4-20 | | | | — | — | 90 | 113 |
| Comparative Example | 11 | Comparative Example | A4-11 | | | — | — | — | 100 | 100 |
| | D(19) | | D5-(19) | LFP | Graphite | 3Pa | 21-1 | 3 | 70 | 158 |
| | D(22) | | D5-(22) | | | | 21-2 | 3 | 75 | 155 |
| | D(25) | | D5-(25) | | | | 21-3 | 3 | 80 | 138 |
| | D(26) | | D5-(26) | | | | 21-4 | 3 | 80 | 135 |
| Example | 20 | Example | A5-20 | | | | — | — | 80 | 123 |
| Comparative Example | 11 | Comparative Example | A5-11 | | | — | — | — | 100 | 100 |
| | D(19) | | D6-(19) | NCA | Graphite | 3Pa | 21-1 | 3 | 65 | 140 |
| | D(22) | | D6-(22) | | | | 21-2 | 3 | 70 | 136 |
| | D(25) | | D6-(25) | | | | 21-3 | 3 | 75 | 130 |
| | D(26) | | D6-(26) | | | | 21-4 | 3 | 75 | 130 |
| Example | 20 | Example | A6-20 | | | | — | — | 75 | 125 |
| Comparative Example | 11 | Comparative Example | A6-11 | | | — | — | — | 100 | 100 |
| | D(19) | | D7-(19) | LMO | Graphite | 3Pa | 21-1 | 3 | 55 | 148 |
| | D(22) | | D7-(22) | | | | 21-2 | 3 | 60 | 147 |
| | D(25) | | D7-(25) | | | | 21-3 | 3 | 70 | 135 |
| | D(26) | | D7-(26) | | | | 21-4 | 3 | 70 | 133 |
| Example | 20 | Example | A7-20 | | | | — | — | 70 | 117 |
| Comparative Example | 11 | Comparative Example | A7-11 | | | — | — | — | 100 | 100 |
| | D(19) | | D8-(19) | LCO | Graphite | 3Pa | 21-1 | 3 | 75 | 155 |
| | D(22) | | D8-(22) | | | | 21-2 | 3 | 75 | 150 |
| | D(25) | | D8-(25) | | | | 21-3 | 3 | 85 | 133 |
| | D(26) | | D8-(26) | | | | 21-4 | 3 | 85 | 132 |
| Example | 20 | Example | A8-20 | | | | — | — | 85 | 125 |
| Comparative Example | 11 | Comparative Example | A8-11 | | | — | — | — | 100 | 100 |

The invention claimed is:

1. An electrolyte for a nonaqueous electrolyte battery, comprising an ionic complex having a chemical structure represented by the following general formula (3):

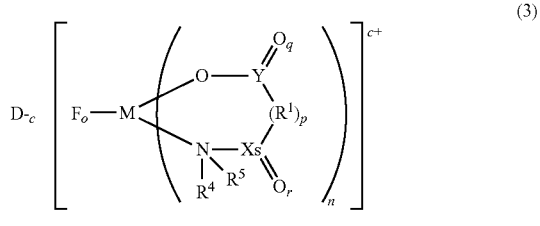
(3)

wherein in the general formula (3),

D is at least one selected from a halogen ion, a hexafluorophosphate anion, a tetrafluoroborate anion, a bis(trifluoromethane sulfonyl)imide anion, a bis(fluorosulfonyl)imide anion, a (fluorosulfonyl)(trifluoromethane sulfonyl)imide anion, and a bis(difluorophosphonyl)imide anion;

F is fluorine atom;

M is any one selected from the group consisting of Al, B, Si, P, As, and Sb;

O is oxygen atom;

N is nitrogen atom;

Y is carbon atom or sulfur atom, wherein when Y is carbon atom, q is 1, and when Y is sulfur atom, q is 1 or 2;

X is carbon atom or sulfur atom, wherein when X is carbon atom, r is 1, and when X is sulfur atom, r is 1 or 2;

$R^1$ represents a hydrocarbon group which may have a ring, a heteroatom, or a halogen atom, the hydrocarbon group having 1 to 10 carbon atoms, wherein $R^1$ may have a branched chain or a ring structure when the number of carbon atoms is 3 or more, or —N($R^2$)—, and at this time represents hydrogen atom, alkali metal atom, a hydrocarbon group which may have a ring, a heteroatom, or a halogen atom, the hydrocarbon group having 1 to 10 carbon atoms, wherein $R^2$ can also have a branched chain or a ring structure when the number of carbon atoms is 3 or more;

$R^4$ and $R^5$ each independently represents a hydrocarbon group which may have a ring, a heteroatom, or a halogen atom, the hydrocarbon group having 1 to 10 carbon atoms, wherein $R^4$ and $R^5$ can also have a branched chain or a ring structure when a number of carbon atoms is 3 or more, and may also have a ring structure including each other as shown in the following general formula (4):

(4)

c is 0 or 1, wherein when n is 1, c is 0, in which when c is 0, D is absent, and when n is 2, c is 1;

o is 2 or 4, n is 1 or 2, p is 0 or 1, q is 1 or 2, r is 1 or 2, and s is 0 or 1, wherein when p is 0, a direct bond is formed between Y and X;

when s is 0, $N(R^4)(R^5)$ and $R^1$ are directly bonded to each other, and, at that time, can also have structures of the following (5) to (8),

(5)

(6)

(7)

(8)

wherein in (6) and (8), the direct bond is a double bond, $R^5$ is absent, and as shown in (7), a structure in which the double bond is out of the ring may also be taken; and $R^6$ and $R^7$ in this case each independently represents hydrogen atom, a hydrocarbon group which may have a ring, a heteroatom, or a halogen atom, the hydrocarbon group having 1 to 10 carbon atoms, wherein when the number of carbon atoms is 3 or more, $R^6$ and $R^7$ can also have a branched chain or a ring structure.

2. The electrolyte for a nonaqueous electrolyte battery according to claim 1, wherein the ionic complex represented by the general formula (3) is any one selected from the group consisting of the following 3Pa, 3Pb, 3Pd, 3Pg, 3Ba, 3Bb, 3Bf, 3Bg, and 3Bi.

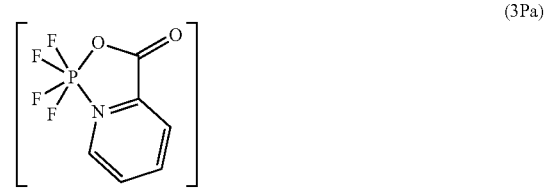
(3Pa)

(3Pb)

(3Pd)

-continued

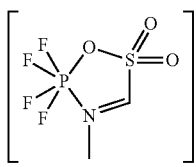 (3Pg)

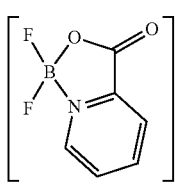 (3Ba)

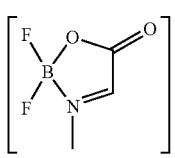 (3Bb)

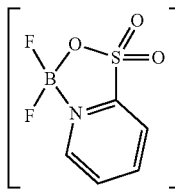 (3Bf)

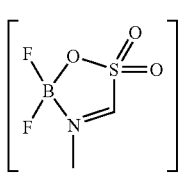 (3Bg)

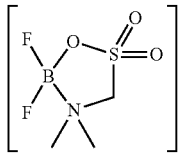 (3Bi)

3. The electrolyte for a nonaqueous electrolyte battery according to claim 1, wherein the D is at least one anion selected from the group consisting of a hexafluorophosphate anion, a tetrafluoroborate anion, a bis(trifluoromethane sulfonyl)imide anion, a bis(fluorosulfonyl)imide anion, a (fluorosulfonyl)(trifluoromethane sulfonyl)imide anion, and a bis(difluorophosphonyl)imide anion.

4. The electrolyte for a nonaqueous electrolyte battery according to claim 1, wherein the M is B or P.

5. An electrolyte for a nonaqueous electrolyte battery according to claim 1, further comprising a solute and a nonaqueous organic solvent.

6. The electrolyte for a nonaqueous electrolyte battery according to claim 5, wherein the solute is a salt comprising a pair of
at least one cation selected from the group consisting of an alkali metal ion, an alkaline earth metal ion, and quaternary ammonium, and
at least one anion selected from the group consisting of anions of hexafluorophosphate, tetrafluoroborate, perchlorate, hexafluoroarsenate, hexafluoroantimonate, trifluoromethanesulfonate, bis(trifluoromethane sulfonyl)imide, bis(pentafluoroethane sulfonyl)imide, (trifluoromethane sulfonyl)(pentafluoroethane sulfonyl) imide, bis(fluorosulfonyl)imide, (trifluoromethane sulfonyl)(fluorosulfonyl)imide, (pentafluoroethane sulfonyl)(fluorosulfonyl)imide, tris(trifluoromethane sulfonyl)methide, and bis(difluorophosphonyl)imide.

7. The electrolyte for a nonaqueous electrolyte battery according to claim 5, wherein the nonaqueous organic solvent is at least one selected from the group consisting of carbonates, esters, ethers, lactones, nitriles, imides, and sulfones.

8. The electrolyte for a nonaqueous electrolyte battery according to claim 5, wherein the nonaqueous organic solvent is at least one selected from the group consisting of ethyl methyl carbonate, dimethyl carbonate, diethyl carbonate, methyl propyl carbonate, ethyl propyl carbonate, methyl butyl carbonate, ethylene carbonate, propylene carbonate, butylene carbonate, methyl acetate, methyl propionate, ethyl propionate, diethyl ether, acetonitrile, propionitrile, tetrahydrofuran, 2-methyltetrahydrofuran, furan, tetrahydropyran, 1,3-dioxane, 1,4-dioxane, dibutyl ether, diisopropyl ether, 1,2-dimethoxyethane, N,N-dimethylformamide, dimethylsulfoxide, sulfolane, γ-butyrolactone, and γ-valerolactone.

9. The electrolyte for a nonaqueous electrolyte battery according to claim 5, wherein the nonaqueous organic solvent contains at least one selected from the group consisting of cyclic carbonate and chain carbonate.

10. The electrolyte for a nonaqueous electrolyte battery according to claim 9, wherein the cyclic carbonate is at least one selected from the group consisting of ethylene carbonate, propylene carbonate, and butylene carbonate; and the chain carbonate is at least one selected from the group consisting of ethyl methyl carbonate, dimethyl carbonate, diethyl carbonate, methyl propyl carbonate, ethyl propyl carbonate, and methyl butyl carbonate.

11. The electrolyte for a nonaqueous electrolyte battery according to claim 1, wherein an addition concentration of the ionic complex is in a range from 0.001 to 20 mass % with respect to a total amount of the solute, the nonaqueous organic solvent, and the ionic complex.

12. The electrolyte for a nonaqueous electrolyte battery according to claim 1, further comprising at least one second compound selected from the group consisting of fluorine-containing compounds represented by the following general formulae (9) to (16):

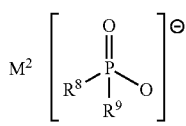 (9)

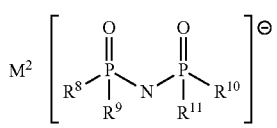 (10)

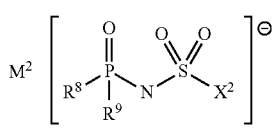 (11)

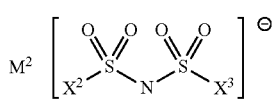 (12)

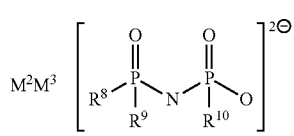

(13)

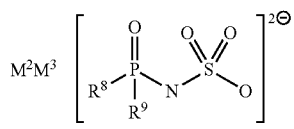

(14)

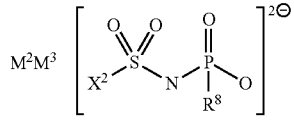

(15)

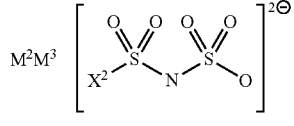

(16)

wherein in the general formulae (9) to (11) and (13) to (15), $R^8$ to $R^{11}$ each independently represents a fluorine atom and an organic group selected from a straight chain or branched alkoxy group having 1 to 10 carbon atoms, an alkenyloxy group having 2 to 10 carbon atoms, an alkynyloxy group having 2 to 10 carbon atoms, a cycloalkoxy group and a cycloalkenyloxy group having 3 to 10 carbon atoms, and an aryloxy group having 6 to 10 carbon atoms, and the organic group can include a fluorine atom, an oxygen atom, and an unsaturated bond;

in the general formulae (11), (12), (15), and (16), $X^2$ and $X^3$ each independently represents a fluorine atom and an organic group selected from a straight chain or branched alkyl group having 1 to 10 carbon atoms, an alkenyl group having 2 to 10 carbon atoms, an alkynyl group having 2 to 10 carbon atoms, a cycloalkyl group and a cycloalkenyl group having 3 to 10 carbon atoms, an aryl group having 6 to 10 carbon atoms, a straight chain or branched alkoxy group having 1 to 10 carbon atoms, an alkenyloxy group having 2 to 10 carbon atoms, an alkynyloxy group having 2 to 10 carbon atoms, a cycloalkoxy group and a cycloalkenyloxy group having 3 to 10 carbon atoms, and an aryloxy group having 6 to 10 carbon atoms, and the organic group also can include a fluorine atom, an oxygen atom, and an unsaturated bond; and the general formulae (9) to (16) include at least one bond selected from a P—F bond and a S—F bond, and $M^2$ and $M^3$ each independently represents a proton, a metal cation, or an onium cation.

13. The electrolyte for a nonaqueous electrolyte battery according to claim 12, wherein $R^8$ to $R^{11}$ of the general formulae (9) to (11) and (13) to (15) are a fluorine atom and an organic group selected from the group consisting of a straight chain or branched alkoxy group including a fluorine atom having 1 to 10 carbon atoms, an alkenyloxy group having 2 to 10 carbon atoms, and an alkynyloxy group having 2 to 10 carbon atoms.

14. The electrolyte for a nonaqueous electrolyte battery according to claim 13, wherein the alkoxy group is selected from the group consisting of a 2,2,2-trifluoroethoxy group, a 2,2,3,3-tetrafluoropropoxy group, a 1,1,1-trifluoroisopropoxy group, and a 1,1,1,3,3,3-hexafluoroisopropoxy group; the alkenyloxy group is selected from the group consisting of 1-propenyloxy group, 2-propenyloxy group, and 3-butenyloxy group; and the alkynyloxy group is selected from the group consisting of 2-propynyloxy group, and 1,1-dimethyl-2-propynyloxy group.

15. The electrolyte for a nonaqueous electrolyte battery according to claim 12, wherein $X^2$ and $X^3$ of the general formulae (11), (12), (15), and (16) are a fluorine atom and an organic group selected from the group consisting of a straight chain or branched alkoxy group having 1 to 10 carbon atoms, an alkenyloxy group having 2 to 10 carbon atoms, and an alkynyloxy group having 2 to 10 carbon atoms.

16. The electrolyte for a nonaqueous electrolyte battery according to claim 15, wherein the alkoxy group is selected from the group consisting of a methoxy group, an ethoxy group, and a propoxy group; the alkenyloxy group is selected from the group consisting of a 1-propenyloxy group, a 2-propenyloxy group, and a 3-butenyloxy group; and the alkynyloxy group is selected from the group consisting of a 2-propynyloxy group, and a 1,1-dimethyl-2-propynyloxy group.

17. The electrolyte for a nonaqueous electrolyte battery according to claim 12, wherein $M^2$ and $M^3$ of the general formulae (9) to (16) are at least one cation selected from the group consisting of a lithium ion, a sodium ion, a potassium ion, a tetraalkyl ammonium ion, and tetraalkyl phosphonium ion.

18. The electrolyte for a nonaqueous electrolyte battery according to claim 12, wherein an addition concentration of the second compound is in a range from 0.001 to 10.0 mass % with respect to a total amount of the solute, the nonaqueous organic solvent, the ionic complex, and the second compound.

19. The electrolyte for a nonaqueous electrolyte battery according to claim 1, further comprising at least one third compound represented by the following general formula (17):

wherein in the general formula (17), $R^{12}$ each independently represents a group having an unsaturated carbon-carbon bond;

$R^{13}$ each independently represents a fluorine atom and a group selected from the group consisting of an alkyl group, an alkoxy group, an alkenyl group, an alkenyloxy group, an alkynyl group, an alkynyloxy group, an aryl group, and an aryloxy group, and these groups may include any one of a fluorine atom and an oxygen atom; and x is 2 to 4.

20. The electrolyte for a nonaqueous electrolyte battery according to claim 19, wherein a group represented by $R^{12}$ of the general formula (17) each independently represents a group selected from the group consisting of a vinyl group, an allyl group, a 1-propenyl group, an ethynyl group, and a 2-propynyl group.

21. The electrolyte for a nonaqueous electrolyte battery according to claim 19, wherein a group represented by $R^{13}$ of the general formula (17) each independently represents a fluorine atom and a group selected from the group consisting of a methyl group, an ethyl group, a propyl group, a 2,2,2-trifluoroethyl group, a 2,2,3,3-tetrafluoropropyl group, a 1,1,1-trifluoroisopropyl group, a 1,1,1,3,3,3-hexafluoroisopropyl group, a 2,2,2-trifluoroethoxy group, a 2,2,3,3- tetrafluoropropoxy group, a 2,2,3,3,3-pentafluoropropoxy group, a 1,1,1-trifluoroisopropoxy group, and a 1,1,1,3,3,3-hexafluoroisopropoxy group.

22. The electrolyte for a nonaqueous electrolyte battery according to claim 19, wherein x in the general formula (17) is 2 to 3.

23. The electrolyte for a nonaqueous electrolyte battery according to claim 19, wherein an addition concentration of the third compound with respect to a total amount of the solute, the nonaqueous organic solvent, the ionic complex, and the third compound is in a range from 0.005 to 7.0 mass %.

24. The electrolyte for a nonaqueous electrolyte battery according to claim 1, further comprising a fourth compound that is at least one selected from the group consisting of a cyclic sulfonic acid compound represented by the following general formulae (18), (19), and (20), 1,3-propane sultone, and 1,2-pentanediol sulfate ester;

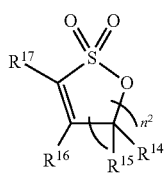

(18)

wherein in the formula (18), O is an oxygen atom; S is a sulfur atom; $n^2$ is an integer of 1 or more and 3 or less; and $R^{14}$, $R^{15}$, $R^{16}$, and $R^{17}$ each independently represents a hydrogen atom, a substituted or non-substituted alkyl group having 1 or more and 5 or less carbon atoms, or a substituted or non-substituted fluoroalkyl group having 1 or more and 4 or less carbon atoms,

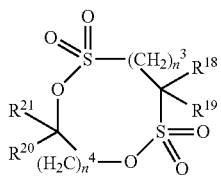

(19)

wherein in the formula (19), O is an oxygen atom; S is a sulfur atom; $n^3$ is an integer of 0 or more and 4 or less; $R^{18}$ and $R^{19}$ each independently represents a hydrogen atom, a halogen atom, or a substituted or non-substituted alkyl group having 1 or more and 5 or less carbon atoms; and $R^{20}$ and $R^{21}$ each independently represents a hydrogen atom, a halogen atom, a substituted or non-substituted alkyl group having 1 to 5 carbon atoms, or substituted or non-substituted fluoroalkyl group having 1 or more and 4 or less carbon atoms, and $n^4$ is an integer of 0 or more and 4 or less,

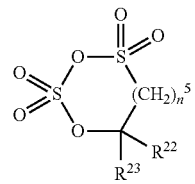

(20)

wherein in the formula (20), O is an oxygen atom; S is a sulfur atom; $n^5$ is an integer of 0 to 3; and $R^{22}$ and $R^{23}$ each independently represents a hydrogen atom, a halogen atom, a substituted or non-substituted alkyl group having 1 or more and 5 or less carbon atoms, or a substituted or non-substituted fluoroalkyl group having 1 or more and 4 or less carbon atoms.

25. The electrolyte for a nonaqueous electrolyte battery according to claim 24, wherein an addition concentration of the fourth compound is in a range from 0.001 to 10 mass % with respect to a total amount of a solute, a nonaqueous organic solvent, an ionic complex, and the fourth compound.

26. The electrolyte for a nonaqueous electrolyte battery according to claim 1, further comprising a fifth compound that is at least one selected from the group consisting of a cyclic carbonate compound represented by the following general formula (21):

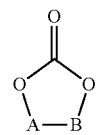

(21)

wherein in the formula (21), O is an oxygen atom, A is hydrocarbon having 10 or less carbon atoms and optionally including an unsaturated bond or a ring structure or a halogen atom, and B is hydrocarbon having 10 or less carbon atoms and optionally including an unsaturated bond or a ring structure or a halogen atom, and
a double bond may be formed between A and B.

27. The electrolyte for a nonaqueous electrolyte battery according to claim 26, wherein an addition concentration of the fifth compound is in a range from 0.001 to 10 mass % with respect to a total amount of a solute, a nonaqueous organic solvent, an ionic complex, and the fifth compound.

28. A nonaqueous electrolyte battery comprising:
a positive electrode;
a negative electrode including lithium or a negative electrode material capable of absorbing/releasing lithium; and
an electrolyte for a nonaqueous electrolyte battery according to claim 1.

29. A nonaqueous electrolyte battery comprising:
a positive electrode;
a negative electrode including sodium or a negative electrode material capable of absorbing/releasing sodium; and
an electrolyte for a nonaqueous electrolyte battery according to claim 1.

* * * * *